United States Patent
Esteves et al.

(10) Patent No.: US 11,020,443 B2
(45) Date of Patent: Jun. 1, 2021

(54) MODULATION OF AAV VECTOR TRANSGENE EXPRESSION

(71) Applicant: University of Massachusetts, Boston, MA (US)

(72) Inventors: Miguel Sena Esteves, Westford, MA (US); Cara Weismann, Worcester, MA (US); Diane Golebiowski, Lexington, MA (US); Lorelei Stoica, Worcester, MA (US)

(73) Assignee: University of Massachusetts, Boston, MA (US)

( * ) Notice: Subject to any disclaimer, the term of this patent is extended or adjusted under 35 U.S.C. 154(b) by 91 days.

(21) Appl. No.: 15/567,847

(22) PCT Filed: Apr. 20, 2016

(86) PCT No.: PCT/US2016/028367
§ 371 (c)(1),
(2) Date: Oct. 19, 2017

(87) PCT Pub. No.: WO2016/172155
PCT Pub. Date: Oct. 27, 2016

(65) Prior Publication Data
US 2018/0311290 A1    Nov. 1, 2018

Related U.S. Application Data

(60) Provisional application No. 62/151,988, filed on Apr. 23, 2015.

(51) Int. Cl.
| | |
|---|---|
| *A61K 35/761* | (2015.01) |
| *A61K 48/00* | (2006.01) |
| *A61P 25/28* | (2006.01) |
| *A61P 43/00* | (2006.01) |
| *C12N 15/861* | (2006.01) |
| *C12N 15/86* | (2006.01) |
| *C12N 9/24* | (2006.01) |
| *C12N 9/38* | (2006.01) |

(52) U.S. Cl.
CPC ............ *A61K 35/761* (2013.01); *A61K 48/00* (2013.01); *A61K 48/0058* (2013.01); *A61K 48/0066* (2013.01); *A61P 25/28* (2018.01); *A61P 43/00* (2018.01); *C12N 9/2402* (2013.01); *C12N 9/2471* (2013.01); *C12N 15/86* (2013.01); *C12N 15/861* (2013.01); *C12N 2750/14143* (2013.01); *C12Y 302/01023* (2013.01); *C12Y 302/01052* (2013.01)

(58) Field of Classification Search
None
See application file for complete search history.

(56) References Cited

U.S. PATENT DOCUMENTS

| | | |
|---|---|---|
| 5,475,095 A | 12/1995 | Myerowitz et al. |
| 6,797,265 B2 | 9/2004 | Amalfitano et al. |
| 7,858,367 B2 | 12/2010 | Amalfitano et al. |
| 2002/0164783 A1 | 11/2002 | Feldhaus |
| 2004/0192630 A1 | 9/2004 | Kyrkanides |
| 2008/0226615 A1 | 9/2008 | Kyrkanides et al. |
| 2012/0309050 A1 | 12/2012 | Kumon et al. |
| 2013/0090374 A1 | 4/2013 | Sena-Esteves et al. |
| 2015/0065560 A1 | 3/2015 | Bjorklund et al. |
| 2015/0258180 A1 | 9/2015 | Mahuran et al. |
| 2016/0243260 A1 | 8/2016 | Blits |
| 2019/0111157 A1 | 4/2019 | Stanek et al. |

FOREIGN PATENT DOCUMENTS

| | | | |
|---|---|---|---|
| AU | 2013202568 B2 * | 5/2013 | |
| CN | 1429905 A | 7/2003 | |
| EP | 0669987 B1 | 8/2008 | |
| EP | 1501465 B1 | 10/2009 | |
| EP | 1620133 B1 | 12/2015 | |
| EP | 2996475 A1 | 3/2016 | |
| WO | WO 2008/154198 * | 12/2008 | |
| WO | WO-2008154198 A1 * | 12/2008 | ............. C12N 15/86 |
| WO | WO 2010/027446 A2 | 3/2010 | |
| WO | WO 2012/145646 A1 | 10/2012 | |
| WO | WO 2016/172155 | 10/2016 | |

OTHER PUBLICATIONS

Xu et al., Human Gene Therapy, 2001, 12:563-573. (Year: 2001).*
Seo et al., BMC Biotechnology, 2010, 10:69. (Year: 2010).*
Yang et al., Molecular Therapy, May 2012, 20:Supplement 1, Abstract 526. (Year: 2015).*
EP 16783726.9, Nov. 7, 2018, Extended European Search Report.
PCT/US2016/028367, Aug. 31, 2016, International Search Report and Written Opinion.
PCT/US2016/028367, Nov. 2, 2017, International Preliminary Report on Patentability.
Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.
McCurdy et al., Sustained normalization of neurological disease after intracranial gene therapy in a feline model. Sci Transl Med. Apr. 9, 2014;6(231):231ra48. doi: 10.1126/scitranslmed.3007733.
Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.
Weismann, Approaches and Considerations Towards a Safe and Effective Adeno-Associated Virus Mediated Therapeutic Intervention for GM 1-Gangliosidosis: A Dissertation. University Massachusetts Medical School. Aug. 5, 2014.

(Continued)

*Primary Examiner* — Nicole Kinsey White
(74) *Attorney, Agent, or Firm* — Fish & Richardson P.C.

(57) ABSTRACT

Aspects of the invention relate to recombinant adeno-associated viruses (rAAVs). In some aspects, the rAAVs comprise artificial genetic regulatory elements that modulate transgene expression. In some aspects, the disclosure relates to the treatment of lysosomal storage disorders.

13 Claims, 74 Drawing Sheets

Specification includes a Sequence Listing.

(56) References Cited

OTHER PUBLICATIONS

Invitation to Pay Additional Fees for Application No. PCT/US2018/27271, dated Jun. 27, 2019.
International Search Report and Written Opinion for Application No. PCT/US2018/27271, dated Sep. 11, 2019.
PCT/US2019/27271, Jun. 27, 2019, Invitation to Pay Additional Fees.
PCT/US2019/28281, Sep. 11, 2019, International Search Report and Written Opinion.
Bera et al., "Bicistronic AAV Gene Therapy Vectors for Tay-Sachs Disease," Molecular Therapy, May 1, 2008, 16:S42.
Cachón-González et al., "Effective gene therapy in an authentic model of Tay-Sachs-related diseases," Proceedings of the National Academy of Sciences, Jul. 5, 2006, 103(27):10373-8.
Cachón-González et al., "Gene transfer corrects acute GM2 gangliosidosis—potential therapeutic contribution of perivascular enzyme flow," Molecular Therapy, Aug. 1, 2012, 20(8):1489-500.
Cachón-González et al., "Reversibility of neuropathology in Tay—Sachs-related diseases." Human Molecular Genetics, Feb. 1, 2014, 23(3):730-48.
Curtin et al., "Bidirectional promoter interference between two widely used internal heterologous promoters in a late-generation lentiviral construct," Gene Therapy, Mar. 2008, 15(5):384-90.
EP European Search Report in European Appln. No. 16783726.9, dated Nov. 7, 2018, 11 pages.
EP Office Action in European Appln. No. 16783726.9, dated Aug. 7, 2020, 7 pages.
EP Office Action in European Appln. No. 16783726.9, dated Dec. 6, 2019, 7 pages.
Guidotti et al., "Adenoviral gene therapy of the Tay-Sachs disease in hexosaminidase A-deficient knock-out mice," Human Molecular Genetics, May 1, 1999, 8(5)831-8.
Karumuthil-Melethil et al., "Novel vector design and hexosaminidase variant enabling self-complementary adeno-associated virus for the treatment of Tay-Sachs disease," Human Gene Therapy, Jul. 1, 2016, 27(7):509-21.

Martin-Duque et al., "Direct comparison of the insulating properties of two genetic elements in an adenoviral vector containing two different expression cassettes," Human Gene Therapy, Oct. 1, Oct. 1, 2004;15(10):995-1002.
Myerowitz et al., "Human beta-hexosaminidase alpha chain: coding sequence and homology with the beta chain," Proceedings of the National Academy of Sciences, Dec. 1, 1985, 82(23):7830-4.
PCT International Preliminary Report on Patentability in International Appln. No. PCT/US2016/028367, dated Oct. 24, 2017, 8 pages.
PCT International Preliminary Report on Patentability in International Appln. No. PCT/US2019/0272711, 8 pages, Oct. 13, 2020.
PCT International Search Report and Written Opinion in International Application No. PCT/US2018/27271, dated Sep. 11, 2019, 7 pages.
PCT International Search Report and Written Opinion in International Appln. No. PCT/US2016/028367, dated Aug. 31, 2016, 24 pages.
PCT Invitation to Pay Additional Fees in International Appln. No. PCT/US2019/27271, dated Jun. 27, 2019, 3 pages.
Solovyeva, et al., "New approaches to Tay-Sachs disease therapy," Frontiers in Physiology, Nov. 20, 2018, 9:1663, 11 pages.
Sondhi et al., "AAV2-mediated CLN2 gene transfer to rodent and non-human primate brain results in long-term TPP-I expression compatible with therapy for LINCL," Gene Therapy, Nov. 2005, 12(22):1618-32.
Golebiow ski et al., "Optimization of AAV Vector Design for Safe Expression of β-N-Acetylhexosaminidase the Brain for Tay-Sachs Disease Gene Therapy," Molecular Therapy, May 1, 2015, 23:S283.
Lahey et al., "Pronounced therapeutic benefit of a single bidirectional AAV vector administered systemically in Sandhoff mice," Molecular Therapy, Oct. 7, 2020. 28(10):2150-60.
Woodley et al., "Efficacy of a bicistronic vector for correction of Sandhoff disease in a mouse model," Molecular Therapy-Methods & Clinical Development, Mar. 15, 2019, 12:47-57.

* cited by examiner

KO Untreated

KO + AAV, 4E10/vg

CA Untreated

KO + AAV, 2.6E10vg

KO + AAV, 2.6E9vg

KO + AAV                    KO Utreated
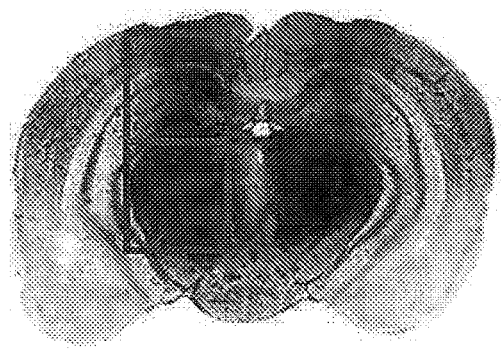 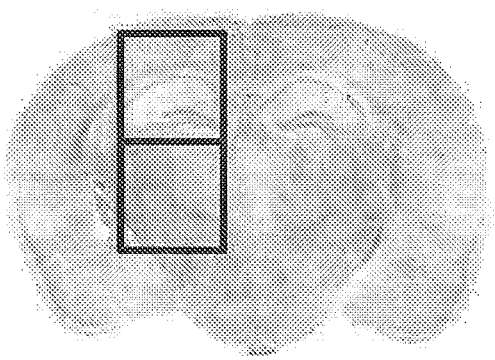
FIG. 5A                     FIG. 5B
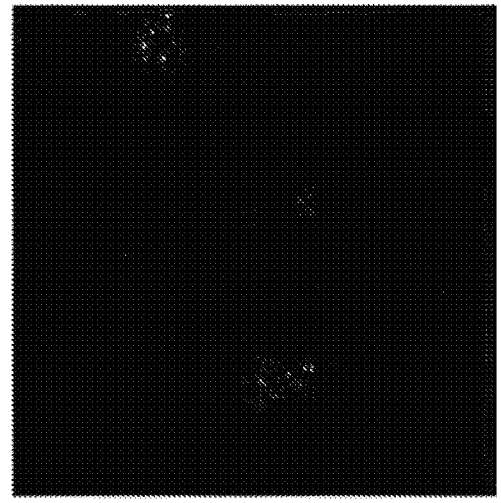 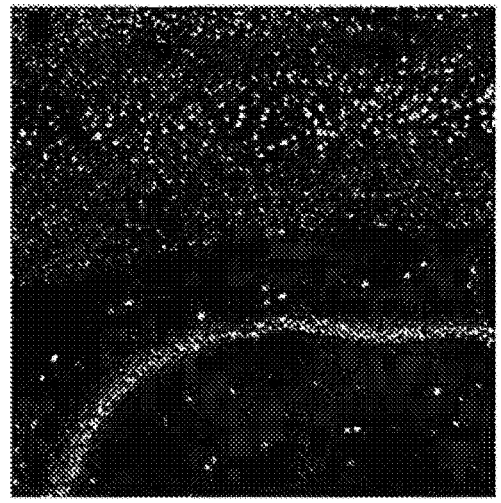
FIG. 5C                     FIG. 5D
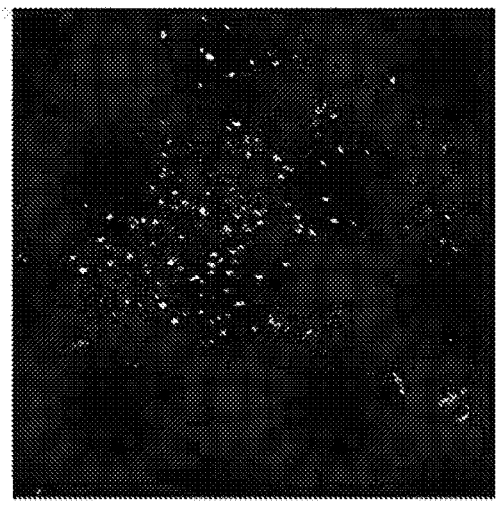 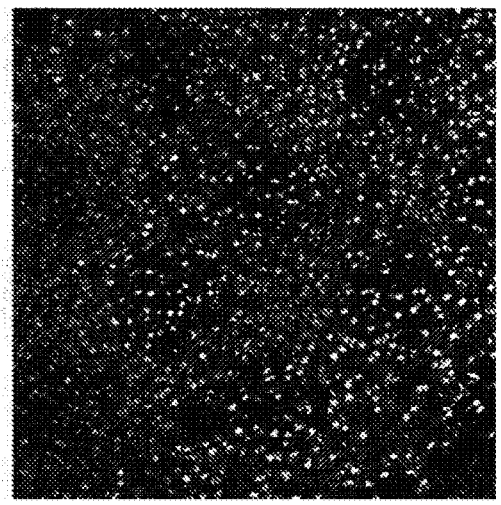
FIG. 5E                     FIG. 5F

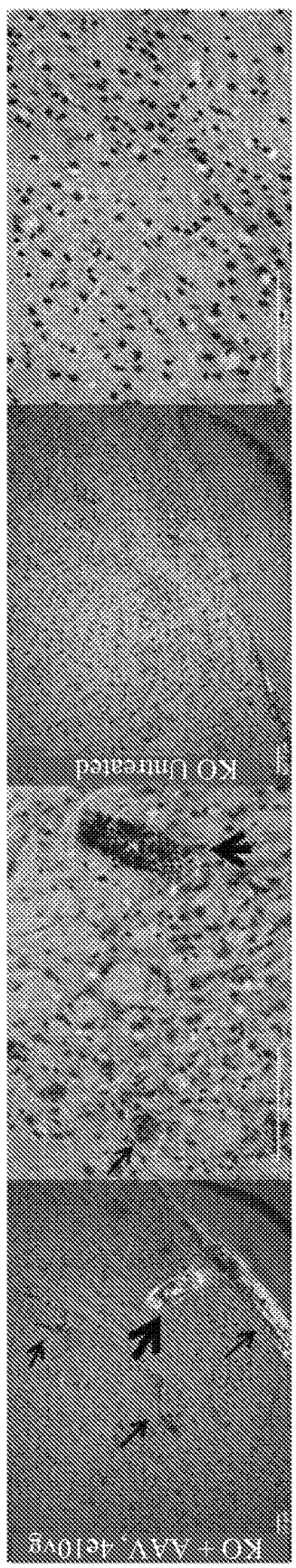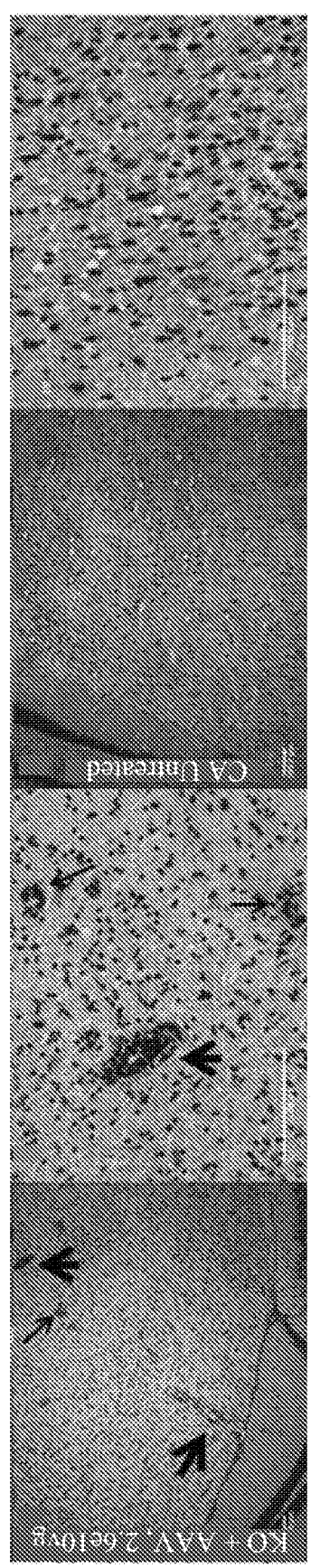

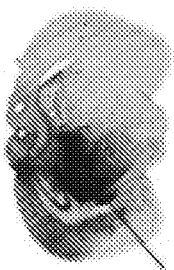
FIG. 7K
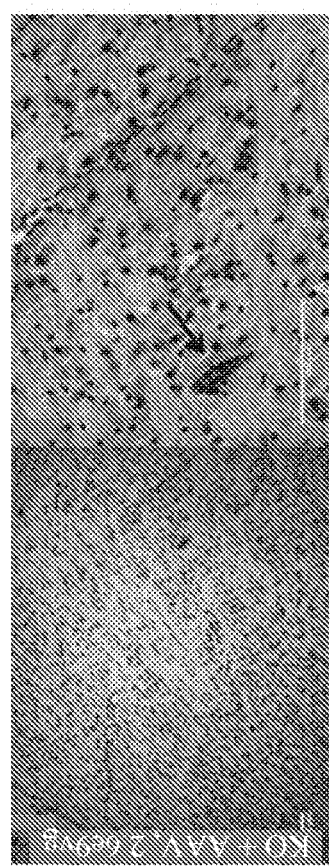
FIG. 7J
FIG. 7I

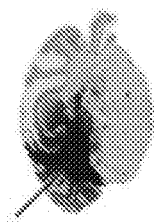
FIG. 8K
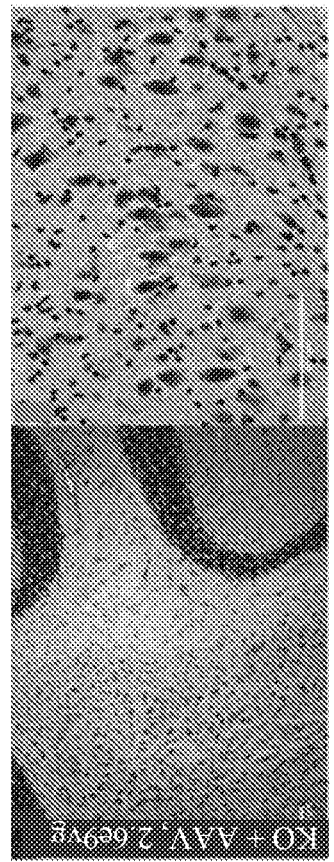
FIG. 8J
FIG. 8I

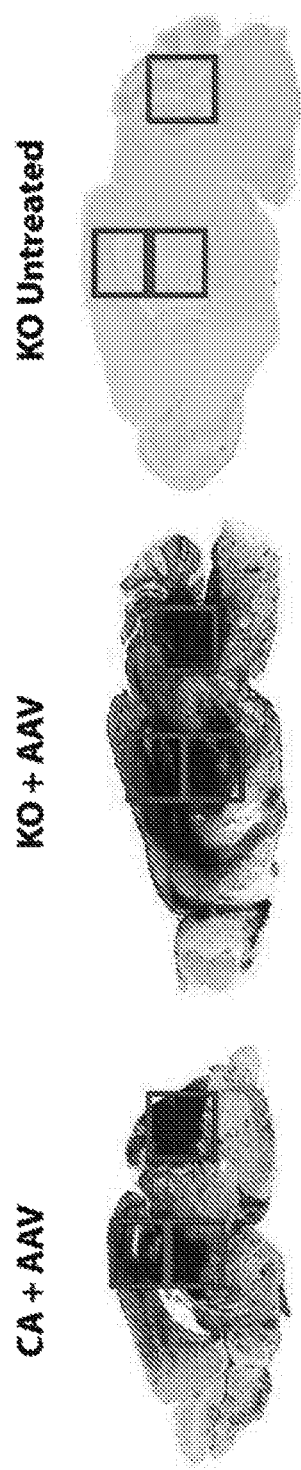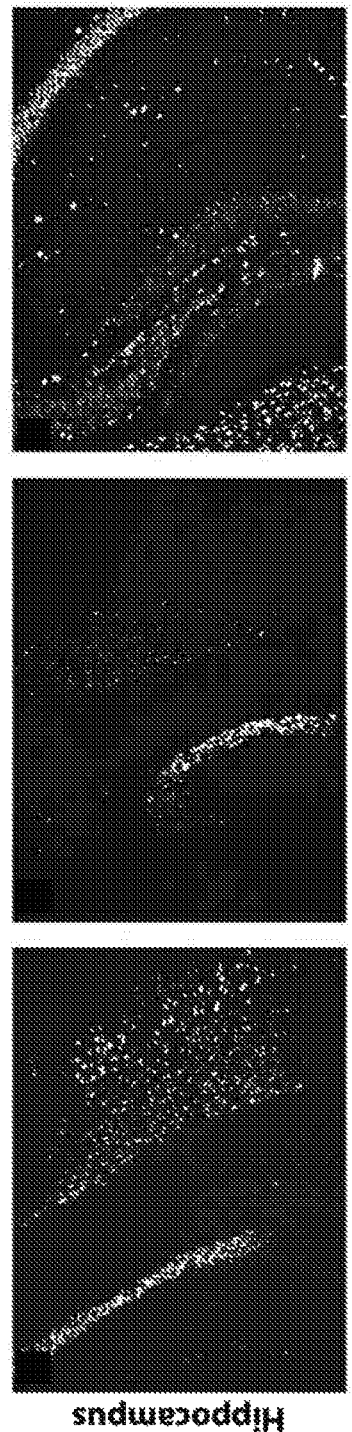

FIG. 10A
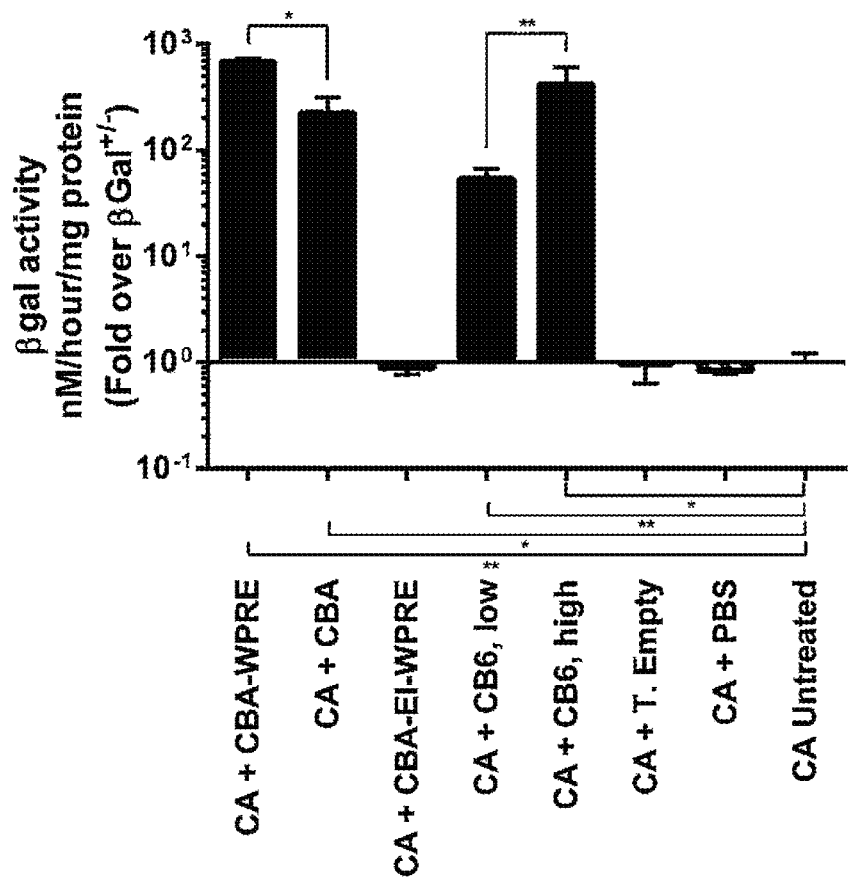
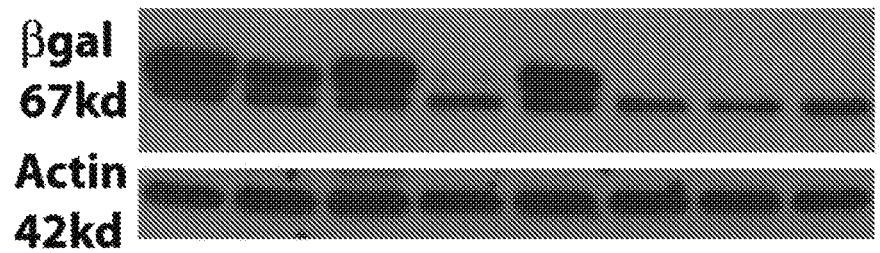
FIG. 10B

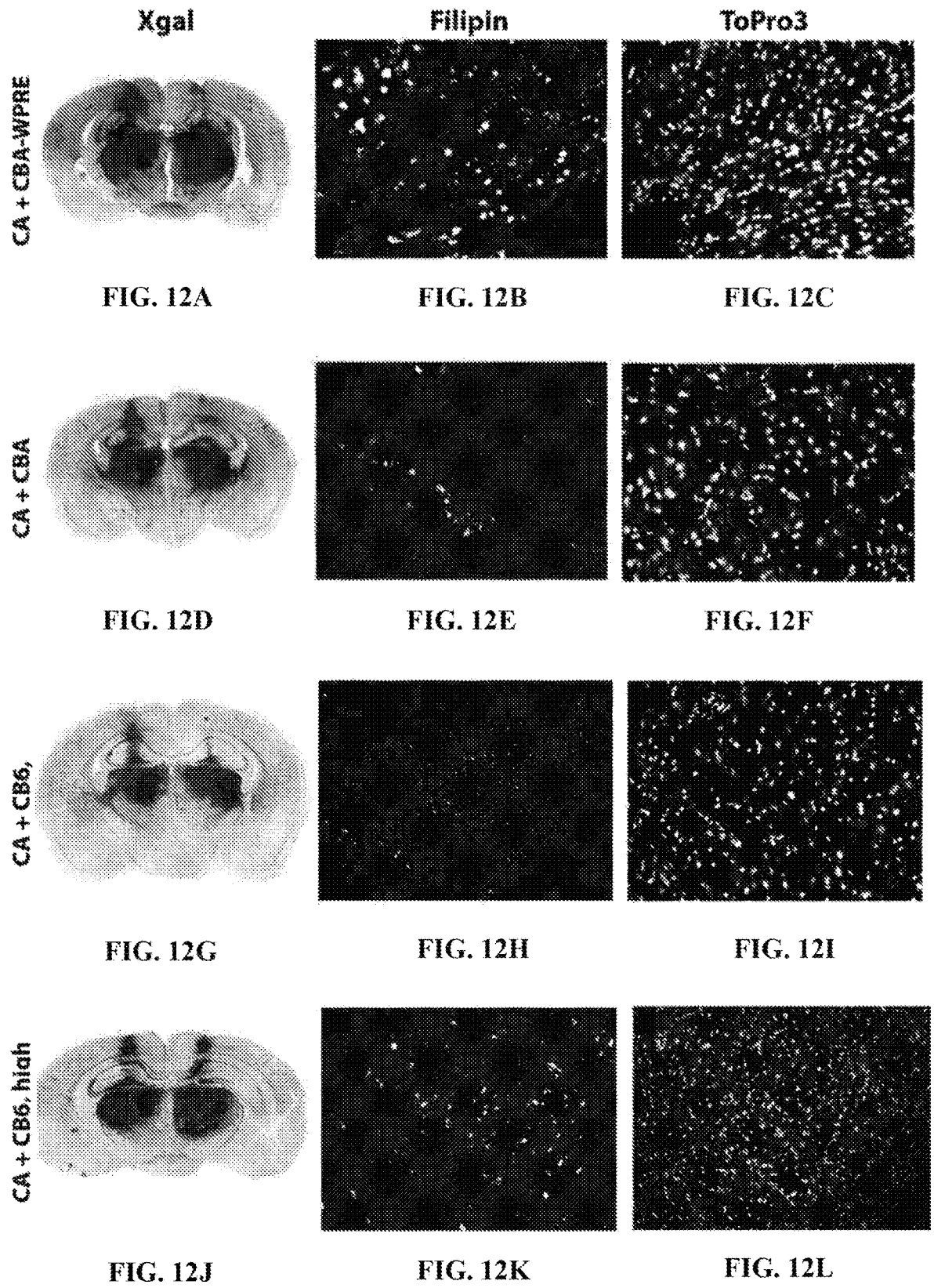

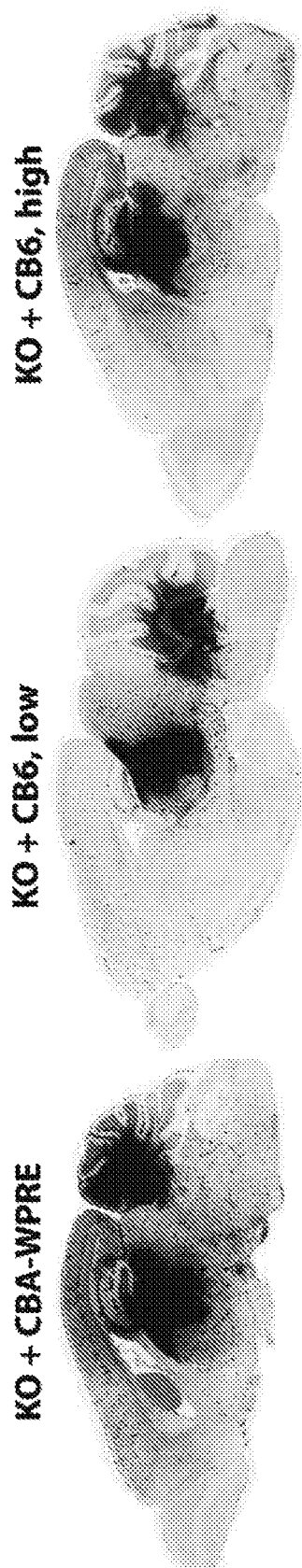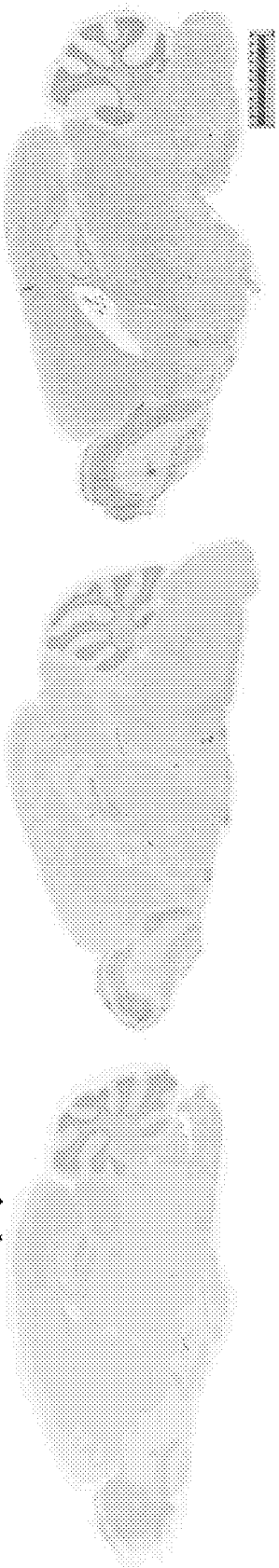
FIG. 15A  FIG. 15B  FIG. 15C
FIG. 15D  FIG. 15E  FIG. 15F

Cervical | Thoracic
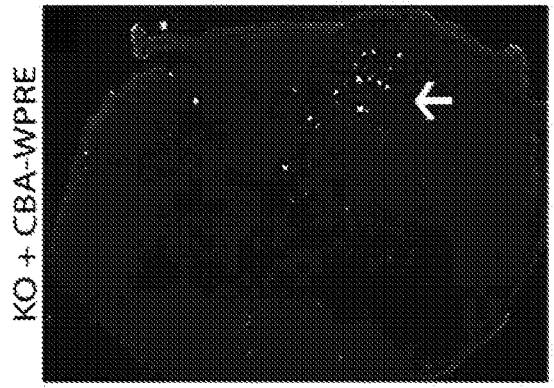
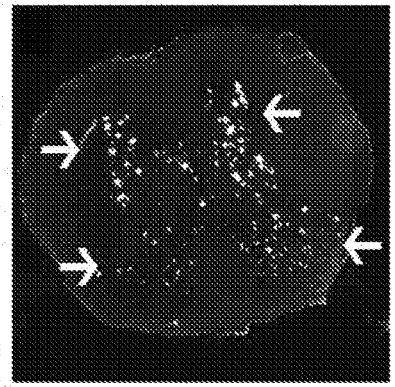
FIG. 17A | FIG. 17B
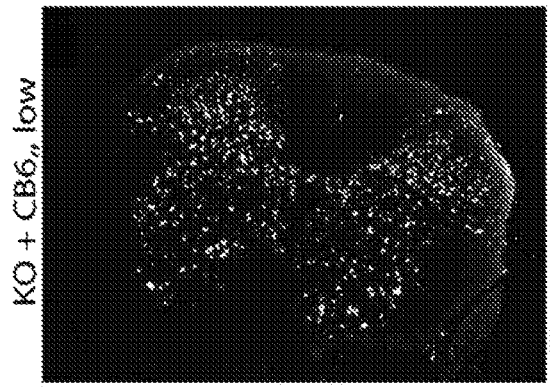
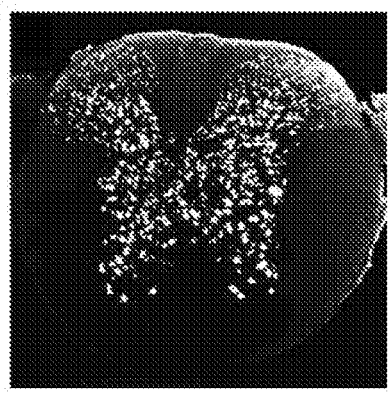
FIG. 17C | FIG. 17D
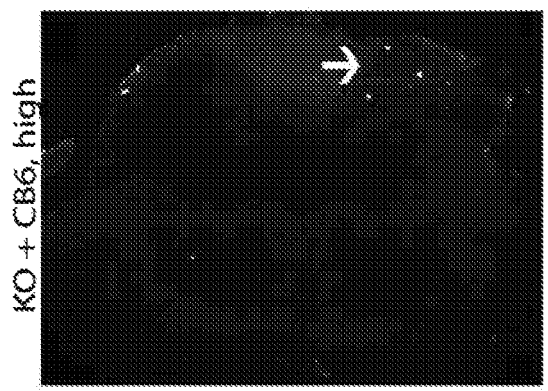
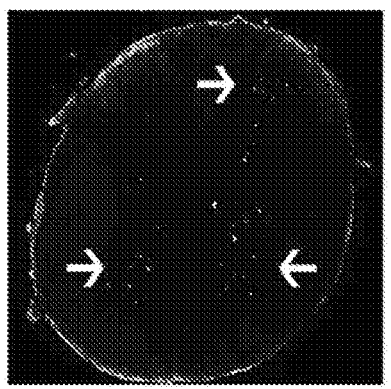
FIG. 17E | FIG. 17F

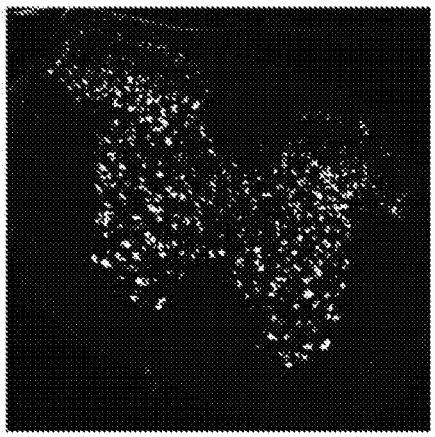
FIG. 17G  FIG. 17H
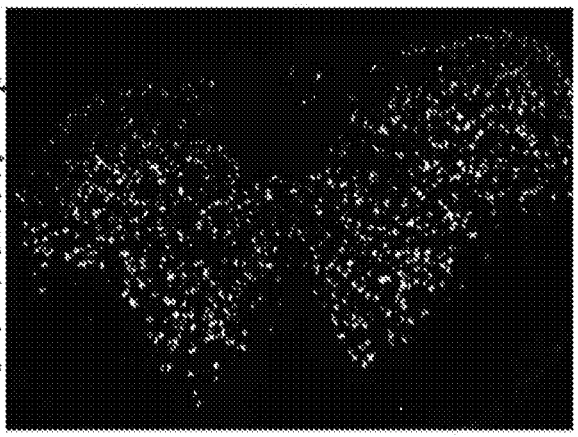
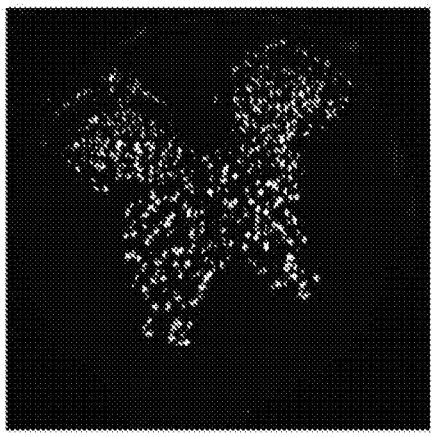
FIG. 17I  FIG. 17J
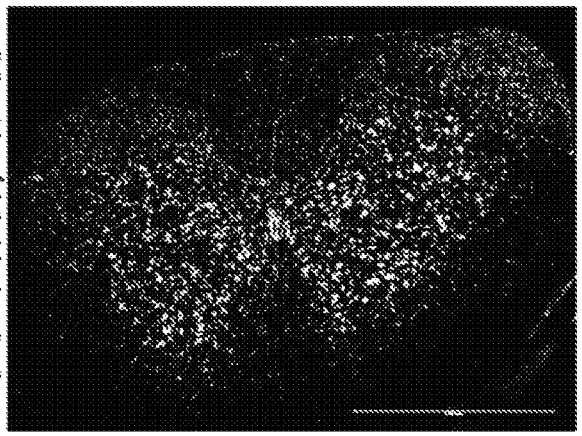
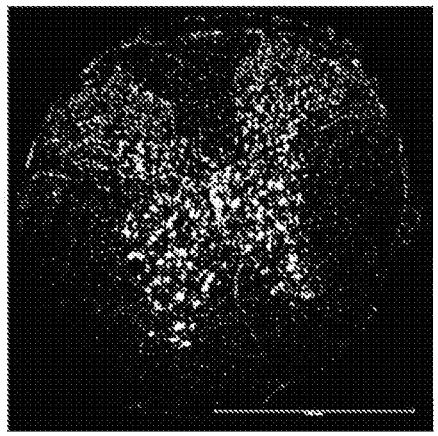
FIG. 17K  FIG. 17L

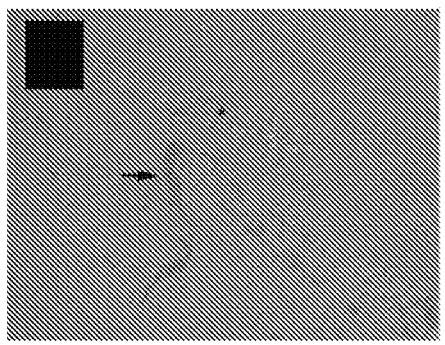 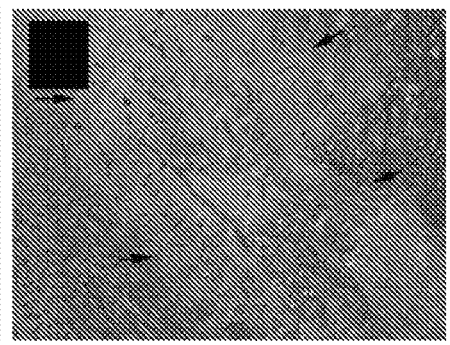
FIG. 22A　　　　　FIG. 22B
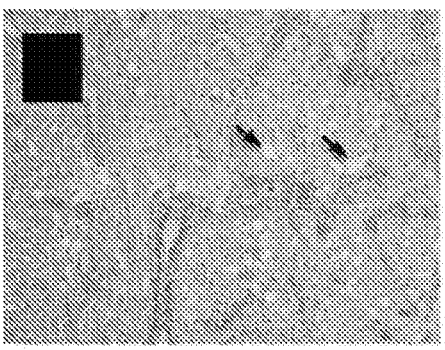 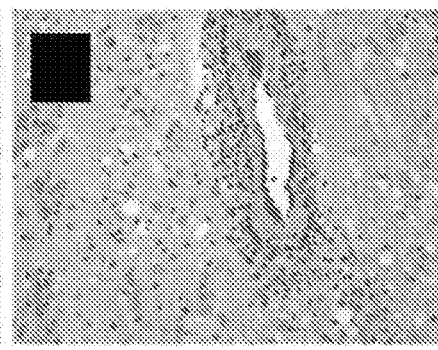
FIG. 22C　　　　　FIG. 22D
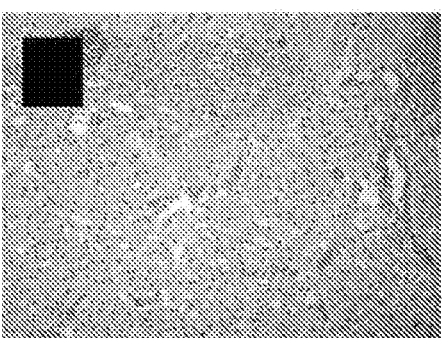 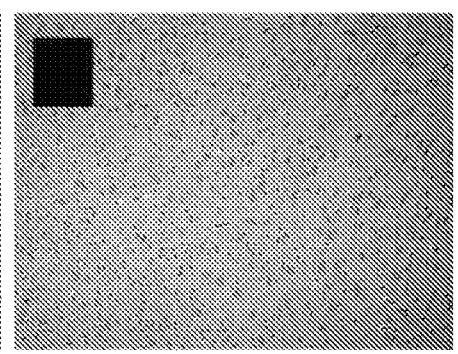
FIG. 22E　　　　　FIG. 22F

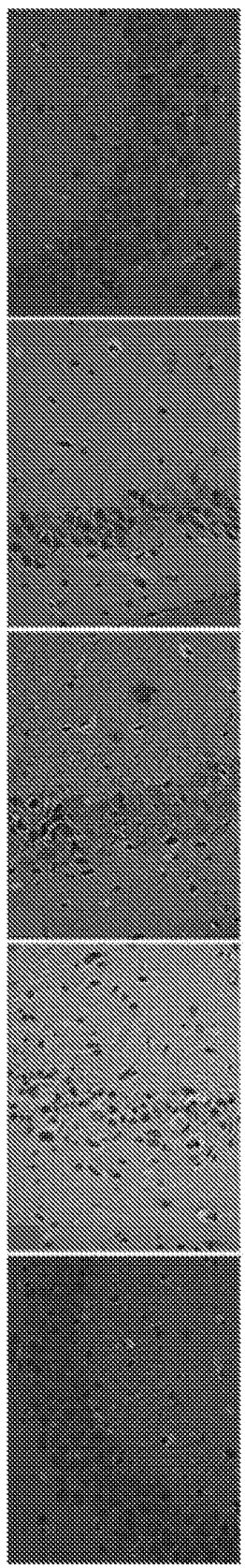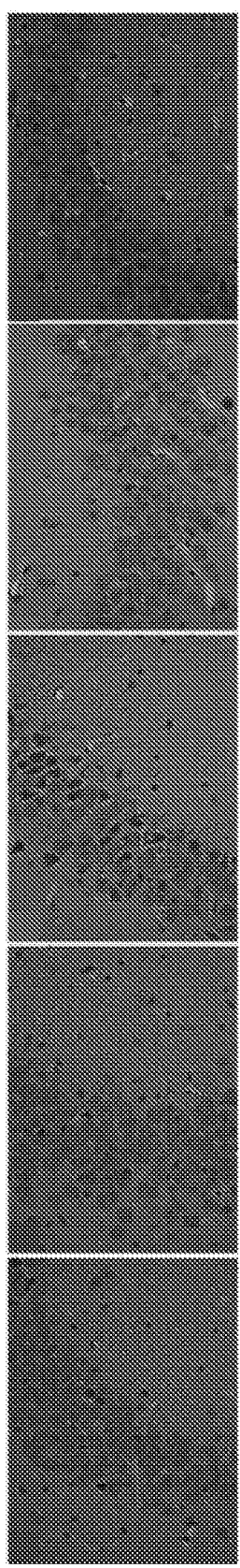
Hippocampus
FIG. 31A  FIG. 31B  FIG. 31C  FIG. 31D  FIG. 31E
FIG. 31F  FIG. 31G  FIG. 31H  FIG. 31I  FIG. 31J

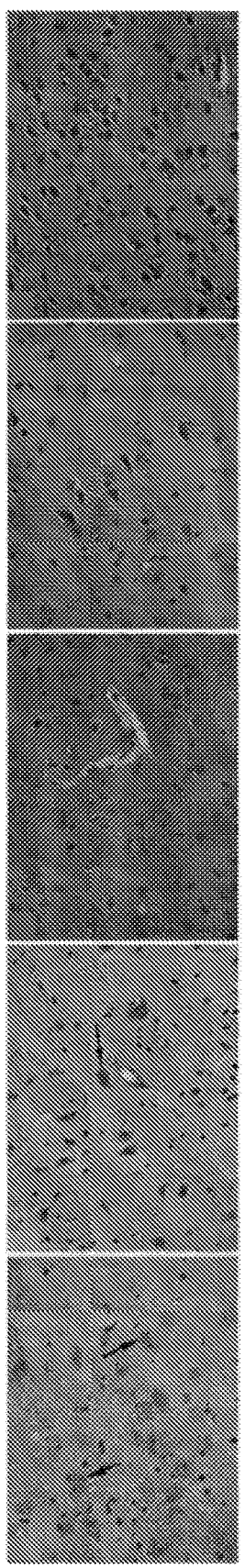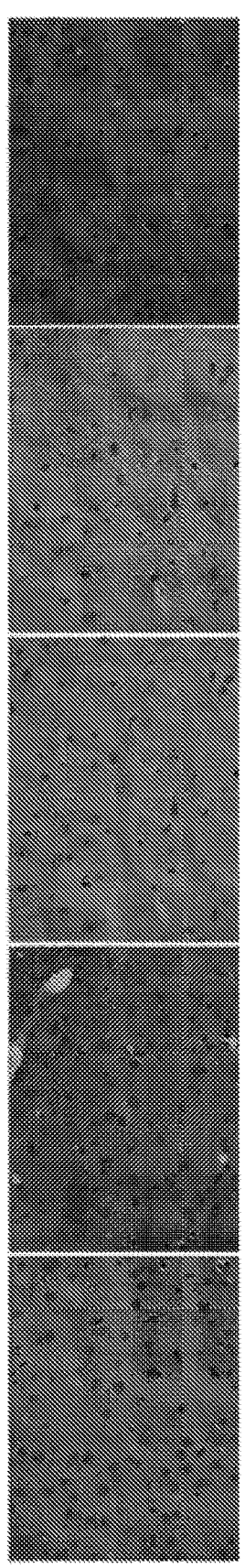
Thalamus
FIG. 31K  FIG. 31L  FIG. 31M  FIG. 31N  FIG. 31O
FIG. 31P  FIG. 31Q  FIG. 31R  FIG. 31S  FIG. 31T

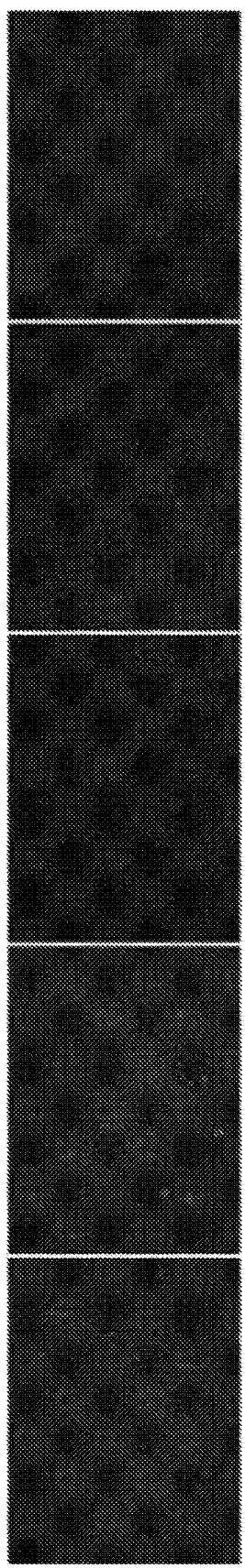
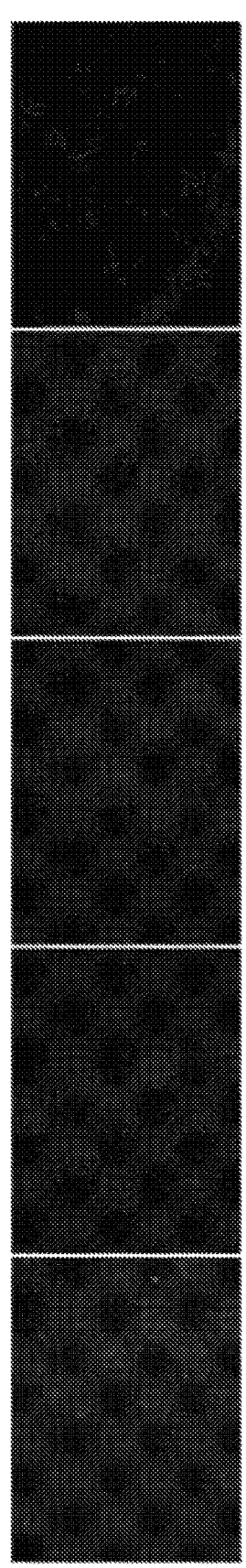
Hippocampus
FIG. 32A FIG. 32B FIG. 32C FIG. 32D FIG. 32E
FIG. 32F FIG. 32G FIG. 32H FIG. 32I FIG. 32J

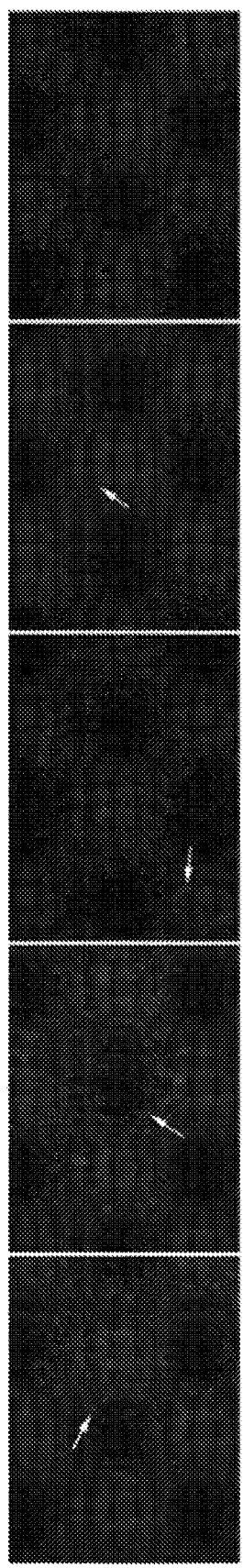
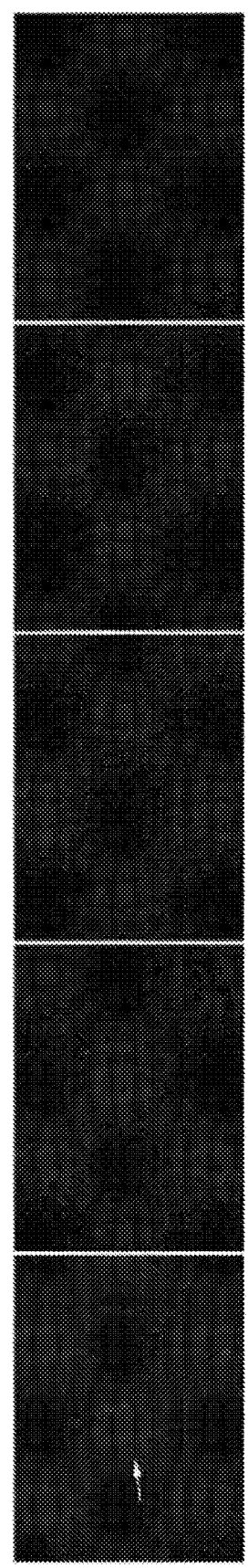
Thalamus

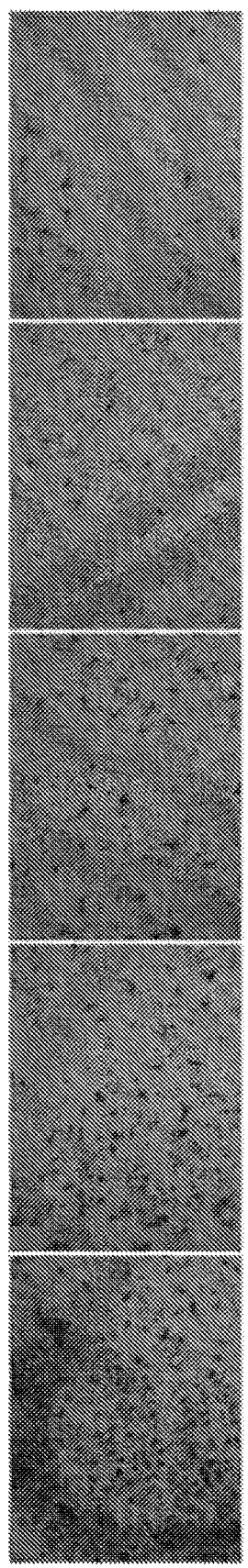
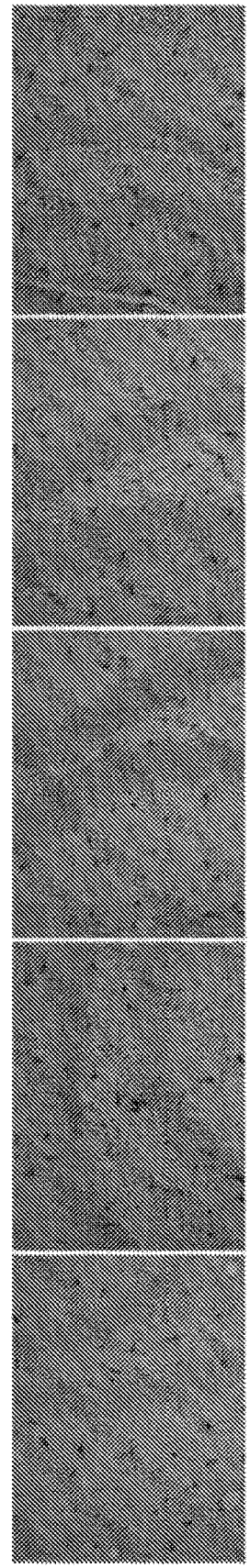
Hippocampus
FIG. 33A  FIG. 33B  FIG. 33C  FIG. 33D  FIG. 33E
FIG. 33F  FIG. 33G  FIG. 33H  FIG. 33I  FIG. 33J Thalamus

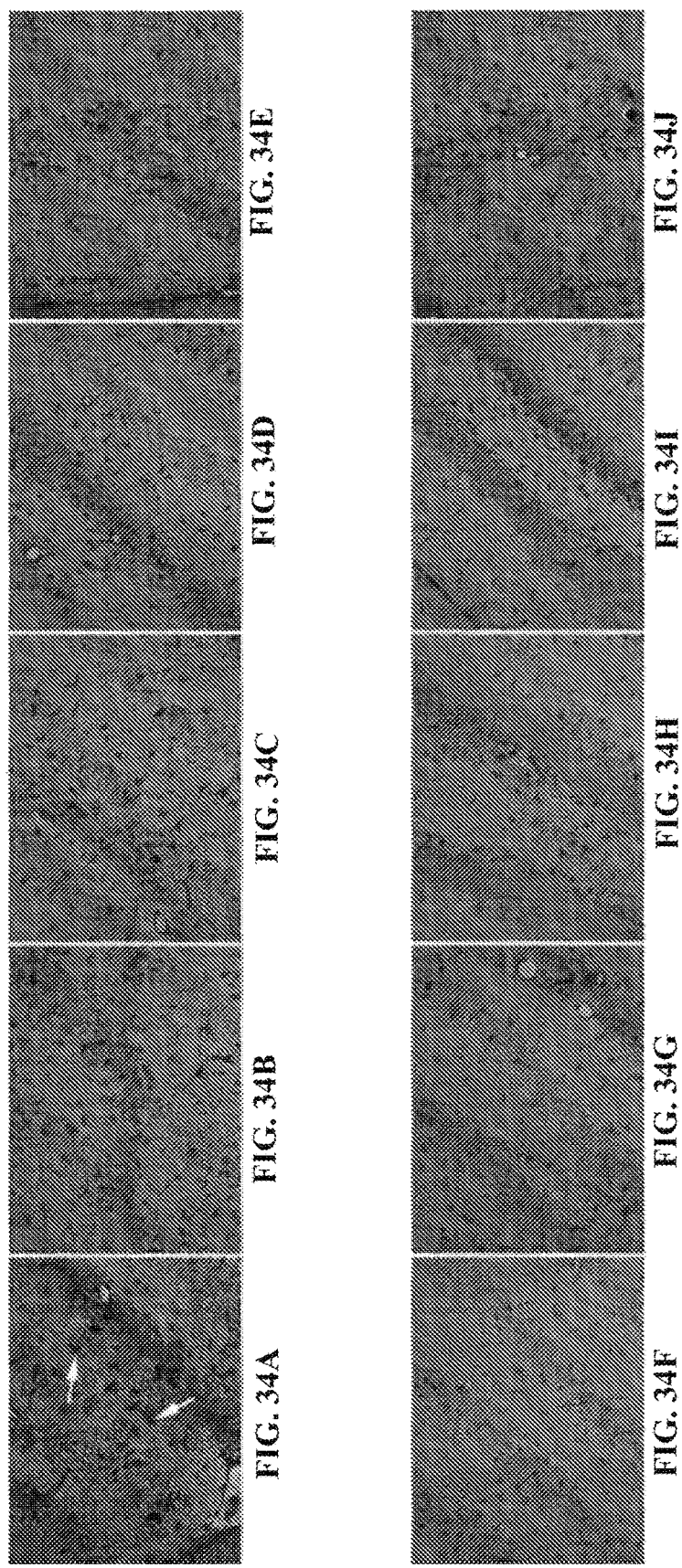

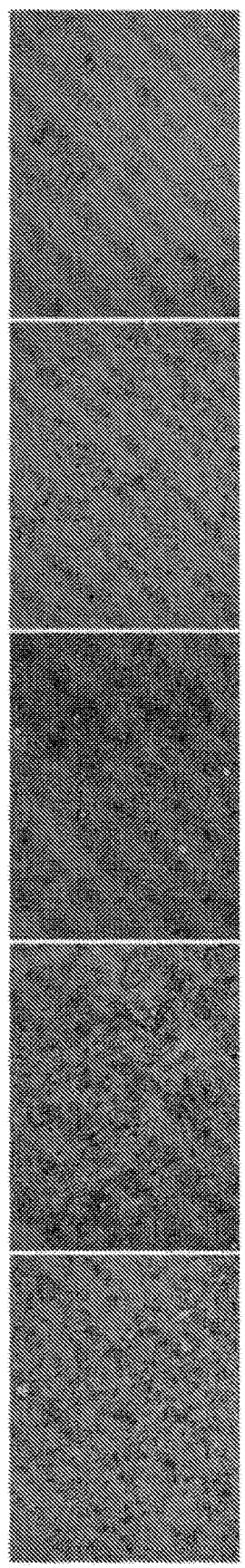
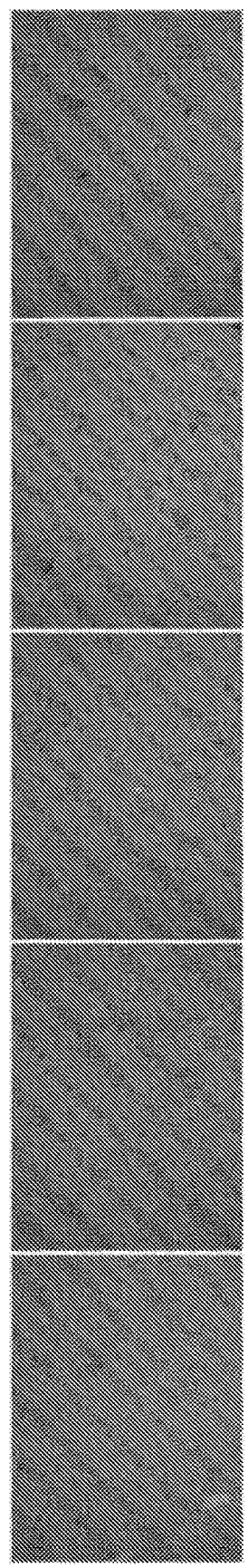
Thalamus
FIG. 34K  FIG. 34L  FIG. 34M  FIG. 34N  FIG. 34O
FIG. 34P  FIG. 34Q  FIG. 34R  FIG. 34S  FIG. 34T

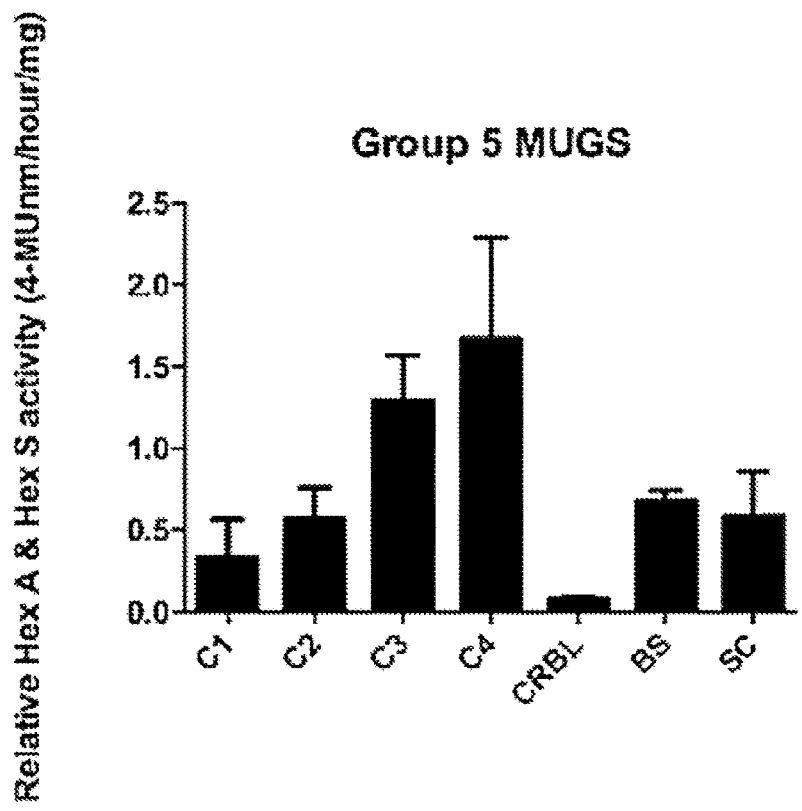
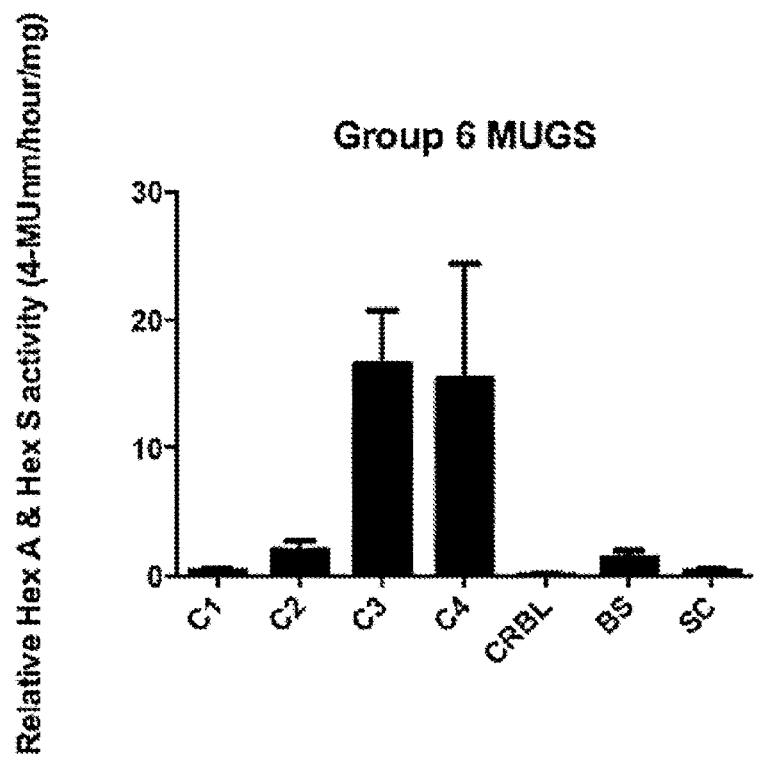
FIG. 37 (Continued)

Vd = 1.47 +/- 0.48 mL
Vi = 0.3 mL

 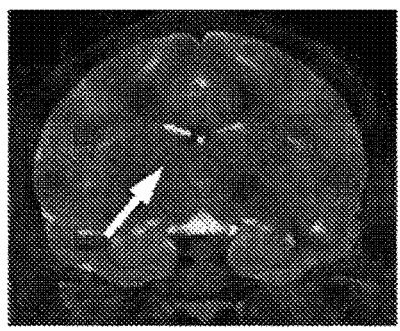 
FIG. 40A    FIG. 40B    FIG. 40C
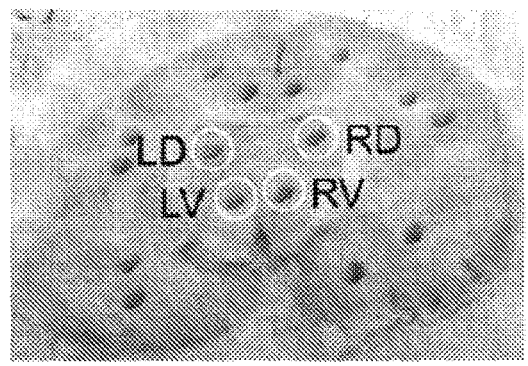
FIG. 41

 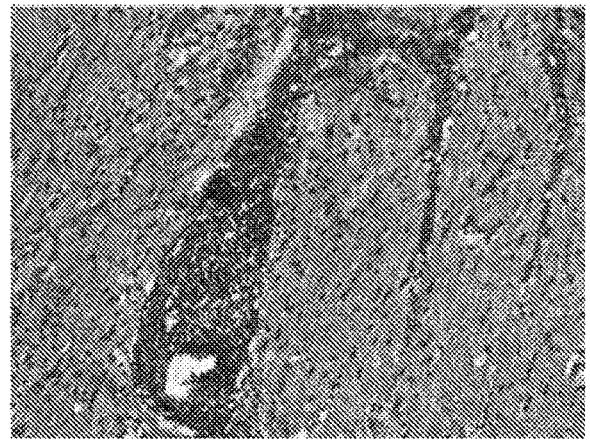
FIG. 43A  FIG. 43B
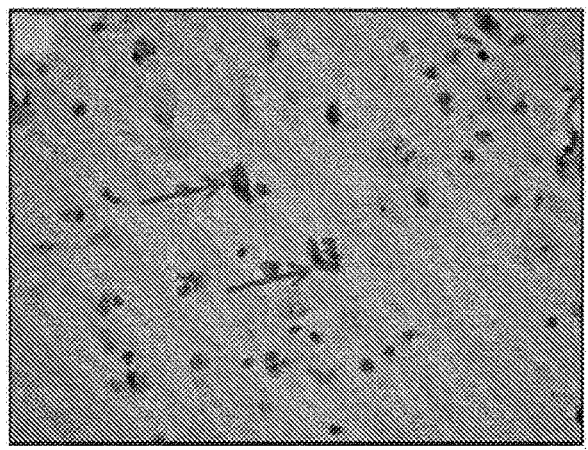 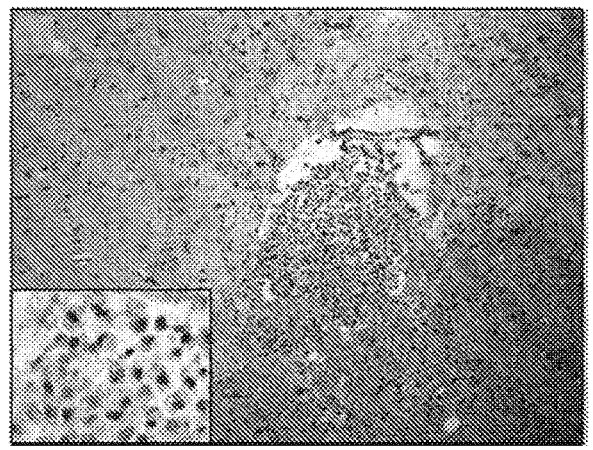
FIG. 44A  FIG. 44B

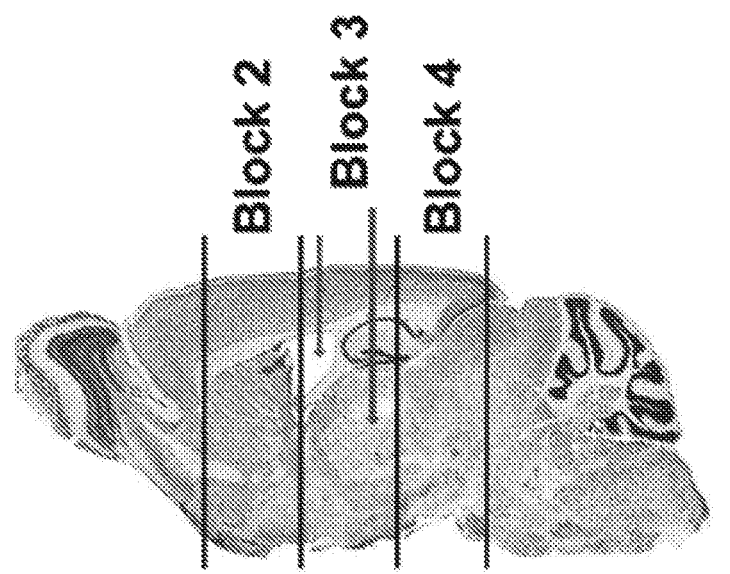
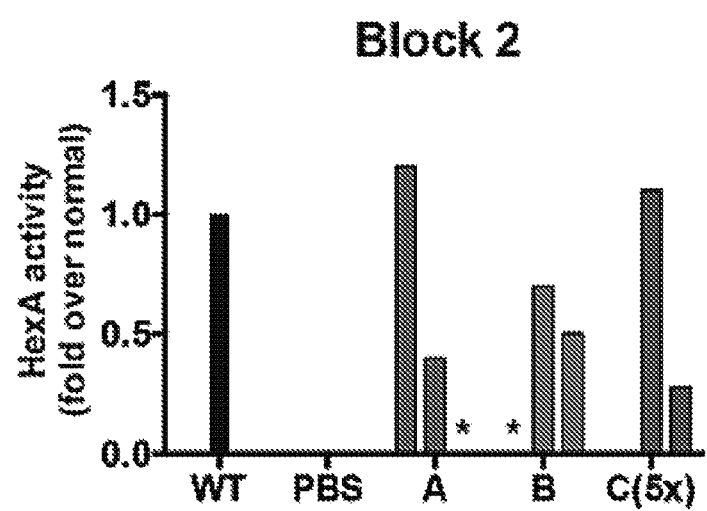
FIG. 48A

SEQUENCE LISTING

```
<160> NUMBER OF SEQ ID NOS: 15

<210> SEQ ID NO 1
<211> LENGTH: 260
<212> TYPE: DNA
<213> ORGANISM: Artificial Sequence
<220> FEATURE:
<223> OTHER INFORMATION: Synthetic Polynucleotide

<400> SEQUENCE: 1
ccacgttctg cttcactctc cccatctccc cccctcccc accccaatt ttgtatttat      60 ttatttttta attatttgt gcagcgatgg gggcgggggg ggggggcgcg cgccaggcgg    120
ggcggggcgg ggcgagggc ggggcgggc gaggcggaga ggtgcggcgg cagccaatca    180
gagcggcgcg ctccgaaagt ttccttttat ggcgaggcgg cggcggcgc ggccctataa    240 aaagcgaagc gcgcggcggg                                                260

<210> SEQ ID NO 2
<211> LENGTH: 110
<212> TYPE: DNA
<213> ORGANISM: Artificial Sequence
<220> FEATURE:
<223> OTHER INFORMATION: Synthetic Polynucleotide

<400> SEQUENCE: 2
tcgactctga cggttcacta aacgagctct gcttatatag caacctgagt gatggctccg     60
cccacgcgtg cacgtcaccg ttaccggagc aacctgacac cggctccagc                110

<210> SEQ ID NO 3
<211> LENGTH: 5964
<212> TYPE: DNA
<213> ORGANISM: Artificial Sequence
<220> FEATURE:
```

<223> OTHER INFORMATION: Synthetic Polynucleotide

<400> SEQUENCE: 3

```
agcttaaaaa ctagcgctag caacaacccc cggaggtgca gcggctggcc agagcgccca      60
ctgcctaacg gagagacccc atcgtggcgc gatcatgctc cgggtccccc tgtgtacgcc     120
gctcccgctc ctggcactgc tgcaactgct gggcgctgcg cacggcatct ataatgtcac     180
ccagaggaca tttaagctcg actacagccg ggaccgcttc ctcaaggatg gacagccatt     240
ccgatacatc tcgggaagca ttcattactt ccggataccc cgcttctact gggaggaccg     300
gctgctgaag atgaagatgg ctgggctgaa tgctatccag atgtacgtgc cctggaactt     360
ccatgaaccc caaccaggac aatatgagtt ttctggggac cgtgatgtgg agcatttcat     420
ccagctggct catgagctgg gactcctggt gatcctgagg cctgggcccc acatctgtgc     480
agagtgggac atgggggggct acctgcttg gctactagag aaacaatcta tcgttctccg     540
gtcttctgac ccagactacc ttgtagctgt ggataaatgg ctgcagtcc ttctgcccaa     600
gatgaagccc ctgctctacc agaacggagg accgatcata accgtgcagg ttgagaatga     660
gtacgggtcc tactttgcct gcgattacga ctacctacgc ttcctggtgc accgcttccg     720
ctaccatctg ggtaatgacg tcattctctt caccaccgac ggagcaagtg aaaaaatgct     780
gaagtgtggg accctgcagg acctgtacgc cacagtggat tttggaacag gcaacaatat     840
cacacaagct ttcctggtcc agaggaagtt tgaacctaaa ggacctttga tcaattctga     900
gttctatact ggctggctag accactgggg taaaccccat ccacggtga aaactaaaac     960
actggctacc tccctctata acctgcttgc ccgtggggcc aacgtgaact tgtacatgtt    1020
tataggtggg accaattttg cctattggaa tggtgccaac acgccctatg agccacagcc    1080
caccagctat gactacgacg ccccactgag cgaggctggg gacctcacta agaagtattt    1140
tgctcttcga gaagtcattc agatgtttaa agaagtccca aaggcccta tccctccgtc    1200
tacacccaaa tttgcatatg gaaaagttgc tctgagaaag ttcaagacag tggctgaagc    1260
tctgggtatc ctgtgtccca tgggccagt gaaaagcctc tatcccctga cattcactca    1320
ggtaaaacag tattttgggt atgtgctgta ccgaacaacg cttcctcaag attgcagtaa    1380
cccgaaaccc attttctctt caccttcaa tggtgtccgt gatcgggctt acgtctctgt    1440
ggacggggtc ccccaaggaa tccttgatcg aaacctcatg acagtctga acatacgggg    1500
gaaggctgga gccacgctgg acatcctggt ggagaacatg gggcgtgtga actatggcag    1560
attcatcaat gacttcaagg gtttgatttc caacatgact atcaactcca ctgtcctcac    1620
caactggacg gtcttcccac tgaacactga ggccatggta cgcaaccatc tctggggccg    1680
ggaggccagt gatgagggtc accttgacgg acgtcgacc tccaattctt cggacctcat    1740
actccccacc ttttacgtgg gcaacttctc catcccctcg ggcatccag acctgccaca    1800
ggacaccttc atccagtttc ctgggtggtc caagggtcaa gtatggatca atggctttaa    1860
cctcggccga tactggccca caatgggccc acaaaagacc ttgttcgtgc caaggaacat    1920
cctgaccact tcagccccaa acaacatcac agtgttggag ctagagtttg caccctgcag    1980
cgagggggacc ccagagctgt gtacagtaga gtttgttgac actccggtca tttcctgacg    2040
ctagcggccg cagagatcca gacatgataa gatacattga tgagtttgga caaaccacaa    2100
ctagaatgca gtgaaaaaa tgctttattt gtgaaatttg tgatgctatt gctttatttg    2160
taaccattat aagctgcaat aaacaagtta acaacaacaa ttgcattcat tttatgtttc    2220
aggttcaggg ggaggtgtgg gaggtttttt agtcgactag agctcgctga tcagcctcga    2280
```

```
ctgtgccttc tagttgccag ccatctgttg tttgcccctc cccgtgcct tccttgaccc      2340 tggaaggtgc cactcccact gtcctttcct aataaaatga ggaaattgca tcgcattgtc      2400
tgagtaggtg tcattctatt ctgggggtg gggtggggca ggacagcaag ggggaggatt      2460
gggaagacaa tagcaggcat gctggggaga gatctaggaa cccctagtga tggagttggc      2520
cactccctct ctgcgcgctc gctcgctcac tgaggccgcc cgggcaaagc ccgggcgtcg      2580
ggcgaccttt ggtcgcccgg cctcagtgag cgagcgagcg cgcagagagg gagtggccat      2640
gcagccagct ggcgtaatag cgaagaggcc cgcaccgatc gcccttccca acagttgcgt      2700
agcctgaatg gcgaatggcg cgacgcgccc tgtagcggcg cattaagcgc ggcgggtgtg      2760
gtggttacgc gcagcgtgac cgctacactt gccagcgccc tagcgcccgc tcctttcgct      2820
ttcttccctt cctttctcgc cacgttcgcc ggctttcccc gtcaagctct aaatcggggg      2880
ctccctttag ggttccgatt tagtgcttta cggcacctcg accccaaaaa acttgattag      2940
ggtgatggtt cacgtagtgg gccatcgccc tgatagacgg ttttcgccc tttgacgttg      3000 gagtccacgt tctttaatag tggactcttg ttccaaactg gaacaacact caaccctatc      3060
tcggtctatt cttttgattt ataagggatt ttgccgattt cggcctattg gttaaaaaat      3120
gagctgattt aacaaaaatt taacgcgaat tttaacaaaa tattaacgtt tacaatttcc      3180
tgatgcggta ttttctcctt acgcatctgt gcggtatttc acaccgcata tggtgcactc      3240
tcagtacaat ctgctctgat gccgcatagt taagccagcc ccgacacccg ccaacacccg      3300
ctgacgcgcc ctgacgggct tgtctgctcc cggcatccgc ttacagacaa gctgtgaccg      3360
tctccgggag ctgcatgtgt cagaggtttt caccgtcatc accgaaacgc gcgagacgaa      3420
agggcctcgt gatacgccta tttttatagg ttaatgtcat gataataatg gtttcttaga      3480
cgtcaggtgg cacttttcgg ggaaatgtgc gcggaacccc tatttgttta ttttctaaa      3540 tacattcaaa tatgtatccg ctcatgagac aataaccctg ataaatgctt caataatatt      3600
gaaaaaggaa gagtatgagt attcaacatt tccgtgtcgc ccttattccc ttttttgcgg      3660
cattttgcct tcctgttttt gctcacccag aaacgctggt gaaagtaaaa gatgctgaag      3720
atcagttggg tgcacgagtg ggttacatcg aactggatct caacagcggt aagatccttg      3780
agagttttcg ccccgaagaa cgttttccaa tgatgagcac ttttaaagtt ctgctatgtg      3840
gcgcggtatt atcccgtatt gacgccgggc aagagcaact cggtcgccgc atacactatt      3900
ctcagaatga cttggttgag tactcaccag tcacagaaaa gcatcttacg gatggcatga      3960
cagtaagaga attatgcagt gctgccataa ccatgagtga taacactgcg gccaacttac      4020
ttctgacaac gatcggagga ccgaaggagc taaccgcttt tttgcacaac atggggatc      4080 atgtaactcg ccttgatcgt tgggaaccgg agctgaatga agccatacca aacgacgagc      4140
gtgacaccac gatgcctgta gcaatggcaa caacgttgcg caaactatta actggcgaac      4200
tacttactct agcttcccgg caacaattaa tagactggat ggaggcggat aaagttgcag      4260
gaccacttct gcgctcggcc cttccggctg gctggtttat tgctgataaa tctggagccg      4320
gtgagcgtgg gtctcgcggt atcattgcag cactggggcc agatggtaag ccctcccgta      4380
tcgtagttat ctacacgacg gggagtcagg caactatgga tgaacgaaat agacagatcg      4440
ctgagatagg tgcctcactg attaagcatt ggtaactgtc agaccaagtt tactcatata      4500
tactttagat tgatttaaaa cttcattttt aatttaaaag gatctaggtg aagatccttt      4560
ttgataatct catgaccaaa atcccttaac gtgagttttc gttccactga gcgtcagacc      4620
```

```
ccgtagaaaa gatcaaagga tcttcttgag atccttttt tctgcgcgta atctgctgct     4680
tgcaaacaaa aaaaccaccg ctaccagcgg tggtttgttt gccggatcaa gagctaccaa     4740 ctcttttcc gaaggtaact ggcttcagca gagcgcagat accaaatact gtccttctag     4800
tgtagccgta gttaggccac cacttcaaga actctgtagc accgcctaca tacctcgctc     4860
tgctaatcct gttaccagtg gctgctgcca gtggcgataa gtcgtgtctt accgggttgg     4920
actcaagacg atagttaccg gataaggcgc agcggtcggg ctgaacgggg ggttcgtgca     4980
cacagcccag cttggagcga acgacctaca ccgaactgag atacctacag cgtgagcatt     5040
gagaaagcgc cacgcttccc gaagggagaa aggcggacag gtatccggta agcggcaggg     5100
tcggaacagg agagcgcacg agggagcttc caggggaaa cgcctggtat ctttatagtc     5160
ctgtcgggtt tcgccacctc tgacttgagc gtcgatttt gtgatgctcg tcagggggc     5220 ggagcctatg gaaaaacgcc agcaacgcgg cctttttacg gttcctggcc ttttgctggc     5280
cttttgctca catgttcttt cctgcgttat cccctgattc tgtggataac cgtattaccg     5340
cctttgagtg agctgatacc gctcgccgca gccgaacgac cgagcgcagc gagtcagtga     5400
gcgaggaagc ggaagagcgc ccaatacgca aaccgcctct ccccgcgcgt tggccgattc     5460
attaatgcag ctgggctgca gggggggggg ggggggggtg gggggggggg gggggggttg     5520
gccactccct ctctgcgcgc tcgctcgctc actgaggccg ggcgaccaaa ggtcgcccga     5580
cgcccgggct ttgcccgggc ggcctcagtg agcgagcgag cgcgcagaga gggagtggcc     5640
aactccatca ctaggggttc ctagatctga attctctagt ccacgttctg cttcactctc     5700
cccatctccc ccccctcccc accccccaatt ttgtatttat ttatttttta attattttgt     5760
gcagcgatgg gggcggggg gggggcgcg cgccaggcgg ggcggggcgg ggcgaggggc     5820 ggggcgggc gaggcggaga ggtgcggcgg cagccaatca gagcggcgcg ctccgaaagt     5880 ttcctttat ggcgaggcgg cggcggcggc ggccctataa aaagcgaagc gcgcggcggg     5940
gggccgcggg ccgatccacc ggta                                            5964

<210> SEQ ID NO 4
<211> LENGTH: 594
<212> TYPE: DNA
<213> ORGANISM: Artificial Sequence
<220> FEATURE:
<223> OTHER INFORMATION: Synthetic Polynucleotide

<400> SEQUENCE: 4
ccacgttctg cttcactctc cccatctccc ccccctcccc accccaatt ttgtatttat       60 ttatttttta attattttgt gcagcgatgg gggcggggg gggggcgcg cgccaggcgg      120 ggcggggcgg ggcgaggggc ggggcgggc gaggcggaga ggtgcggcgg cagccaatca      180
gagcggcgcg ctccgaaagt ttcctttat ggcgaggcgg cggcggcggc ggccctataa      240
aaagcgaagc gcgcgcggg gggcgcgggg gagtcgctgc gacgctgcct tcgccccgtg      300
ccccgctccg ccgccgcctc gcgccgcccg ccccggctct gactgaccgc gttactccca      360
caggtgagcg gcgggacgg cccttctcct ccgggctgta attagcgctt ggtttaatga      420
cggcttgttt cttttctgtg gctgcgtgaa agccttgagg ggctccggga gctagagcct      480
ctgctaacca tgttcatgcc ttcttctttt tcctacagct cctgggcaac gtgctggtta      540
ttgtgctgtc tcatcatttt ggcaaagaat tcctcgaaga tccgaagggg ttca            594

<210> SEQ ID NO 5
<211> LENGTH: 408
```

```
<212> TYPE: DNA
<213> ORGANISM: Artificial Sequence
<220> FEATURE:
<223> OTHER INFORMATION: Synthetic Polynucleotide

<400> SEQUENCE: 5
ctggagccgg tgtcaggttg ctccggtaac ggtgacgtgc acgcgtgggc ggagccatca      60
cgcaggttgc tatataagca gagctcgttt agtgaaccgt cagaggagtc gctgcgacgc     120
tgccttcgcc ccgtgccccg ctccgccgcc gcctcgcgcc gcccgccccg gctctgactg     180
accgcgttac tcccacaggt gagcgggcgg acggcccttt ctcctccggg ctgtaattag     240
cgcttggttt aatgacggct tgtttctttt ctgtggctgc gtgaaagcct tgagggggctc    300 cgggagctag agcctctgct aaccatgttc atgccttctt cttttttccta cagctcctgg   360 gcaacgtgct ggttattgtg ctgtctcatc attttggcaa agaattcc                 408

<210> SEQ ID NO 6
<211> LENGTH: 5688
<212> TYPE: DNA
<213> ORGANISM: Artificial Sequence
<220> FEATURE:
<223> OTHER INFORMATION: Synthetic Polynucleotide

<400> SEQUENCE: 6
ttggccactc cctctctgcg cgctcgctcg ctcactgagg ccgggcgacc aaaggtcgcc      60
cgacgcccgg gctttgcccg gcggcctcca gtgagcgagc gagcgcgcag agagggagtg    120
gccaactcca tcactagggg ttcctagatc tgaattcggt accctggagc cggtgtcagg   180
ttgctccggt aacggtgacg tgcacgcgtg ggcggagcca tcacgcaggt tgctatataa     240
gcagagctcg tttagtgaac cgtcagagga gtcgctgcga cgctgccttc gccccgtgcc    300
ccgctccgcc gccgcctcgc gccgcccgcc ccggctctga ctgaccgcgt tactcccaca    360
ggtgagcggg cgggacggcc cttctcctcc gggctgtaat tagcgcttgg tttaatgacg    420
gcttgtttct tttctgtggc tgcgtgaaag ccttgagggg ctccgggagc tagagcctct    480
gctaaccatg ttcatgcctt cttctttttc ctacagctcc tgggcaacgt gctggttatt    540
gtgctgtctc atcattttgg caaagaattc ctcgaagatc cgaaggggtt caagcttaaa    600
aactagtgga gcaccatggc aagctccagg ctttggtttt cgctgctgct ggcggcagcg    660
ttcgcaggac gggcgaccgc cctctggccc tggcctcaga acatccaaac ctccgaccag    720
cgctacgtcc tttatccgaa caactttcaa ttccagtacg atatcagctc gccgcgcag    780 cctggctgct cagtcctcga cgaggccttc agcgctatc gtgacctgct tttcggttcc    840
gggtcttggc ccgtccttac cgcacagga aaacggcata cacctgagaa gaatgtgttg    900
gttgtctctg tagtcacacc tggatgtaac cagcttccta ctttggagtc ggtagagaat    960
tataccctga ccataaatga tgaccagtgt ttactcctct ctgagactgt ctggggagct   1020
ctccgaggtc tggagacttt tagccagctt gtttggaaat ctgctgaggg cacattcttt   1080
atcaacaaga ctgagatcga ggactttccc cgctttcctc accgggggctt gctgttggat  1140 acatctcgcc attacctacc actctctagc atcctggaca cactggatgt catggcgtac   1200
aataaattga acgtgttcca ctggcatctg gtagatgatc cttccttccc atatgagagc   1260 ttcactttc cagagctcat gagaaagggg tcctacaacc tgtcaccca catttacaca    1320 gcacaggatg tgaaggaggt cattgaatac gcacggctcc ggggtatccg tgtgcttgca   1380
gagtttgaca ctcctggcca cactttgtct tggggaccag gtatccctgg attactgact  1440
```

```
ccttgctact ctgggtctga gccctctggc acctttggac cagtgaatcc cagtctcaac      1500
aatacctatg agttcatgag cacattcttc ttggagatca gctctgtctt cccagatttt      1560
tatcttcatc ttggaggaga tgaggttgat ttcacctgct ggaagtccaa cccagatatc      1620
caagacttta tgaggaagaa aggcttcggt gaggacttca agcagttgga gtccttctac      1680
atccagacgc tgctggacat cgtctcttct tatggcaagg gctatgtggt gtggcaggag      1740
gtgtttgata taaagtaaa gattcggcca gacacaatca tacaggtgtg gcagaagag       1800
attccagtga actatatgaa ggagctggaa ctggtcacca aggccggctt ccgggccctt      1860
ctctccgccc cctggtacct gaaccgtata tcctacggcc ctgactggaa ggatttctac      1920
atagtggaac ccctggcatt tgaaggtacc cctgagcaga aggctctcgt gattggtgga      1980
gaggcttgta tgtggggaga atatgtggac aacacaaacc tggtcccag gctctggccc       2040
agagcagggg ctgttgccga aaggctgtgg agcaacaagt tgacatctga cctgacattt      2100
gcctatgaac gtttgtcaca cttccgctgt gagttgctga ggcgaggtgt ccaggcccaa      2160
cccctccatg taggctactg tgagcaggag tttgaacaga cctgactcga gctagcggcc      2220
gcagagatcc agacatgata agatacattg atgagtttgg acaaaccaca actagaatgc      2280
agtgaaaaaa atgctttatt tgtgaaattt gtgatgctat tgctttatt gtaaccatta       2340
taagctgcaa taaacaagtt aacaacaaca attgcattca ttttatgttt caggttcagg      2400
gggaggtgtg ggaggttttt tagtcgacta gagctcgctg atcagcctcg actgtgcctt      2460
ctagttgcca gccatctgtt gtttgccct ccccgtgcc ttccttgacc ctggaaggtg         2520
ccactcccac tgtcctttcc taataaaatg aggaaattgc atcgcattgt ctgagtaggt      2580
gtcattctat tctggggggt ggggtggggc aggacagcaa gggggaggat tgggaagaca      2640
atagcaggca tgctggggag agatctagga accctagtg atggagttgg ccactccctc       2700
tctgcgcgct cgctcgctca ctgaggccgc ccgggcaaag cccgggcgtc gggcgacctt      2760
tggtcgcccg gcctcagtga gcgagcgagc gcgcagagag ggagtggcca tgcagccagc      2820
tggcgtaata gcgaagaggc ccgcaccgat cgcccttccc aacagttgcg tagcctgaat      2880
ggcgaatggc gcgacgcgcc ctgtagcggc gcattaagcg cggcgggtgt ggtggttacg      2940
cgcagcgtga ccgctacact tgccagcgcc ctagcgcccg ctccttccgc tttcttccct      3000
tcctttctcg ccacgttcgc cggctttccc cgtcaagctc taaatcgggg gctcccttta      3060
gggttccgat ttagtgcttt acggcacctc gaccccaaaa aacttgatta gggtgatggt      3120
tcacgtagtg ggccatcgcc ctgatagacg ttttttcgcc ctttgacgtt ggagtccacg      3180
ttctttaata gtggactctt gttccaaact ggaacaacac tcaaccctat ctcggtctat      3240
tcttttgatt tataagggat tttgccgatt tcggcctatt ggttaaaaaa tgagctgatt      3300
taacaaaaat ttaacgcgaa ttttaacaaa atattaacgt ttacaatttc ctgatgcggt      3360
attttctcct tacgcatctg tgcggtattt cacaccgcat atggtgcact ctcagtacaa      3420
tctgctctga tgccgcatag ttaagccagc cccgacaccc gccaacaccc gctgacgcgc      3480
cctgacgggc ttgtctgctc ccggcatccg cttacagaca agctgtgacc gtctccggga      3540
gctgcatgtg tcagaggttt tcaccgtcat caccgaaacg cgcgagacga aagggcctcg      3600
tgatacgcct atttttatag gttaatgtca tgataataat ggtttcttag acgtcaggtg      3660
gcacttttcg gggaaatgtg cgcggaaccc ctatttgttt attttctaaa tacattcaa       3720
atatgtatcc gctcatgaga caataaccct gataaatgct tcaataatat tgaaaaagga      3780
agagtatgag tattcaacat ttccgtgtcg cccttattcc cttttttgcg gcattttgcc      3840
```

-continued

```
ttcctgtttt tgctcaccca gaaacgctgg tgaaagtaaa agatgctgaa gatcagttgg    3900
gtgcacgagt gggttacatc gaactggatc tcaacagcgg taagatcctt gagagttttc    3960
gccccgaaga acgttttcca atgatgagca cttttaaagt tctgctatgt ggcgcggtat    4020
tatcccgtat tgacgccggg caagagcaac tcggtcgccg catacactat tctcagaatg    4080
acttggttga gtactcacca gtcacagaaa agcatcttac ggatggcatg acagtaagag    4140
aattatgcag tgctgccata accatgagtg ataacactgc ggccaactta cttctgacaa    4200
cgatcggagg accgaaggag ctaaccgctt ttttgcacaa catggggat catgtaactc    4260 gccttgatcg ttgggaaccg gagctgaatg aagccatacc aaacgacgag cgtgacacca    4320
cgatgcctgt agcaatggca acaacgttgc gcaaactatt aactggcgaa ctacttactc    4380
tagcttcccg gcaacaatta atagactgga tggaggcgga taaagttgca ggaccacttc    4440
tgcgctcggc ccttccggct ggctggttta ttgctgataa atctggagcc ggtgagcgtg    4500
ggtctcgcgg tatcattgca gcactgggc cagatggtaa gccctcccgt atcgtagtta    4560
tctacacgac ggggagtcag gcaactatgg atgaacgaaa tagacagatc gctgagatag    4620
gtgcctcact gattaagcat tggtaactgt cagaccaagt ttactcatat atactttaga    4680
ttgatttaaa acttcatttt taatttaaaa ggatctaggt gaagatcctt tttgataatc    4740
tcatgaccaa aatcccttaa cgtgagtttt cgttccactg agcgtcagac cccgtagaaa    4800
agatcaaagg atcttcttga tccttttttt ttctgcgcgt aatctgctgc ttgcaaacaa    4860
aaaaaccacc gctaccagcg gtggtttgtt tgccggatca agagctacca actctttttc    4920
cgaaggtaac tggcttcagc agagcgcaga taccaaatac tgtccttcta gtgtagccgt    4980
agttaggcca ccacttcaag aactctgtag caccgcctac atacctcgct ctgctaatcc    5040
tgttaccagt ggctgctgcc agtggcgata agtcgtgtct taccgggttg gactcaagac    5100
gatagttacc ggataaggcg cagcggtcgg gctgaacggg gggttcgtgc acacagccca    5160
gcttggagcg aacgacctac accgaactga gatacctaca gcgtgagcat tgagaaagcg    5220
ccacgcttcc cgaagggaga aaggcggaca ggtatccggt aagcggcagg gtcggaacag    5280
gagagcgcac gagggagctt ccagggggaa acgcctggta tctttatagt cctgtcgggt    5340
ttcgccacct ctgacttgag cgtcgatttt tgtgatgctc gtcagggggg cggagcctat    5400
ggaaaaacgc cagcaacgcg gcctttttac ggttcctggc cttttgctgg ccttttgctc    5460
acatgttctt tcctgcgtta tcccctgatt ctgtggataa ccgtattacc gcctttgagt    5520
gagctgatac cgctcgccgc agccgaacga ccgagcgcag cgagtcagtg agcgaggaag    5580
cggaagagcg cccaatacgc aaaccgcctc tccccgcgcg ttggccgatt cattaatgca    5640
gctgggctgc agggggggg gggggggggt gggggggggg ggggggg        5688
```

<210> SEQ ID NO 7
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 7

```
aaacgtctca ctagtccgcg gaattc                                           26
```

<210> SEQ ID NO 8
<211> LENGTH: 26
<212> TYPE: DNA

<213> ORGANISM: Artificial Sequence
<220> FEATURE:
<223> OTHER INFORMATION: Synthetic Polynucleotide

<400> SEQUENCE: 8
aaacgtctca ctgagaattg atcaaa    26

<210> SEQ ID NO 9
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 9
aaaggtctcc ggccgctagc gtcag    25

<210> SEQ ID NO 10
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 10
aaaggtctca tcagttctat actggc    26

<210> SEQ ID NO 11
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 11 agcattttttt tcactgcatt ctagttgtgg tttgtc    36

<210> SEQ ID NO 12
<211> LENGTH: 4260
<212> TYPE: DNA
<213> ORGANISM: Artificial Sequence
<220> FEATURE:
<223> OTHER INFORMATION: Synthetic Polynucleotide

<400> SEQUENCE: 12
ttggccactc cctctctgcg cgctcgctcg ctcactgagg ccgggcgacc aaaggtcgcc    60
cgacgcccgg gctttgcccg gcggcctca gtgagcgagc gagcgcgcag agagggagtg    120
gccaactcca tcactagggg ttcctagatc tgaattcggt accgagggcc ctgcgtatga    180
gtgcaagtgg gttttaggac caggatgagg cggggtgggg gtgcctacct gacgaccgac    240
cccgacccac tggacaagca cccaaccccc attccccaaa ttgcgcatcc cctatcagag    300
agggggaggg gaaacaggat gcggcgaggc gcgtgcgcac tgccagcttc agcaccgcgg    360
acagtgcctt cgccccccgcc tggcggcgcg cgccaccgcc gcctcagcac tgaaggcgcg    420
ctgacgtcac tcgccggtcc cccgcaaact ccccttcccg gccaccttgg tcgcgtccgc    480
gccgccgccg gccagccgg accgcaccac gcgaggcgcg agataggggg gcacgggcgc    540
gaccatctgc gctgcggcgc cggcgactca gcgctgcctc agtctgcggt gggcagcgga    600
ggagtcgtgt cgtgcctgag agcgcagtcg agaactagat taattaaacc ggtaagcttg    660
ccaccatggt gagcaaggggc gaggagctgt tcaccggggt ggtgcccatc ctggtcgagc    720
tggacggcga cgtaaacggc cacaagttca gcgtgtccgg cgagggcgag ggcgatgcca    780

```
cctacggcaa gctgaccctg aagttcatct gcaccaccgg caagctgccc gtgccctggc        840
ccaccctcgt gaccaccctg acctacggcg tgcagtgctt cagccgctac cccgaccaca        900
tgaagcagca cgacttcttc aagtccgcca tgcccgaagg ctacgtccag gagcgcacca        960
tcttcttcaa ggacgacggc aactacaaga cccgcgccga ggtgaagttc gagggcgaca       1020
ccctggtgaa ccgcatcgag ctgaagggca tcgacttcaa ggaggacggc aacatcctgg       1080
ggcacaagct ggagtacaac tacaacagcc acaacgtcta tatcatggcc gacaagcaga       1140
agaacggcat caaggtgaac ttcaagatcc gccacaacat cgaggacggc agcgtgcagc       1200
tcgccgacca ctaccagcag aacaccccca tcggcgacgg ccccgtgctg ctgcccgaca       1260
accactacct gagcacccag tccgccctga gcaaagaccc caacgagaag cgcgatcaca       1320
tggtcctgct ggagttcgtg accgccgcgg gatcactct cggcatggac gagctgtaca       1380
agtccggact cagatcctac tgaactagtc ggcgacggtg ctagcgtcga ccagtggatc       1440
ctggaggctt gctgaaggct gtatgctgat gaacatggaa tccatgcagg ttttggccac       1500
tgactgacct gcatggtcca tgttcatcag gacacaaggc ctgttactag cactcacatg       1560
gaacaaatgg cccagatcct ggaggcttgc tgaaggctgt atgctgatga acatggaatc       1620
catgcaggtt ttggccactg actgacctgc atggtccatg ttcatcagga cacaaggcct       1680
gttactagca ctcacatgga acaaatggcc cagatctggc cgcactcgaa aacgggcccg       1740
cggccgcaga gatccagaca tgataagata cattgatgag tttggacaaa ccacaactag       1800
aatgcagtga aaaaaatgct ttatttgtga aatttgtgat gctattgctt tatttgtaac       1860
cattataagc tgcaataaac aagttaacaa caacaattgc attcatttta tgtttcaggt       1920
tcagggggag gtgtgggagg ttttttagtc gacaacatat cctggtgtgg agtaggggac       1980
gctgctctga cagaggctcg ggggcctgag ctggctctgt gagctgggga ggaggcagac       2040
agccaggcct tgtctgcaag cagacctggc agcattgggc tggccgcccc cagggcctc       2100 ctcttcatgc ccagtgaatg actcaccttg gcacagacac aatgttcggg gtgggcacag       2160
tgcctgcttc ccgccgcacc ccagccccc tcaaatgcct tccgagaagc ccattgagca       2220
gggggcttgc attgcacccc agcctgacag cctggcatct tgggataaaa gcagcacagc       2280
cccctagggg ctgcccttgc tgtgtggcgc caccggcggt ggagaacaag gctctattca       2340
gcctgtgccc aggaaagggg atcagggat gcccaggcat ggacagtggg tggcaggggg       2400
ggagaggagg gctgtctgct tcccagaagt ccaaggacac aaatgggtga ggggagagct       2460
ctccccatag ctgggctgcg gcccaacccc accccctcag gctatgccag ggggtgttgc       2520
caggggcacc cgggcatcgc cagtctagcc cactccttca taaagccctc gcatcccagg       2580
agcgagcaga gccagagcag gttggagagg agacgcatca cctccgctgc tgcttggtc       2640 gtgaggcact gggcaggtaa gtatcaaggt tacaagacag gtttaaggag accaatagaa       2700
actgggcttg tcgatccac ggcgacggtg ctagcgtcga ccagtggatc ctggaggctt       2760
gctgaaggct gtatgctgat gaacatggaa tccatgcagg ttttggccac tgactgacct       2820
gcatggtcca tgttcatcag gacacaaggc ctgttactag cactcacatg gaacaaatgg       2880
cccagatcct ggaggcttgc tgaaggctgt atgctgatga acatggaatc catgcaggtt       2940
ttggccactg actgacctgc atggtccatg ttcatcagga cacaaggcct gttactagca       3000
ctcacatgga acaaatggcc cagatctggc cgcactcgaa aacgggccca tcgatagaga       3060
cagagaagac tcttgcgttt ctgataggca cctattggtc ttactgacat ccactttgcc       3120
```

| | |
|---|---|
| tttctctcca caggtgtcca ctcgctagcg ccaccatggt gagcaagggc gaggaggata | 3180 |
| acatggccat catcaaggag ttcatgcgct tcaaggtgca catggagggc tccgtgaacg | 3240 |
| gccacgagtt cgagatcgag ggcgagggcg agggccgccc ctacgagggc acccagaccg | 3300 |
| ccaagctgaa ggtgaccaag ggtggcccc tgcccttcgc ctgggacatc ctgtcccctc | 3360 |
| agttcatgta cggctccaag gcctacgtga agcaccccgc cgacatcccc gactacttga | 3420 |
| agctgtcctt ccccgagggc ttcaagtggg agcgcgtgat gaacttcgag gacggcggcg | 3480 |
| tggtgaccgt gacccaggac tcctccctgc aggacggcga gttcatctac aaggtgaagc | 3540 |
| tgcgcggcac caacttcccc tccgacggcc ccgtaatgca gaagaagacc atgggctggg | 3600 |
| aggcctcctc cgagcggatg taccccgagg acggcgccct gaagggcgag atcaagcaga | 3660 |
| ggctgaagct gaaggacggc ggccactacg acgctgaggt caagaccacc tacaaggcca | 3720 |
| agaagcccgt gcagctgccc ggcgcctaca acgtcaacat caagttggac atcacctccc | 3780 |
| acaacgagga ctacaccatc gtggaacagt acgaacgcgc cgagggccgc cactccaccg | 3840 |
| gcggcatgga cgagctgtac aagtgacgta cggtcgacta gagctcgctg atcagcctcg | 3900 |
| actgtgcctt ctagttgcca gccatctgtt gtttgcccct cccccgtgcc ttccttgacc | 3960 |
| ctggaaggtg ccactcccac tgtcctttcc taataaaatg aggaaattgc atcgcattgt | 4020 |
| ctgagtaggt gtcattctat tctgggggt ggggtgggc aggacagcaa gggggaggat | 4080 |
| tgggaagaca atagcaggca tgctgggag agatctagga acccctagtg atggagttgg | 4140 |
| ccactccctc tctgcgcgct cgctcgctca ctgaggccgc ccgggcaaag cccgggcgtc | 4200 |
| gggcgacctt tggtcgcccg gcctcagtga gcgagcgagc gcgcagagag ggagtggcca | 4260 |

<210> SEQ ID NO 13
<211> LENGTH: 470
<212> TYPE: DNA
<213> ORGANISM: Artificial Sequence
<220> FEATURE:
<223> OTHER INFORMATION: Synthetic Polynucleotide

<400> SEQUENCE: 13

| | |
|---|---|
| gagggccctg cgtatgagtg caagtgggtt ttaggaccag gatgaggcgg ggtgggggtg | 60 |
| cctacctgac gaccgacccc gacccactgg acaagcaccc aaccccatt ccccaaattg | 120 |
| cgcatcccct atcagagagg gggagggga acaggatgcg gcgaggcgcg tgcgcactgc | 180 |
| cagcttcagc accgcggaca gtgccttcgc ccccgcctgg cggcgcgcgc caccgccgcc | 240 |
| tcagcactga aggcgcgctg acgtcactcg ccggtccccc gcaaactccc cttcccggcc | 300 |
| accttggtcg cgtccgcgcc gccgccggcc cagccggacc gcaccacgcg aggcgcgaga | 360 |
| taggggggca cgggcgcgac catctgcgct gcggcgccgg cgactcagcg ctgcctcagt | 420 |
| ctgcggtggg cagcggagga gtcgtgtcgt gcctgagagc gcagtcgaga | 470 |

<210> SEQ ID NO 14
<211> LENGTH: 681
<212> TYPE: DNA
<213> ORGANISM: Artificial Sequence
<220> FEATURE:
<223> OTHER INFORMATION: Synthetic Polynucleotide

<400> SEQUENCE: 14

| | |
|---|---|
| aacatatcct ggtgtggagt aggggacgct gctctgacag aggctcgggg gcctgagctg | 60 |
| gctctgtgag ctggggagga ggcagacagc caggccttgt ctgcaagcag acctggcagc | 120 |
| attgggctgg ccgcccccca gggcctcctc ttcatgccca gtgaatgact caccttggca | 180 |

```
cagacacaat gttcggggtg ggcacagtgc ctgcttcccg ccgcacccca gcccccctca    240
aatgccttcc gagaagccca ttgagcaggg ggcttgcatt gcaccccagc ctgacagcct    300
ggcatcttgg gataaaagca gcacagcccc ctaggggctg cccttgctgt gtggcgccac    360
cggcggtgga gaacaaggct ctattcagcc tgtgcccagg aaaggggatc aggggatgcc    420
caggcatgga cagtgggtgg caggggggga gaggagggct gtctgcttcc cagaagtcca    480
aggacacaaa tgggtgaggg gagagctctc cccatagctg ggctgcggcc caacccacc     540 ccctcaggct atgccagggg gtgttgccag gggcacccgg gcatcgccag tctagcccac    600
tccttcataa agccctcgca tcccaggagc gagcagagcc agagcaggtt ggagaggaga    660
cgcatcacct ccgctgctcg c                                              681

<210> SEQ ID NO 15
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 15
caggacacaa ggcctgttac tagcactcac atggaacaaa tggcc                    45
```

MODULATION OF AAV VECTOR TRANSGENE EXPRESSION

RELATED APPLICATIONS

This application is a National Stage Application of PCT/US2016/028367, filed Apr. 20, 2016 entitled, "MODULATION OF AAV VECTOR TRANSGENE EXPRESSION", which claims the benefit under 35 U.S.C. § 119(e) of U.S. Provisional Application 62/151,988, filed Apr. 23, 2015, entitled "AAV VECTORS FOR EXPRESSION OF LYSOSOMAL ENZYMES", the entire contents of each application which are incorporated herein by reference.

FEDERALLY SPONSORED RESEARCH

This invention was made with government support under grant number HD060576 awarded by National Institutes of Health. The government has certain rights in the invention.

FIELD OF THE INVENTION

The disclosure in some aspects provides recombinant adeno-associated viruses (rAAVs), compositions and kits useful for the treatment of lysosomal storage disorders. In some embodiments, the rAAVs comprise artificial genetic regulatory elements that modulate transgene expression.

BACKGROUND OF INVENTION

Adeno associated Virus (AAV) is a small and helper dependent virus. It was discovered in the 1960s as a contaminant in adenovirus (a cold causing virus) preparations. Its growth in cells is dependent on the presence of adenovirus and, therefore, it was named as adeno-associated virus. AAV vectors have emerged as an effective platform for in vivo gene transfer. However, a need remains for new AAV vectors for gene delivery.

SUMMARY OF INVENTION

Aspects of the disclosure relate to recombinant AAV vectors for gene delivery. Some current AAV vectors deliver high levels of gene expression that result in adverse events (e.g., cytotoxicity) in a subject. The disclosure is based, in part, on the recognition that engineered regulatory elements can modulate transgene expression levels to provide therapeutic amounts of transgene without the induction of adverse events.

In some aspects the disclosure provides a recombinant AAV (rAAV) comprising a capsid containing a nucleic acid comprising a hybrid promoter operably linked to a transgene encoding a lysosomal storage disorder-associated protein. In some embodiments, the hybrid promoter comprises a chicken beta-actin (CB) promoter. In some embodiments, the hybrid promoter comprises a cytomegalovirus (CMV) enhancer element. In some embodiments, the rAAV further comprises a woodchuck hepatitis virus posttranscriptional regulatory element (WPRE). In some embodiments, the hybrid promoter comprises a CB promoter and a CMV enhancer element, wherein the CB promoter and the CMV element are fused together to form the hybrid promoter. In some embodiments, the transgene is located in between the hybrid promoter and the WPRE. In some embodiments, the hybrid promoter does not contain an intronic sequence.

In some aspects the disclosure provides a recombinant AAV (rAAV) comprising a capsid containing a nucleic acid comprising a promoter operably linked via a chimeric intron to a transgene encoding a lysosomal storage disorder-associated protein. In some aspects, the disclosure provides a recombinant AAV (rAAV) comprising a capsid containing nucleic acid comprising a promoter operably linked via a chimeric intron to a transgene, wherein the promoter and the transgene are separated by the chimeric intron, and wherein the nucleic acid does not contain an enhancer element, and wherein the transgene encodes a lysosomal storage disorder-associated protein. In some embodiments, the promoter comprises a chicken beta-actin (CB) promoter. In some embodiments, the chimeric intron comprises chicken beta actin intron and/or rabbit beta globin intron. In some embodiments, the nucleic acid further comprises a woodchuck hepatitis virus posttranscriptional regulatory element (WPRE). In some embodiments, the transgene is located in between the chimeric intron and the WPRE.

Accordingly, in some aspects the disclosure provides a recombinant AAV (rAAV) comprising a capsid containing a nucleic acid comprising an artificial transcription element operably linked to a transgene, wherein the artificial transcription element is represented by SEQ ID NO: 2, and wherein the transgene encodes a lysosomal storage disorder-associated protein. In some embodiments, the rAAV further comprises a woodchuck hepatitis virus posttranscriptional regulatory element (WPRE). In some embodiments, the transgene is located in between the transcription element and the WPRE.

In some embodiments, rAAV described by the disclosure include a transgene that encodes acid beta-galactosidase (βgal). In some embodiments, the transgene is GLB1. In some embodiments, the βgal is human βgal. In some embodiments, rAAV described by the disclosure include a transgene encodes a β-N-acetylhexosaminidase (HexA) and/or hexosaminidase B (HexB).

In some embodiments, at least one capsid protein of an rAAV described herein is AAV1, AAV2, AAV3, AAV4, AAV5, AAV6, AAV7, AAV8, AAVrh8, AAV9, AAV10, or AAVrh10 capsid protein. In some embodiments, at least one ITR of an rAAV described herein is selected from the group consisting of AAV1 ITR, AAV2 ITR, AAV3 ITR, AAV4 ITR, AAV5 ITR, or AAV6 ITR. In some embodiments, at least one ITR is a full length ITR. In some embodiments, an rAAV comprises two ITRs, wherein the hybrid promoter and transgene are located between the two ITRs. In some embodiments, an rAAV described herein has one of the following serotypes: AAV1, AAV2, AAV3, AAV4, AAV5, AAV6, AAV7, AAV8, AAVrh8, AAV9, AAV10, or AAVrh10.

In some embodiments, disclosure relates to nucleic acids encoding components of rAAVs described herein. For example, in some aspects, the disclosure provides an isolated nucleic acid comprising a sequence selected from SEQ ID NO: 1 to 6.

In some embodiments, nucleic acids encoding components of an rAAV (e.g., nucleic acids comprising a sequence selected from SEQ ID NO: 1 to 6) are contained in a host cell. In some embodiments, the host cell is a eukaryotic cell. In some embodiments, the host cell is a mammalian cell. In some embodiments, the host cell is a prokaryotic cell. In some embodiments, the host cell is a bacterial cell.

In some embodiments, host cells further comprise an isolated nucleic acid encoding an AAV capsid protein (e.g., AAV1, AAV2, AAV3, AAV4, AAV5, AAV6, AAV7, AAV8, AAVrh8, AAV9, AAV10, or AAVrh10 capsid protein).

In some aspects, the disclosure provides a method for treating a lysosomal storage disorder comprising administering a recombinant AAV (rAAV) as described herein to a subject having a lysosomal storage disorder. In some embodiments, the lysosomal storage disorder is GM1 gangliosidosis and the transgene is GLB1. In some embodiments, the lysosomal storage disorder is Tay-Sachs disease or Sandhoff disease and the transgene is β-N-acetyl-hexosaminidase (HexA) and/or hexosaminidase B (HexB).

Methods of administering rAAV to a subject are also provided by the disclosure. In some embodiments, the rAAV is administered by intracranial injection, intracerebral injection, or injection into the CSF via the cerebral ventricular system, cisterna magna, or intrathecal space.

In some aspects, the disclosure relates to a composition comprising an rAAV as described herein. In some embodiments, compositions comprise a host cell having a nucleic acid encoding an rAAV. In some embodiments, compositions further comprise a pharmaceutically acceptable carrier. In some embodiments, compositions comprising a host cell further comprise a sterile cell culture medium. In some embodiments, compositions comprising a host cell comprise a cryopreservative.

In some aspects, the disclosure provides a kit comprising: a container housing a recombinant AAV (rAAV) as described herein; or, a composition comprising a recombinant AAV (rAAV) as described herein. In some embodiments, kits further comprise a container housing a pharmaceutically acceptable carrier. In some embodiments, the rAAV or composition comprising the rAAV and the pharmaceutically acceptable carrier are housed in the same container. In some embodiments, the container is a syringe.

In some aspects, the disclosure relates to the discovery that rAAV vectors comprising multiple (e.g., 2, 3, 4, or more) promoters allow for simultaneous, tissue-specific expression of transgenes of interest. In some embodiments, rAAV vectors comprising multiple promoters target multiple cell types (e.g., CNS cell types) while avoiding off-target and safety (e.g., toxicity) issues associated with the use of ubiquitous promoters, such as pol III promoters (e.g., U6 promoter, H1 promoter, etc.).

Accordingly, in some embodiments, the disclosure provides an rAAV comprising a capsid containing a nucleic acid having a first cell-type-specific promoter operably linked to a first transgene and a second cell-type-specific promoter linked to a second transgene, wherein the first promoter and the second promoter are not specific for the same cell-type. In some embodiments, the first promoter and the second promoter are specific for the same tissue (e.g., CNS tissue). In some embodiments, the first promoter is specific for neurons and optionally is a Synapsin 1 promoter (Syn1 promoter). In some embodiments, a Syn1 promoter is represented by SEQ ID NO: 13. In some embodiments, the second promoter is specific for astrocytes, and optionally is a GfaABC$_1$D (also referred to as GFAP) promoter. In some embodiments, a GFAP promoter is represented by SEQ ID NO: 14.

In some embodiments, the first transgene encodes a CNS disease-associated gene (e.g., protein, interfering RNA, etc.). In some embodiments, the second transgene encodes a CNS disease-associated gene (e.g., protein, interfering RNA, etc.). In some embodiments, an interfering RNA is a dsRNA, siRNA, shRNA, miRNA, or amiRNA. In some embodiments, the nucleic acid comprises one or more ITRs. In some embodiments, the capsid is an AAV9 capsid.

In some embodiments, the disclosure provides a method for treating a CNS-associated disease comprising administering an recombinant AAV (rAAV) comprising a capsid containing a nucleic acid having a first cell-type-specific promoter operably linked to a first transgene and a second cell-type-specific promoter linked to a second transgene, wherein the first promoter and the second promoter are not specific for the same cell-type. In some embodiments of the method the first and/or second promoter are specific for cells of the CNS tissue.

BRIEF DESCRIPTION OF DRAWINGS

FIGS. 2A-2B show 4e10vg; FIGS. 2E-2F show 2.6e10vg; FIGS. 2I-2J show 2.6e9vg; FIGS. 2C-2D show naïve βgal$^{-/-}$ and FIGS. 2G-2H show naïve βgal$^{+/-}$ mice. Images are representative of N≥3 mice/group.

(FIG. 3B) 2.6e10vg and (FIG. 3C) 2.6e9vg all retained motor performance significantly better than naïve βgal$^{-/-}$ controls at 6 months post injection using non-parametric, unpaired Student T Test and Welsh-correction (P=0.006, 0.0009, 0.005 respectively). N=3-15 animals/group at each time point, and N=6-10 animals/group at 6 months post-treatment.

FIGS. 5A-5F show intracranial injections of AAV in βgal$^{-/-}$ mice result in abnormal Filipin staining in areas of highest enzyme expression. FIG. 5A shows coronal sections of mouse brain stained with Xgal for βgal enzyme presence and counterstained with Nuclear Fast Red at 12 weeks post injection in representative βgal$^{-/-}$ (KO+AAV) injected with 10 of AAVrh8-CBA-mβgal-WPRE (2.6e10vg total dose) bilateral into the thalamus. FIG. 5B shows untreated βgal$^{-/-}$ mouse untreated (KO Untreated). Boxes represent location of images depicted in (FIG. 5C)-(FIG. 5F). Filipin staining on adjacent brain sections in βgal$^{-/-}$ animal treated with 2.6e10vg of AAVrh8-CBA-mβgal-WPRE are shown in FIG.

5C and FIG. 5E. FIG. 5D and FIG. 5F show an untreated βgal$^{-/-}$ mouse (KO Untreated). Filipin images taken at 10× magnification. Images are representative of N≥3 mice/group.

FIG. 6A and FIG. 6B show injection of 4e10vg at 621 days. FIG. 6C and FIG. 6D show injection of 2.6e10vg at 547 days. FIG. 6E and FIG. 6F show injection of 2.6e9vg at 495 days. FIG. 6G and FIG. 6H show injection of Naïve βgal$^{-/-}$~250 days with storage throughout. Images are representative of N≥2 mice/group.

FIGS. 7A-7K show intracranial injections of AAV in βgal$^{-/-}$ mice result in morphological changes at the site of injection in the thalamus. Intracranially injected βgal$^{-/-}$ mice were analyzed at 2 week (4e10vg) or 3 months (2.6e10vg and 2.6e9vg) post-injection by H&E staining of 20 μm coronal brain sections. Morphological changes in the injected region of the thalamus: thick arrow denotes vascular cuffing, thin arrow indicates inflammation. Left panel taken at 10×, right panel a 40× picture (from regions on the left panel). Morphological changes and neuronal loss appear to lessen at lowest inject dose. FIG. 7A and FIG. 7B show injection of 4e10vg at 2 weeks post-treatment. FIG. 7E and FIG. 7F show injection of 2.6e10vg at 3 months post-treatment. FIG. 7I and FIG. 7J show injection of 2.6e9vg at 3 months post-treatment. FIG. 7G and FIG. 7H show untreated Naïve βgal$^{+/-}$ at age of treated animals. FIG. 7C and FIG. 7D show untreated Naïve βgal$^{-/-}$ at age of treated animals. FIG. 7K shows a cerebrum injected with AAVrh8-mβgal. Red arrow indicates injection site in βgal animals and location of pictures shown here. Scale bar represents 100 um. Images are representative of N≥3 mice/group.

FIGS. 8A-8K show intracranial injections of AAV in βgal$^{-/-}$ mice result in morphological changes at the site of injection in the deep cerebellar nuclei. Intracranially injected βgal$^{-/-}$ mice were analyzed at 2 week (4e10vg) or 3 months (2.6e10vg and 2.6e9vg) post-injection by H&E staining of 20 μm coronal brain sections. Morphological changes noted in the injected region of the DCN. Thick arrow denotes vascular cuffing. Arrowhead indicates suspected neuronal engulfment. Left panel taken at 10×, right panel at 40× (from regions depicted on the left panel). Morphological changes and neuronal loss appear to lessen at lowest inject dose. FIG. 8A and FIG. 8B show injection of 4e10vg at 2 weeks post-treatment. FIG. 8E and FIG. 8F show injection of 2.6e10vg at 3 months post-treatment. FIG. 8I and FIG. 8J show injection of 2.6e9vg at 3 months post-treatment. FIG. 8G and FIG. 8H show untreated Naïve βgal$^{+/-}$ at age of treated animals. FIG. 8C and FIG. 8D show injection of Naïve βgal$^{-/-}$ at age of treated animals. FIG. 8K shows a DCN injected with AAVrh8-mβgal. Arrow indicates injection site in βgal animals and location of pictures shown here. Scale bar represents 100 um. Images are representative of N≥3 mice/group.

FIGS. 9A-9L show intracranial injections of AAV in βgal$^{+/-}$ and βgal$^{-/-}$ mice result in abnormal Filipin staining in areas of most intense enzyme expression. Sagittal sections of mouse brain stained with Xgal for βgal enzyme presence and counterstained with Nuclear Fast Red at 10 weeks post injection in representative (FIG. 9A) βgal$^{+/-}$ (CA+AAV) (FIG. 9B) βgal$^{-/-}$ (KO+AAV) injected with 10 of AAVrh8-CBA-mβgal-WPRE at 1.7×10$^{12}$vg/μl bilateral into the thalamus, 2 ul into intracerebral ventricles and 0.3 ul in the deep cerebellar nuclei, and (FIG. 9C) βgal$^{-/-}$ mouse untreated (KO Untreated). Boxes represent location of images depicted in FIGS. 9D-9l. Filipin staining was positive in regions of most intense enzyme expression in both CA+AAV (FIG. 9D, FIG. 9G, and FIG. 9J β gal$^{+/-}$) and βgal$^{-/-}$ KO+AAV (FIG. 9E, FIG. 9H and FIG. 9K) injected animals. FIG. 9F, FIG. 9I and FIG. 9L show βgal$^{-/-}$ mouse untreated (KO Untreated) had no change in Filipin content. Filipin staining on brain sections taken at 10× magnification. Images are representative of N≥3 mice/group.

FIGS. 10A-10B show alterations in vector design lead to a decrease in βgal protein presence and/or enzyme activity in βgal$^{+/-}$ mice. FIG. 10A shows βgal enzyme activity in 2 mm×2 mm biopsy punches in injected structures. 10 of AAVrh8-vector (total dose 3.4e9vg, or 2.0e10vg, CB6 High only) or mock treated PBS bilateral into the thalamus, as determined by 4-MU assay at ~6 weeks post injections. Enzyme activity is normalized to protein concentration by Bradford, and is reported as nmol/hour/mg protein. Error bars represent mean+SD, N=3/group, and * indicates significant difference of βgal$^{+/-}$+AAV (CA+vector name) vs. βgal$^{+/-}$ Untreated (CA Untreated) or as indicated by connecting line. P value calculated using unpaired multiple T tests (Holm-Sidak) where *=p<0.05, =p<0.01, and *=p<0.001. FIG. 10B shows endogenous βgal protein presence as determined by Western blot which appears at 67 kd, where transgene expression from the AAV vector appears as a higher weight band. Loading control is Actin appearing at 42 kd. Western blot shown is representative of N=3 blots ran.

FIGS. 15A-15F show Xgal staining for βgal enzyme presence in βgal⁻/⁻ mice demonstrates spread of enzyme throughout the brain in an expression and dose dependent manner. Sagittal sections of mouse brain stained with Xgal for βgal enzyme activity and counterstained with Nuclear Fast Redat ~6 weeks post injection in a representative βgal⁻/⁻ injected bilaterally with 10 into the thalamus and 0.3 ul in the DCN of AAVrh8-vector (total dose 3.4e9vg, or 2.0e10vg for the CBA High only) (FIGS. 15A-15C), or untreated (KO Untreated; FIG. 15E) or βgal⁺/⁻ mice untreated (CA Untreated; FIG. 15F). N=2-3/group. Scale bar=10 mm. FIG. 15D shows KO mice treated with empty vector.

FIGS. 17A-17L show Filipin staining for GM1 content in spinal cords of βgal⁻/⁻ mice after therapeutic treatment with AAVrh8 vectors. Cervical (FIG. 17A, FIG. 17C, FIG. 17E, FIG. 17G, FIG. 17I and FIG. 17K) and thoracic (FIG. 17B, FIG. 17D, FIG. 17F, FIG. 17H, FIG. 17J and FIG. 17L) sections of spinal cord stained with Filipin for GM1 content or nuclear stain ToPro3 (KO Untreated, ToPro3, bottom row) at 6 weeks post injection in representative βgal⁻/⁻ injected bilaterally with 10 into the thalamus and 0.3 ul in the DCN of AAVrh8-vector (total dose 3.4e9vg, or 2.0e10vg, CBA High only), or untreated (KO Untreated). N=2-3/group. Images taken at 5×, scale=100 mm.

FIGS. 22A-22F show neuropathology in the monkey thalamus. In FIG. 22A, mononuclear perivascular cuffs (arrow) and necrotic area in the white matter (*) are seen. FIG. 22B shows a Luxol Fast Blue-stained section where arrows delineate one large area of necrosis, vascular proliferation, and white matter loss (note pallor compared to adjacent dark blue color). FIG. 22C shows a necrotic area in the thalamus with vacuolation (arrows). FIG. 22D is an example of a vascular cuff in the thalamus (40×). Similar neuropathology was seen in the lowest dose (1/30) (FIG. 22E). FIG. 22F shows a normal thalamus in PBS injected animal; (lx dose, FIGS. 22A-22D; 1/30 dose, FIG. 22E; PBS injected, FIG. 22F).

FIG. 25G shows the magnification of the boxed region in FIG. 25E. The arrows indicate eosinophilic material in neurons.

FIGS. 26A-2B present a panel of new AAV vectors with an expected gradient of HexA expression levels. FIG. 26A shows the systematic removal of expression elements from the current version (top) to its most basic from without a classical promoter element of ITR-flanked cDNA with a polyadenylation signal (bottom vector), while

FIGS. 31A-31T show mice brains expressing highest levels of cynomolgus Hex protein contain eosinophilic neurons. H&E stain indicates the presence of neurons containing eosinophillic granules that correlate with cynomolgus Hex expression levels in the hippocampus and thalamus (40×). Group 1 (FIGS. 31A, 31K), Group 2 (FIGS. 31B, 31L), Group 3 (FIGS. 31C, 31M), Group 4 (FIGS. 31D, 31N), Group 5 (FIGS. 31E, 31O), Group 6 (FIGS. 31F, 31P), Group 7 (FIGS. 31G, 31Q), Group 8 (FIGS. 31H, 31R), Group 9 (FIGS. 31I, 31S), and Group 10 (FIGS. 31J, 31T) mice.

FIGS. 32A-32T show that cynomolgus macaque Hexa expression in athymic nude mouse brain varies among AAV vectors. Hexa staining (green) in the thalamus and hippocampus of Group 1 (FIGS. 32A, 32K), Group 2 (FIGS. 32B, 32L), Group 3 (FIGS. 32C, 32M), Group 4 (FIGS. 32D, 32N), Group 5 (FIGS. 32E, 32O), Group 6 (FIGS. 32F, 32P), Group 7 (FIGS. 32G, 32Q), Group 8 (FIGS. 32H, 32R), Group 9 (FIGS. 32I, 32S), and Group 10 (FIGS. 32J, 32T) mice; Nuclei counterstained with DAPI (blue). Arrows indicate enzyme positive cells.

FIGS. 33A-33T show that decreased expression of cynomolgus Hex protein leads to a reduction in microglia activation. Iba-1 staining indicates reduced inflammation in groups with reduced cynomolgus Hex protein expression in the hippocampus and thalamus (20×). Group 1 (FIGS. 33A, 33K), Group 2 (FIGS. 33B, 33L), Group 3 (FIGS. 33C, 33M), Group 4 (FIGS. 33D, 33N), Group 5 (FIGS. 33E, 33O), Group 6 (FIGS. 33F, 33P), Group 7 (FIGS. 33G, 33Q), Group 8 (FIGS. 33H, 33R), Group 9 (FIGS. 33I, 33S), and Group 10 (FIGS. 33J, 33T).

FIGS. 34A-34T show that the decreased expression of cynomolgus Hex protein leads to a reduction in reactive astrogliosis. GFAP staining indicates reduced inflammation in groups with reduced cynomolgus Hex protein expression in the hippocampus and thalamus (20×). Group 1 (FIGS. 34A, 34K), Group 2 (FIGS. 34B, 34L), Group 3 (FIGS. 34C, 34M), Group 4 (FIGS. 34D, 34N), Group 5 (FIGS. 34E, 34O), Group 6 (FIGS. 34F, 34P), Group 7 (FIGS. 34G, 34Q), Group 8 (FIGS. 34H, 34R), Group 9 (FIGS. 34I, 34S), and Group 10 (FIGS. 34J, 34T).

In FIG. 38A, the pre- and post-surgical brain MRI are shown using different sequences. AAVrh8 vector formulations contained 2 mM gadolinium to analyze the distribution of the injected solution using T1-weighted MRI; the volume of the distribution of gadolinium in this animal (Gd-enhanced volume) was 1.67 mL. In FIG. 38B, the volume of distribution (Vd) for each NHP and average±SD are shown; the total infused volume in the thalamus (Vi) was 0.3 mL.

FIGS. 40A-40C show the hyperintensities in brain MRIs detectable in the thalamus of some AAVrh8-injected NHP at 90 days post-injection. One NHP in cohort 1 (FIG. 40A) showed a large hyperintensity in the left thalamus at the 90 day imaging time, although it was undetectable at earlier imaging time points. FIG. 40B shows an NHP in cohort 2 where bilateral hyperintensity signals were detected starting at d30 and remained unchanged until day 90. In FIG. 40C, an NHP in cohort 3 showed a hyperintense signal in the left thalamus from d30-d90.

FIG. 41 shows the biopsy sampling of coronal brain sections. Higher than normal hexosaminidase was measured in the dorsal (D) and ventral (V) samples in the right (R) or left (L) thalamus.

FIGS. 43A-43B show severe focal spongiosis with perivascular cuffing in the left thalamus of one AAVrh8-injected monkey in cohort 1. FIG. 43A was taken at 4× magnification; FIG. 43B was taken at 10× magnification.

FIGS. 44A-44B show neuropathology observations in cohort 3 monkeys. While neuronal degeneration was rare in these monkeys (FIG. 44A), in monkey 295709, there was evidence of perivascular gitter cells (FIG. 44B), likely associated with injection track.

FIGS. 48A-48F show that the intracranial injection of AAVrh8-cmHex vectors results in increased Hex expression and reduction in GM2 ganglioside content in the brain of Sandhoff mice. Six to eight week-old Sandhoff mice received intracranial injections of PBS (n=1; purple bars; n=1), AAVrh8-CBA-cmHex-W (green bars (A), n=3, 4.68× $10^9$ vg), AAVrh8-CBA-cmHex (orange bars (B), n=3, 4.68× $10^9$ vg), or AAVrh8-CB-I-cmHex (blue bars (C), 4.68× $10^9$ vg–n=3; C(5×): 2.34×$10^{10}$ vg–n=4) vectors. The brain was collected at 4 weeks post-injection and divided in 2-3 mm coronal blocks as shown in the top schematic; vertical arrows indicate the injection sites. In FIGS. 48A-48C, the total Hex enzyme activity (HexA, B, and S) was measured using the artificial substrate MUG and then represented as fold-over wild type level (T, black bars, n=1). Asterisks (*) represent animals with no detectable Hex activity. FIGS. 48D and 48F are bar graphs of the qualitative LC-MS/MS used to measure GM2 ganglioside content.

FIG. 49A shows a structural rendering of a CB promoter, represented by SEQ ID NO: 1. FIG. 49B shows a structural rendering of a CB(6)-I promoter, represented by SEQ ID NO: 4. FIG. 49C shows a structural rendering of a P2-I promoter, represented by SEQ ID NO: 5.

DETAILED DESCRIPTION OF INVENTION

Figure 1:
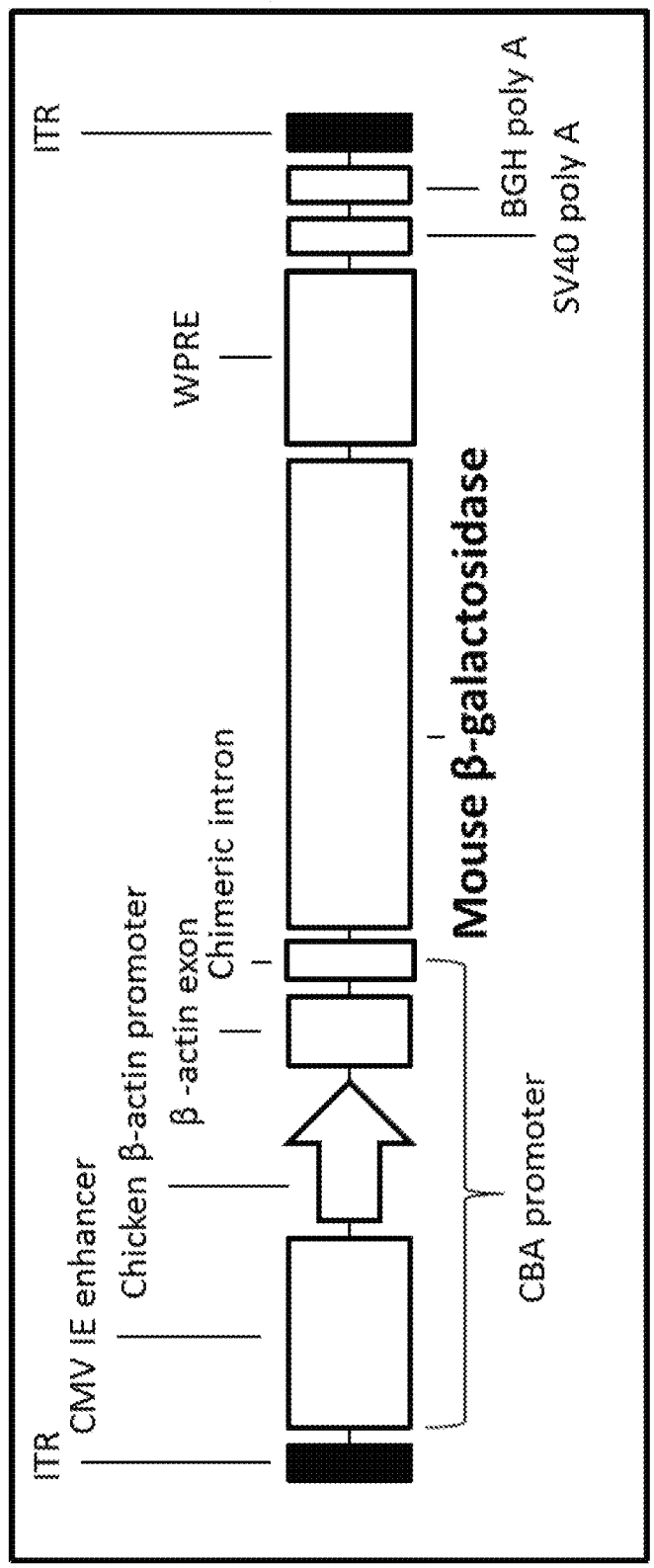
FIG. 1 shows a schematic of the rAAV vector CBA-mβgal-WPRE. Two inverted terminal repeats (ITRs) from AAV2 flank the vector on each end. The CBA promoter is composed of a cytomegalovirus immediate early enhancer (CMV) fused to the chicken beta-actin promoter followed by a chimeric chicken beta-actin/rabbit beta globin intron (CBA), the mouse lysosomal acid β-galactosidase cDNA (mβgal), a woodchuck hepatitis virus post-transcriptional regulatory element (WPRE), and two polyA signals in tandem derived from the bovine growth hormone (BGH) and SV40. This vector was then packaged in an AAVrh8 capsid.

Lysosomal storage disorders (LSD) are a class of >50 disorders associated with malfunction of a resident enzyme which leads to accumulation of un-degraded substrates in lysosomes. Over time, this accumulation can lead to lysosomal malfunction which results in a cascade of events often resulting in cell death. LSDs with central nervous system (CNS) involvement require the intended therapy to cross or bypass the blood brain barrier in order to deliver functional enzyme to target cells to achieve disease resolution. One therapeutic delivery approach has been AAV-mediated target gene delivery.

Delivery of transgenes with current rAAV vectors causes accumulation of un-degraded substrates or dysregulation of the lysosomal compartment, which leads to responses that upregulate lysosomal biogenesis, substrate reduction or exocytosis. Furthermore, introduction of supra-physiological levels of a therapeutic protein via rAAV vector-driven transgene expression can also trigger deleterious protection cascades which may be associated with unfolded protein response common in these disorders. New rAAV vectors capable of safe and efficient expression of lysosomal enzymes in the CNS are therefore needed.

Accordingly, in some aspects, the instant disclosure provides rAAVs and rAAV vectors that have been modified to be useful for the expression of lysosomal enzymes in tissues such as the CNS. In some aspects, the invention relates to the use of modified rAAVs for the treatment of lysosomal storage disorders, such as GM1 gangliosidosis, Tay-Sachs disease and/or Sandhoff disease. The disclosure is based, in part, on the discovery that certain regulatory sequences and elements, for example promoter regions, can be engineered for use in rAAVs to provide levels of transgene expression that are therapeutically effective yet do not cause the vector-mediated genotoxicity associated with previously used rAAVs.

In some aspects, the disclosure relates to the discovery that rAAV vectors comprising multiple (e.g., 2, 3, 4, or more) promoters allow for simultaneous, tissue-specific expression of transgenes of interest. For example, certain diseases (e.g., amyotrophic lateral sclerosis; ALS) affect a broad population of cell-types (e.g., neurons, astrocytes, etc.) in a particular tissue (e.g., CNS tissue). Promoters of currently utilized therapeutic constructs, in some embodiments, are not sufficiently universal to drive adequate transgene (e.g., therapeutic transgene) expression in the variety of affected cell-types to halt disease progression. In some embodiments, rAAV constructs having multiple cell-type-specific promoters as described by the disclosure offer an improved transduction profile over currently utilized rAAV vectors having ubiquitous promoters.

Accordingly, in some embodiments, the disclosure provides an rAAV comprising a capsid containing a nucleic acid having a first cell-type-specific promoter operably linked to a first transgene and a second cell-type-specific promoter linked to a second transgene, wherein the first promoter and the second promoter are not specific for the same cell-type.

As used herein, "tissue-specific promoter" refers to a promoter that preferentially regulates (e.g., drives or up-regulates) gene expression in a particular cell type relative to other cell types. A cell-type-specific promoter can be specific for any cell type, such as central nervous system (CNS) cells, liver cells (e.g., hepatocytes), heart cells, kidney cells, eye cells, muscle cells, etc. For example, the human synapsin 1 promoter (Syn1 promoter) preferentially drives gene expression in neurons and the GfaABC$_1$D (also referred to as GFAP) promoter preferentially drives expression in astrocytes. However, it should be appreciated that several cell-types may be resident within a particular type of tissue. For example, central nervous system tissue comprises neuronal cells and non-neuronal cells (e.g., glial cells, astrocytes, etc.). Thus, in some embodiments, the first promoter and the second promoter of an rAAV described by the disclosure are not specific for the same cell-type but are specific for the same tissue type.

In some embodiments, the first promoter is specific for neurons and optionally is a Synapsin 1 promoter (Syn1 promoter). In some embodiments, a Syn1 promoter is represented by SEQ ID NO: 13. In some embodiments, the second promoter is specific for astrocytes, and optionally is a GFAP promoter. In some embodiments, a GFAP promoter is represented by SEQ ID NO: 14.

Further examples of tissue-specific promoters include but are not limited to a liver-specific thyroxin binding globulin (TBG) promoter, an insulin promoter, a glucagon promoter, a somatostatin promoter, a pancreatic polypeptide (PPY) promoter, a synapsin-1 (Syn1) promoter, a creatine kinase (MCK) promoter, a mammalian desmin (DES) promoter, a α-myosin heavy chain (α-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

Recombinant AAVs

In some aspects, the disclosure provides isolated AAVs. As used herein with respect to AAVs, the term "isolated" refers to an AAV that has been artificially obtained or produced. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected. In some embodiments, the rAAV comprises an AAV1, AAV2, AAV3, AAV4, AAV5, AAV6, AAV7, AAV8, AAVrh8, AAV9, AAV10 or AAVrh10 capsid protein, or a protein having substantial homology thereto.

In some embodiments, the rAAVs of the disclosure are pseudotyped rAAVs. Pseudotyping is the process of producing viruses or viral vectors in combination with foreign viral envelope proteins. The result is a pseudotyped virus particle. With this method, the foreign viral envelope proteins can be used to alter host tropism or an increased/decreased stability of the virus particles. In some aspects, a pseudotyped rAAV comprises nucleic acids from two or more different AAVs, wherein the nucleic acid from one AAV encodes a capsid protein and the nucleic acid of at least one other AAV encodes other viral proteins and/or the viral genome. In some embodiments, a pseudotyped rAAV refers to an AAV comprising an inverted terminal repeats (ITRs) of one AAV serotype and an capsid protein of a different AAV serotype. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

Methods for obtaining recombinant AAVs having a desired capsid protein are well known in the art. (See, for example, US Patent Application Publication Number US 2003/0138772, the contents of which are incorporated herein by reference in their entirety). Typically the methods involve culturing a host cell which contains a nucleic acid sequence encoding an AAV capsid protein or fragment thereof; a functional rep gene; a recombinant AAV vector composed of, AAV inverted terminal repeats (ITRs) and a transgene; and sufficient helper functions to permit packaging of the recombinant AAV vector into the AAV capsid proteins. Typically, capsid proteins are structural proteins encoded by the cap gene of an AAV. In some embodiments, AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, capsid proteins protect a viral genome, deliver a genome and/or interact with a host cell. In some aspects, capsid proteins deliver the viral genome to a host in a tissue specific manner.

In some embodiments, the AAV capsid protein is of an AAV serotype selected from the group consisting of AAV3, AAV4, AAV5, AAV6, AAV8, AAVrh8 AAV9, AAV10 and AAVrh10. In some embodiments, the AAV capsid protein is of an AAVrh8 or AAVrh10 serotype.

In some embodiments, components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain El helper functions under the control of a constitutive promoter), but which contain the rep and/or cap proteins under the control of inducible promoters. Still other stable host cells may be generated by one of skill in the art.

In some embodiments, the disclosure relates to a host cell containing a nucleic acid that comprises a coding sequence selected from the group consisting of: SEQ ID NOs: 1-6 that is operably linked to a promoter. In some embodiments, the disclosure relates to a composition comprising the host cell described above. In some embodiments, the composition comprising the host cell above further comprises a cryopreservative.

The recombinant AAV vector, rep sequences, cap sequences, and helper functions useful for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced through the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the term "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter.

A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA, miRNA inhibitor) from a transcribed gene.

The foregoing methods for packaging recombinant vectors in desired AAV capsids to produce the rAAVs of the disclosure are not meant to be limiting and other suitable methods will be apparent to the skilled artisan.

Recombinant AAV Vectors

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

Aspects of the disclosure relate to the discovery that modifying the regulatory sequences of rAAVs provides levels of transgene expression that are therapeutically effective yet do not cause the vector-mediated toxicity associated with previously used rAAVs. Accordingly, in some embodiments, the disclosure relates to a recombinant AAV (rAAV) comprising modified genetic regulatory elements. In some embodiments, the modified genetic regulatory element is a hybrid promoter.

As used herein, the term "hybrid promoter" refers to a regulatory construct capable of driving transcription an RNA transcript (e.g., a transcript comprising encoded by a transgene) in which the construct comprises two or more regulatory elements artificially arranged. Typically, a hybrid promoter comprises at least one element that is a minimal promoter and at least one element having an enhancer sequence or an intronic, exonic, or UTR sequence comprising one or more transcriptional regulatory elements. In embodiments in which a hybrid promoter comprises an exonic, intronic, or UTR sequence, such sequence(s) may encode upstream portions of the RNA transcript (e.g., as depicted in FIG. 1) while also containing regulatory elements that modulate (e.g., enhance) transcription of the transcript. In some embodiments, two or more elements of a hybrid promoter are from heterologous sources relative to one another. In some embodiments, two or more elements of a hybrid promoter are from heterologous sources relative to the transgene. In some embodiments, two or more elements of a hybrid promoter are from different genetic loci. In some embodiments, two or more elements of a hybrid promoter are from the same genetic locus but are arranged in a manner not found at the genetic locus. In some embodiments, the hybrid promoter comprise a first nucleic acid sequence from one promoter fused to one or more nucleic acid sequences comprises promoter or enhancer elements of a difference source. In some embodiments, a hybrid promoter comprises a first sequence from the chicken beta-actin promoter and a second sequence of the CMV enhancer. In some embodiments, a hybrid promoter comprises a first sequence from a chicken beta-actin promoter and a second sequence from an intron of a chicken-beta actin gene. In some embodiments, a hybrid promoter comprises a first sequence from the chicken beta-actin promoter fused to a CMV enhancer sequence and a sequence from an intron of the chicken-beta actin gene.

In some aspects of the invention, the rAAV comprises an enhancer element. As used herein, the term "enhancer element" refers to a nucleic acid sequence that when bound by an activator protein, activates or increases transcription of a gene or genes. Enhancer sequences can be upstream (i.e., 5') or downstream (i.e., 3') relative to the genes they regulate. Examples of enhancer sequences include cytomegalovirus (CMV) enhancer sequence and the Simian vacuolating virus 40 (SV40) enhancer sequence. In some embodiments, rAAVs comprise a CMV enhancer element or a portion thereof. As used herein, the term "a portion thereof" refers to a fragment of a nucleotide or amino acid sequence that retains the desired functional characteristic of the entire nucleotide or amino acid sequence from which it is derived. For example, a "CMV enhancer sequence or a portion thereof" refers to a nucleotide sequence derived from wild-type CMV enhancer that is capable of increasing transcription of a transgene.

In some aspects, the rAAV comprises a posttranscriptional response element. As used herein, the term "posttranscriptional response element" refers to a nucleic acid sequence that, when transcribed, adopts a tertiary structure that enhances expression of a gene. Examples of posttranscriptional regulatory elements include, but are not limited to, woodchuck hepatitis virus posttranscriptional regulatory element (WPRE), mouse RNA transport element (RTE), constitutive transport element (CTE) of the simian retrovirus type 1 (SRV-1), the CTE from the Mason-Pfizer monkey virus (MPMV), and the 5' untranslated region of the human heat shock protein 70 (Hsp70 5'UTR). In some embodiments, the rAAV vector comprises a woodchuck hepatitis virus posttranscriptional regulatory element (WPRE).

In some aspects, the disclosure provides rAAV vectors comprising a hybrid or chimeric intron. As used herein, the term "chimeric intron" refers an intron having sequences from two or more different sources. In some embodiments, a chimeric intron comprises a nucleic acid encoding a splice donor site from a first source (e.g., organism or species) and a splice acceptor site from a second source (e.g., organism or species). In some embodiments, a chimeric intron comprise one or more transcriptional regulatory elements and/or enhancer sequences. In some embodiments, a chimeric intron is positioned between an exon of a hybrid promoter and transgene.

In certain embodiments, the disclosure relates to rAAV vectors comprising artificial transcription elements. As used here, the term "artificial transcription element" refers, in some embodiments, to a synthetic sequence enabling the controlled transcription of DNA by an RNA polymerase to produce an RNA transcript. Transcriptionally active elements of the present invention are generally smaller than 500 bp, preferably smaller than 200 bp, more preferably smaller than 100, most preferably smaller than 50 bp. In some embodiments, an artificial transcription element comprises two or more nucleic acid sequences from transcriptionally active elements. Transcriptionally active elements are generally recognized in the art and include, for example, promoter, enhancer sequence, TATA box, G/C box, CCAAT box, specificity protein 1 (Sp1) binding site, Inr region, CRE (cAMP regulatory element), activating transcription factor 1 (ATF1) binding site, ATF1-CRE binding site, APBβ box, APβα box, CArG box, CCAC box and those disclosed by U.S. Pat. No. 6,346,415. Combinations of the foregoing transcriptionally active elements are also contemplated.

In some embodiments, the artificial transcription element comprises promoter sequence. In some embodiments, the artificial transcription element comprises enhancer sequence. In some embodiments, the artificial transcription element comprises ATF1-CRE binding site. In some embodiments, the artificial transcription element comprises SP1 binding site. In some embodiments, the artificial transcription element comprises C box. In some embodiments, the artificial transcription element comprises TATA box. In some embodiments, the artificial transcription element comprises ATF1-CRE binding site, SP1 binding site and TATA box. In some embodiments, the artificial transcription element is represented by SEQ ID NO: 2.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA, miRNA inhibitor).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence.

Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, Petal., Human Gene Therapy, 2000; 11: 1921-1931; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In some embodiments, the rAAVs of the disclosure are pseudotyped rAAVs. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Recombinant AAV Vector: Transgene Coding Sequences

The composition of the transgene sequence of the rAAV vector will depend upon the use to which the resulting vector will be put. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

In some aspects, the invention relates to rAAV vectors useful for the treatment of lysosomal storage disorders. Lysosomal storage disorders (also referred to as Lysosomal storage diseases) are a group of inherited metabolic disorders that result from defects in lysosomal function. Generally, lysosomal storage diseases are characterized by impaired function of a single protein (e.g., enzyme) involved in lysosomal metabolism. For example, Tay-Sachs disease is caused by a genetic mutation in the hexosaminidase A (HEXA) gene and results in the inability of the HEXA enzyme to hydrolyze $GM_2$ gangliosides. Other examples of lysosomal storage diseases and their associated proteins include but are not limited to Aspartylglucosaminuria (Aspartylglucosamininidase), Infantile Batten disease (Palmitoyl protein thioesterase), Late infantile Batten disease (tripeptidyl peptidase), Fabry disease (α-Galactosidase), Fucosidosis (α-Fucosidase), Galactosialidosis (Protective protein/cathepsin A), Gaucher disease (β-Glucosidase), Galactosialidosis (Protective Protein/Cathepsin A), Globoid-cell leukodystrophy (Galactosylceramidase), GM1 gangliosidosis (β-Galactosidase), α-Mannosidosis (α-Mannosidase), Metachromatic leukodystrophy (Arylsulfatase A), Mucopolysaccharidosis I (α-L-Iduronidase), Mucopolysaccharidosis II (iduronate sulfatase), Mucopolysaccharidosis IIIA (Heparin Sulfatase), Mucopolysaccharidosis IIIB (α-N-acetylglucosaminidase), Mucopolysaccharidosis IIIC (acetyl-CoA alpha glucosaminide acetyltransferase), Mucopolysaccharidosis IIID (N-acetylglucosamine-6-sulfate sulfatase), Mucopolysaccharidosis IVA (N-acetylgalactosamine 6-sulfatase), Mucopolysaccharidosis IVB (β-Galactosidase), Mucopolysaccharidosis IX (hyaluronidase), Mucopolysaccharidosis VI (Arylsulfatase B), Mucopolysaccharidosis VII (β-Glucuronidase), Mucolipidosis type I (α-neuraminidase), Mucolipidosis type II (GlcNAc-1-phosphotransferase), Mucolipidosis type III (N-acetylglucosamine-1-phosphotransferase), Nieman-Pick disease (Acid sphingomyelinase), Pompe disease (α-Glucosidase), Sandhoff disease (β-Hexosaminidase A and B) Schindler disease (α-N-acetylgalactosaminidase), Tay-Sachs disease (β-Hexosaminidase A), and Wolman disease (Acid lipase).

In some embodiments, the disclosure provides an rAAV comprising a transgene encoding a lysosomal storage disease-related protein. In some embodiments, the lysosomal storage disease-related protein is selected from the group consisting of HEXA, HEXB, and GLB1. In some embodiments, the lysosomal storage disease-related protein is HEXA. In some embodiments, the lysosomal storage disease-related protein is HEXB. In some embodiments, the lysosomal storage disease-related protein is GLB1.

Also contemplated herein are methods of treating a lysosomal storage disease by delivering a transgene to a subject using the rAAVs described herein. In some embodiments, the disclosure relates to a method for treating a lysosomal storage disease, the method comprising administering a rAAV to a subject. In some embodiments, the rAAV comprises a hybrid promoter. In some embodiments, the rAAV comprises a chimeric intron. In some embodiments, the rAAV comprises an artificial transcription element. In some embodiments, the artificial transcription element comprises ATF1-CRE binding site, SP1 binding site and TATA box. In some embodiments, the promoter, chimeric intron or artificial transcription element is operably linked to a transgene. In some embodiments, the transgene is a lysosomal storage disease related transgene. In some embodiments, the transgene is selected from the group consisting of HEXA, HEXB and GLB1. In some embodiments, the lysosomal storage disease is GM2 gangliosidosis (Sandhoff Disease and Tay-Sachs Disease) and rAAV comprises a transgene encoding HEXA and HEXB. In some embodiments, the lysosomal storage disease is GM1 gangliosidosis and the transgene encodes GLB1.

In some aspects, the disclosure provides an rAAV comprising a capsid containing a nucleic acid having a first cell-type-specific promoter operably linked to a first transgene and a second cell-type-specific promoter linked to a second transgene, wherein the first promoter and the second promoter are not specific for the same cell-type. Without wishing to be bound by any particular theory, such rAAV vectors are useful, in some embodiments for the treatment of diseases that affect multiple cell types within a given tissue (e.g., CNS tissue).

Thus, in some aspects, the disclosure relates to rAAV vectors useful for the treatment of CNS-associated diseases. As used herein, "CNS-associated disease" refers to a disease or condition of the central nervous system. A CNS-associated disorder may affect the spinal cord (e.g., a myelopathy), brain (e.g., a encephalopathy) or tissues surrounding the brain and spinal cord. A CNS-related disorder may be of a genetic origin, either inherited or acquired through a somatic mutation. A CNS-related disorder may be a psychological condition or disorder, e.g., Attention Deficient Hyperactivity Disorder, Autism Spectrum Disorder, Mood Disorder, Schizophrenia, Depression, Rhett Syndrome, etc. A CNS-related disorder may be an autoimmune disorder. A CNS-related disorder may also be a cancer of the CNS, e.g., brain cancer. A CNS-related disorder that is a cancer may be a primary cancer of the CNS, e.g., an astrocytoma, glioblastomas, etc., or may be a cancer that has metastasized to CNS tissue, e.g., a lung cancer that has metastasized to the brain. Further non-limiting examples of CNS-related disorders, include Huntington's disease, Parkinson's Disease, Lysosomal Storage Disease, Ischemia, Neuropathic Pain, Amyotrophic lateral sclerosis (ALS), Multiple Sclerosis (MS), Canavan disease (CD), frontotemporal lobar degeneration (FTLD), spinocerebellar ataxias, spinal and bulbar muscular atrophy, dentatorubropallidoluysian atrophy, and Freiderich's ataxia.

In some embodiments, an rAAV vector described by the disclosure comprises a transgene encoding a CNS disease-associated gene. In some embodiments, a transgene encoding a CNS disease-associated gene encodes a protein or interfering RNA. Examples of interfering RNA include but are not limited to dsRNA, siRNA, shRNA, miRNA, and artificial miRNA (amiRNA). Examples of genes associated with CNS disease include but are not limited to DRD2, GRIA1, GRIA2, GRIN1, SLC1A1, SYP, SYT1, CHRNA7, 3Rtau/4rTUS, APP, BAX, BCL-2, GRIK1, GFAP, IL-1, AGER, associated with Alzheimer's Disease; UCH-L1, SKP1, EGLN1, Nurr-1, BDNF, TrkB, gstm1, S106β, associated with Parkinson's Disease; huntingtin (Htt), IT15, PRNP, JPH3, TBP, ATXN1, ATXN2, ATXN3, Atrophin 1, FTL, TITF-1, Xbp1s, CRAG, associated with Huntington's Disease; FXN, associated with Freidrich's ataxia; ASPA, associated with Canavan's Disease; DMD, associated with muscular dystrophy; SMN1, UBE1, DYNC1H1 associated with spinal muscular atrophy; ALS2, ANG, ATXN2, C9orf72, DCTN1, FIG4, FUS, NEFH, OPTN, PFN1, PRPH, SETX, SIGMAR1, SMN1, SOD1, SPG11, TARDBP, UBQLN2, VAPB, VCP, associated with amyotrophic lateral sclerosis (ALS); MAN2B1, MAN2B2, MAN2C1, associated with Alpha-Mannosidosis; AGA, associated with Aspartylglucosaminuria; CLN1, CLN2, CLN3, CLN5, CLN6, MFSD8, CLN8, CTSD, associated with Batten disease; MANBA, associated with Beta-Mannosidosis; CTNS, associated with cystinosis; LAMP2, associated with Danon disease; GLA, associated with Fabry disease; ASAH1, associated with Farber disease; FUCA1, associated with fucosidosis; CTSA, associated with Galactosialidosis; GBA, associated with Gaucher disease; GALC, associated with Krabbe disease; ARSA, associated with metachromic leukodystrophy; and IDUA, IDS, SGSH, NAGLU, HGSNAT, GNS, GALNS, ARSB, GUSB, HYAL1, SMPD1, NPC1, NPC2, GAA, NAGA, SLCA17A5, and LAL (LIPA), associated with Mucopolysaccharidosis disorders (e.g., Hurler syndrome, Hunter syndrome, Sanfilippo A-D, Morquio, hyaluronidase deficiency, Maroteaux-Lamy, Sly syndrome, sialidosis, I-cell disease, mucolipidosis types I-IV, multiple sulfatase deficiency, Niemann-Pick types A-C, Pompe disease, Pycnodysostosis, Sandhoff disease, Schlinder disease, Tay-Sachs, Wolman disease).

Useful transgene products also include miRNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA. In some embodiments, an inhibitory RNA is a miRNA. In some embodiments, an rAAV described by the disclosure comprises a transgene encoding an inhibitory RNA targeting human SOD1 (e.g., SOD1$^{G93A}$) and comprises SEQ ID NO: 15.

Recombinant AAV Administration Methods

The rAAVs may be delivered to a subject in compositions according to any appropriate methods known in the art. The rAAV, preferably suspended in a physiologically compatible carrier (i.e., in a composition), may be administered to a subject, i.e., host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000). In some embodiments, rAAV as described in the disclosure are administered by intravenous injection. In some embodiments, the rAAV are administered by intracerebral injection. In some embodiments, the rAAV are administered by intrathecal injection. In some embodiments, the rAAV are delivered by intracranial injection. In some embodiments, the rAAV are delivered by cisterna magna injection. In some embodiments, the rAAV are delivered by cerebral lateral ventricle injection.

Aspects of the disclosure relate to compositions comprising a recombinant AAV comprising at least one modified genetic regulatory sequence or element. In some embodiments, the composition further comprises a pharmaceutically acceptable carrier.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

rAAVs are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$-$10^{13}$ rAAV genome copies is effective to target tissues associated with lysosomal storage diseases, for example brain tissue or CNS tissue. In some cases, stable transgenic animals are produced by multiple doses of an rAAV.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intrapancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500.ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the disclosure relates to a kit for producing a rAAV, the kit comprising a container housing an isolated nucleic acid having a sequence of any one of SEQ ID NOs: 1-6. In some embodiments, the kit further comprises instructions for producing the rAAV. In some embodiments, the kit further comprises at least one container housing a recombinant AAV vector, wherein the recombinant AAV vector comprises a transgene.

In some embodiments, the disclosure relates to a kit comprising a container housing a recombinant AAV as described supra. In some embodiments, the kit further comprises a container housing a pharmaceutically acceptable carrier. For example, a kit may comprise one container housing a rAAV and a second container housing a buffer suitable for injection of the rAAV into a subject. In some embodiments, the container is a syringe.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

In some cases, the methods involve transfecting cells with total cellular DNAs isolated from the tissues that potentially harbor proviral AAV genomes at very low abundance and supplementing with helper virus function (e.g., adenovirus)

to trigger and/or boost AAV rep and cap gene transcription in the transfected cell. In some cases, RNA from the transfected cells provides a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells may also be infected with a helper virus, such as an Adenovirus or a Herpes Virus. In a specific embodiment, the helper functions are provided by an adenovirus. The adenovirus may be a wild-type adenovirus, and may be of human or non-human origin, preferably non-human primate (NHP) origin. Similarly adenoviruses known to infect non-human animals (e.g., chimpanzees, mouse) may also be employed in the methods of the disclosure (See, e.g., U.S. Pat. No. 6,083,716). In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. Nos. 5,871,982 and 6,251,677, which describe a hybrid Ad/AAV virus. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

Cells may also be transfected with a vector (e.g., helper vector) which provides helper functions to the AAV. The vector providing helper functions may provide adenovirus functions, including, e.g., E1a, E1b, E2a, E4ORF6. The sequences of adenovirus gene providing these functions may be obtained from any known adenovirus serotype, such as serotypes 2, 3, 4, 7, 12 and 40, and further including any of the presently identified human types known in the art. Thus, in some embodiments, the methods involve transfecting the cell with a vector expressing one or more genes necessary for AAV replication, AAV gene transcription, and/or AAV packaging.

In some cases, a novel isolated capsid gene can be used to construct and package recombinant AAV vectors, using methods well known in the art, to determine functional characteristics associated with the novel capsid protein encoded by the gene. For example, novel isolated capsid genes can be used to construct and package recombinant AAV (rAAV) vectors comprising a reporter gene (e.g., B-Galactosidase, GFP, Luciferase, etc.). The rAAV vector can then be delivered to an animal (e.g., mouse) and the tissue targeting properties of the novel isolated capsid gene can be determined by examining the expression of the reporter gene in various tissues (e.g., heart, liver, kidneys) of the animal. Other methods for characterizing the novel isolated capsid genes are disclosed herein and still others are well known in the art.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Example 1: Materials and Methods

Vector Design, Construction and Viral Creation.

The original AAV vector (SEQ ID NO: 3) was constructed and carries an expression cassette driven by a promoter composed of cytomegalovirus immediate early enhancer (CMV) fused to the chicken beta-actin promoter followed by a chimeric chicken beta-actin/rabbit beta globin intron (CBA), the mouse lysosomal acid β-galactosidase cDNA (mβgal), a woodchuck hepatitis virus post-transcriptional regulatory element (WPRE), and two polyA signals in tandem derived from the bovine growth hormone (BGH) and SV40. This vector is called AAV-CBA-mβgal-WPRE. AAV-CBA-mβgalE269Q-WPRE was generated by PCR mutagenesis with of the following primers: For 1: AAA CGT CTC ACT AGT CCG CGG AAT TC (SEQ ID NO: 7), Rev1: AAA CGT CTC ACT GAG AAT TGA TCA AA (SEQ ID NO: 8), For2: AAA GGT CTC CGG CCG CTA GCG TCA G (SEQ ID NO: 9), Rev2: AAA GGT CTC ATC AGT TCT ATA CTG GC (SEQ ID NO: 10). The resulting PCR product was digested with SpeI and Not I restriction enzymes and cloned in place of the wild type βgal cDNA. All other AAV vectors were generated by removal of different elements from AAV-CBA-mβgal-WPRE vector (SEQ ID NO: 3). All AAVrh8 vector stocks were produced by standard methods.

Animal Procedures

GM1-gangliosidosis mice ($\beta gal^{-/-}$), a knock out version created by insertion of a neomycin cassette in exon 6 of the β-galactosidase gene, GLB1. $\beta gal^{-/-}$, $\beta gal^{+/-}$, and $\beta gal^{+/+}$ mice are generated by mating of male $\beta gal^{-/-}$ and female $\beta gal^{+/-}$ mice or $\beta gal^{+/-}$ males and females.

Intracranial Injections

Six to eight week-old $\beta gal^{-/-}$ or $\beta gal^{+/-}$ mice were anesthetized by intraperitoneal injection of ketamine (125 mg/kg) and xylazine (12.5 mg/kg) in 0.9% saline and placed in a rodent stereotaxic frame. The fur around the incision site was clipped, and the skin scrubbed with povidine-iodine pads and 70% EtOH. The skull was exposed by a small longitudinal incision (<1 cm) along the midline. The periosteum was removed from the surgical area with sterile cotton tipped applicators. Small burr holes (<1 mm) were made using a high-speed drill at the appropriate stereotaxic coordinates. AAV vectors, or PBS, were infused in $\beta gal^{-/-}$ or $\beta gal^{+/-}$ mice with 1 μl bilaterally into the thalamus (stereotaxic coordinates: AP−2.0 mm, ML±1.5 mm from bregma; DV−3.5 mm from brain surface) and in $\beta gal^{-/-}$ mice with 0.3 or 1 μl into the deep cerebellar nuclei (AP−6.0 mm, ML±1.5 mm from bregma; DV−3.5 mm from brain surface) at a rate of 0.2 μl/min using an Ultramicro Pump to drive a 10 μl gastight glass syringe fitted with a 33G needle. Infusions were started 1 min after placement of the needle in the target structures and slowly withdrawn 2.5 min after conclusion of the infusion. The scalp was closed with sterile wound clips (9 mm).

Behavioral Assays

Rotarod testing was conducted on a Rotarod apparatus accelerating from 4 to 40 rpm over 5 minutes, with latency to fall recorded. Testing was conducted with one practice trial of 1 minute accelerating from 2 to 20 rpm at the beginning of the session followed by 3 trials with 15-20 minute resting in between. Latency to fall for each mouse in a testing session was recorded, and the longest time on the rotarod among the 3 trials was reported.

Tissue Processing

For biochemical studies in $\beta gal^{+/-}$ mice, the brain was removed and sliced into 2 mm coronal blocks using a brain matrix, and immediately frozen on dry ice. The block containing the thalamus was identified by morphology and the presence of needle entry points on the dorsal brain surface. A 2 mm diameter biopsy punch was used to sample the thalamus and the tissue plug placed in the appropriate buffer for analysis. For histological studies the brain and spinal cord were removed and placed in Neg 50 freezing medium and frozen in a dry ice/2-methylbutane bath. For biochemical studies in $\beta gal^{-/-}$ mice, cerebrum, cerebellum+ brainstem, and spinal cord were removed and immediately frozen on dry ice.

Histological Analysis

20 μm brain (sagittal and coronal) and spinal cord (transverse) sections were cut in a cryostat and stored at −80° C.

Brain sections were stained with X-gal to assess the distribution of βgal as described previously, with modifications. Briefly, slides were fixed in 0.5% glutaraldhyde in PBS, washed 3× in ice cold citrate phosphate buffer (CPB) (50 mM $C_6H_8O$, 50 mM $Na_2HPO_4$, 10 mM NaCl, pH=4.2) incubated overnight at 37° C. in X-gal staining solution [20 mM $K_4Fe(CN)_6$, 20 mM $K_3Fe(CN)_6$, 2 mM $MgCl_2$, 0.01% $C_{24}H_{39}NaO_4$, 0.02% $(C_2H_4O)nC_{14}H_{22}O$ (IGEPAL CA-630, SigmaAldrich), 97% CPB @ pH=4.2, 2 mg/ml 5-bromo-4-chloro-3-indolyl-β-D-galactosidase (X-gal) in HCON $(CH_3)_2$). The next day, slides were rinsed in CPB then water, counterstained with Vector Nuclear Fast Red, dehydrated through a series of ethanol 50%-100%, cleared with Citri-Solv and mounted with Permount.

Brain and spinal cord sections were stained with Filipin to assess lysosomal storage as described previously, with modifications. Briefly, slides were fixed in 4% paraformaldehyde in phosphate buffered saline (PBS), washed with PBS, incubated with 1.5% glycine in water, washed with PBS, incubated with 100 μg/ml of Filipin and 1 μg/ml of ToPro3 Iodide (Life Technologies, Grand Island, N.Y.) for 1-2 hours, washed with PBS and mounted with fluorescence mounting media, PermaFluor.

Brain sections were stained with Mayer's Hematoxylin and Eosin to assess morphological changes in the tissue. Briefly, slides were dried at room temperature, fixed in 4% paraformaldehyde in phosphate buffered saline (PBS), washed with water, incubated with Mayer's Hematoxylin, washed in running tap water, counterstained with Eosin, rinsed with deionized water, dehydrated through a series of ethanol 50%-100%, cleared with CitriSolv and mounted with Permount.

Whole brain slice images were captured using white light on a Nikon Super CoolScan 5000 ED with a medical slide holder. Microscope images were captured on a Leica DM550 B microscope, equipped with Leica DFC425 C and DFC365 FX digital cameras. Filipin was imaged at 405 nm and ToPro3 Iodide at 636 nm. H&E was imaged using brightfield.

All histological analysis was performed as non-blinded, qualitative analysis on an N≥2-3 animals with representative pictures shown in figures.

βgal Enzymatic Assays and Immunoblotting

Biopsy punches were homogenized in lysis buffer (0.1% Triton X-100 in 0.2M $CH_3COONa$, 0.1M NaCl, pH 4.3) and assayed for βgal enzymatic activity. Briefly, a reaction with βgal substrate=1 mM 4-Methylumbelliferyl-β-D-galactoside (4-MUG) was performed in a 96-well plate format and the amount of 4-methylumbelliferyl (4-MU) released was measured against a standard curve with fluorescence detection by excitation at 360 nm and emission at 460 nm using a BioTek Synergy HT plate reader. Enzymatic activity was normalized to protein content as determined by Bradford assay and reported as nmol (of substrate converted)/hour/mg protein. For immunoblotting injection site biopsy punches were homogenized in T-PER buffer supplemented with Complete Mini protease inhibitor cocktail, incubated on ice for 10 min and then centrifuged at 10,000×g for 5 min. The supernatant was collected and protein concentration determined using a Bradford assay. Total protein (20 μg) was separated by polyacrylamide gel electrophoresis using Mini-PROTEAN TGX precast gels, and protein transferred to NitroPure nitrocellulose membrane. Blots were blocked in Tris-buffered saline-Tween-20 (TBST) with 5% fat-free milk, and then incubated with primary antibodies to α-rabbit GLB1 (β-galactosidase antibody) (1:250) and α-mouse β-Actin (1:1000). HRP-conjugated anti-rabbit and anti-mouse secondary antibodies were used (1:4000) and signal detection was done with Pierce ECL Western Blotting Substrate and blots exposed to Amersham Hyperfilm ECL.

Genome Copies

Genomic DNA from injection site biopsy punches was isolated using Qiagen DNeasy Blood and Tissue Kit, and concentration determined using a Nanodrop spectrophotometer. The number of AAV vector genome copies in 100 ng of genomic DNA were determined by qPCR using the following primers and Taqman probe specific for BGH polyA in the vector genome: (TaqMan Probe, 6FAM-AGC ATT TTT TTC ACT GCA TTC TAG TTG TGG TTT GTC-TAMRA SEQ ID NO: 11). Samples with ≥100 vg genome copies per μg of DNA were deemed positive for vector genomes.

Microarray

Total RNA was isolated from biopsy punches using Trizol and further purified using RNeasy Plus Mini Kit, and its quality analyzed on an Agilent Bioanalyzer. Bioanalyzer RNA integrity number (RINs) values were 8.7-9.5, which indicates high quality RNA. Sample preparation and microarray hybridization was performed using Affymetrix Mouse Gene 2.0ST Arrays. Three independent samples were analyzed per group. Resulting data was processed and P values <0.05 and 1.5-fold change in relation to PBS controls were considered differentially expressed genes.

Quantification of GM1 Ganglioside Content

GM1 content in CNS was quantified by liquid chromatography tandem mass spectrometry(LC-MS/MS). Briefly, 25 ul of 0.01-0.04 mg/0 tissues were homogenized in 0.1M NaCl, 0.2M $CH_3COONa$ at pH=4.3, internal standard 3 μg of $d_3$-GM1 added, and gangliosides isolated through a modified Folch extraction. Samples were then run through a C18 column, dried and reconstituted in running buffer to then be processed through the LC-MS/MS, Waters Quattro Premier XE. Samples were separated at mass/charge ratio (m/z) of 290 and each GM1 species differing in fatty acid composition was quantified. GM1 content was determined by calculating the ratio of the sum of all species over $d_3$-GM1, and plotted against the ratio of purified GM1/$d_3$-GM1 from a standard curve. Samples were normalized for protein content in the initial lysate determined by Bradford assay and were reported as ng GM1/µg protein.

Example 2

AAV Dose Dependent Distribution of βgal in Brain

Figure 2D:
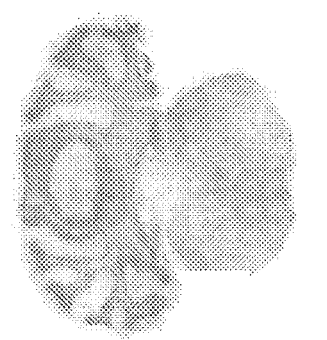
FIGS. 2A-2J show AAVrh8-mβgal intracranially injected in βgal$^{-/-}$ mice produces dose dependent enzyme distribution. βgal expression in the brain of representative AAVrh8-injected animals and age-matched controls was analyzed at 2 weeks (4e10vg) or 3 months (2.6e10vg and 2.6e9vg) post-injection by histochemical staining of 20 μm coronal brain sections with X-gal and counterstaining with Nuclear Fast Red.
Figure 2C:
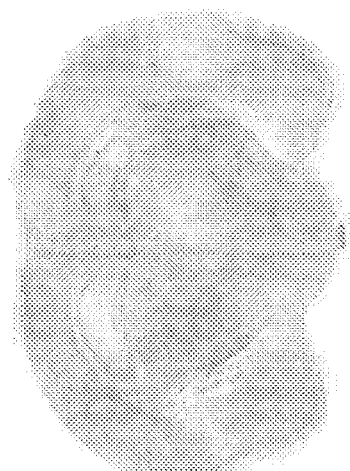
Figure 2B:
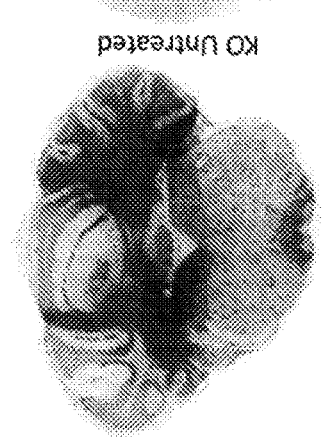
Figure 2A:
Figure 2H:
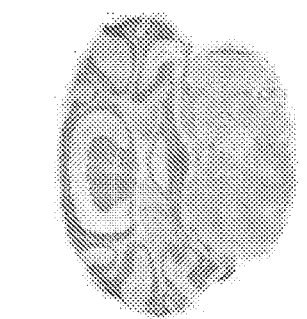
Figure 2G:
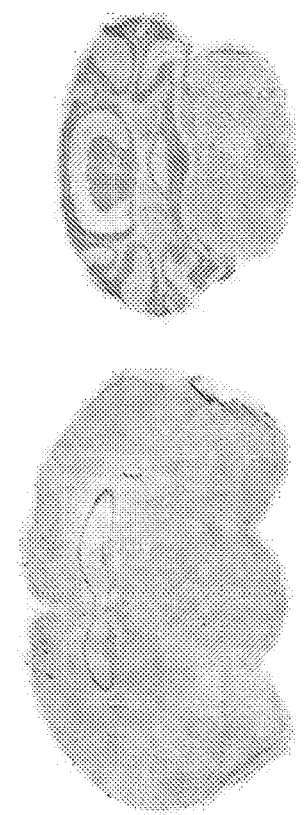
Figure 2F:
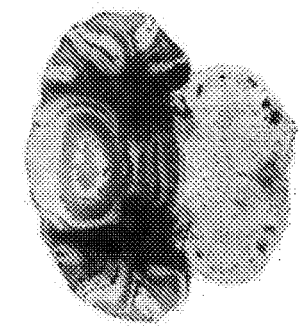
Figure 2J:
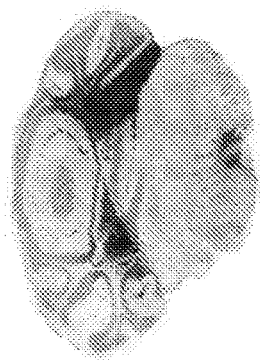
Figure 2E:
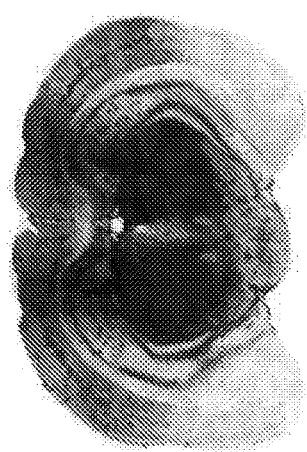
Figure 2I:
Figure 20:
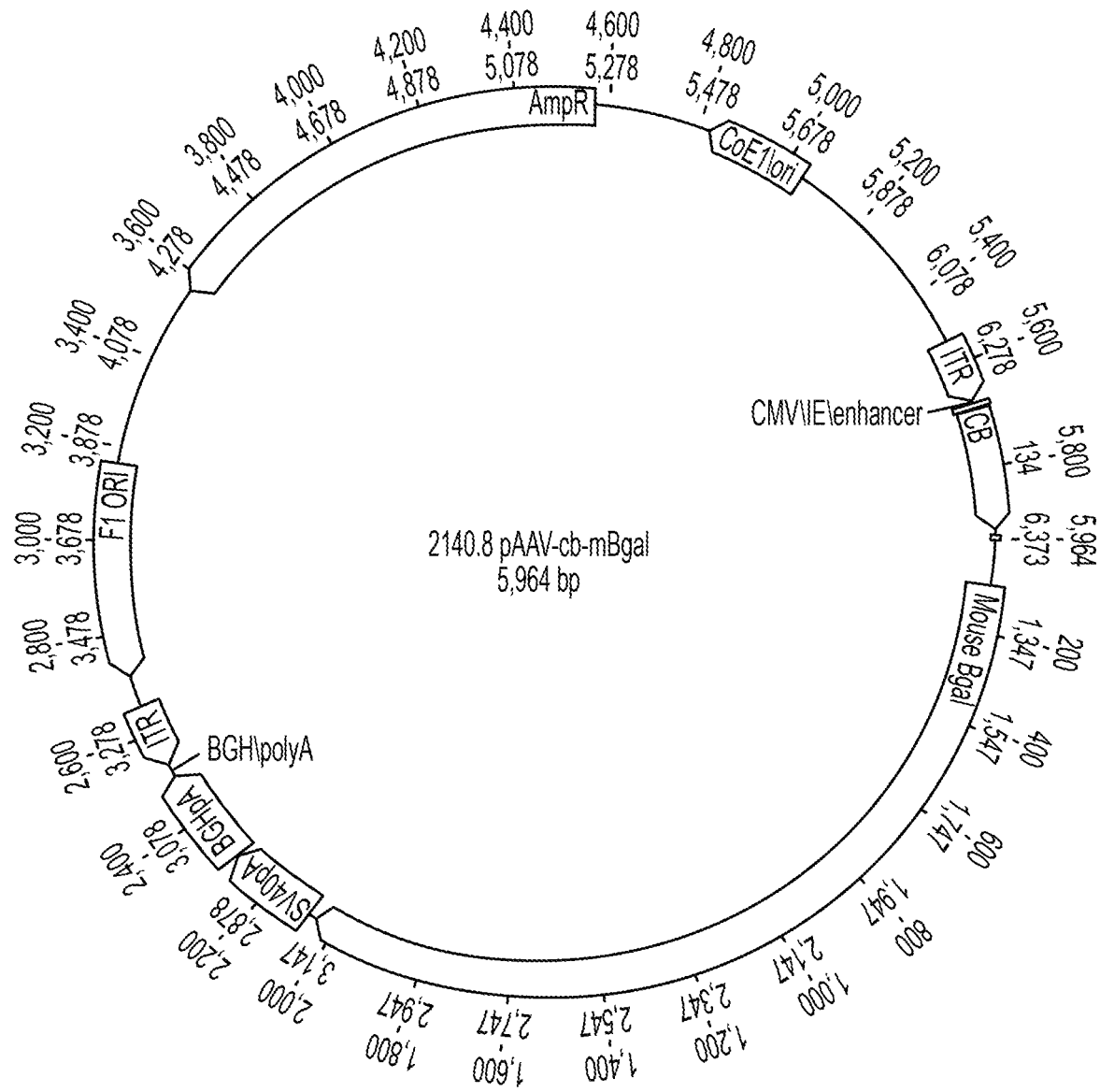
FIG. 20 shows a vector map of 2140.8 pAAV-cb-mβgal.
Figure 21:
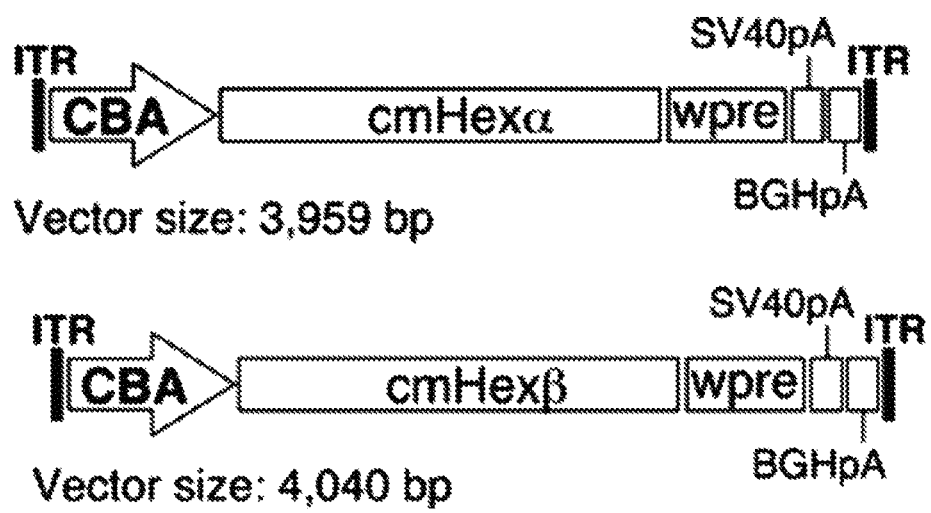
FIG. 21 shows the structure of monocistronic AAV vectors encoding HexA alpha- and beta-subunits.

AAVrh8-CBA-mβgal-WPRE vector (FIGS. 1 and 20) was infused into the brain of 6-8 week old GM1 gangliosidosis mice (βgal$^{-/-}$) by bilateral injections in the thalamus and deep cerebellar nuclei at total doses of 4e10vg, 2.6e10vg and 2.6e9vg. Animals in the highest dose cohort received bilateral injections of 1 µl in thalamus and DCN, while animals in the other two cohorts received 1 µl in thalamus and 0.3 µl in DCN. The βgal distribution pattern in brain at 3 months post-injection appeared to be dose dependent with the highest intensity of βgal activity at the injection site (FIG. 2). The highest dose (4e10vg) provided enzyme activity throughout much of the section in the cerebrum (FIG. 2A) and cerebellum (FIG. 2B). Middle dose, 2.6e10vg had similar level of activity in the cerebrum (FIG. 2E), and the cerebellum (FIG. 2F) appeared to provide slightly less activity but still spread of enzyme throughout the structure. Low dose, 2.6e9vg had less spread in both the cerebrum and cerebellum (FIGS. 2I & 2J, respectively).

AAV Treated Animals Retain Motor Function in a Dose Dependent Manner

Figure 3A:
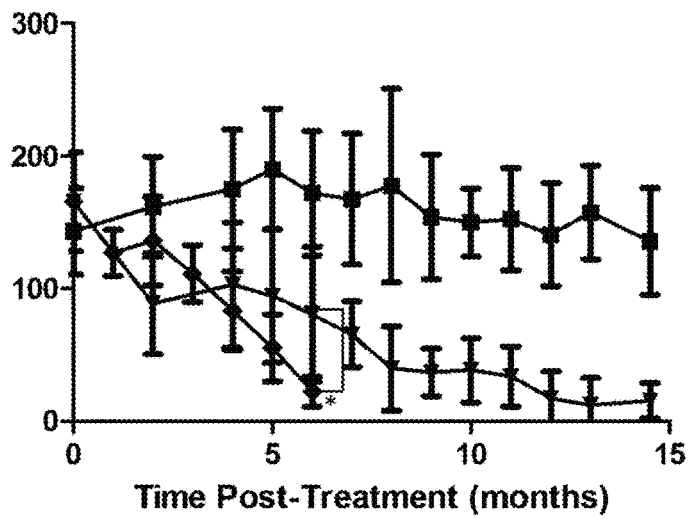
FIGS. 3A-3C show βgal$^{-/-}$ mice intracranially injected with AAV retain significant motor performance on the rotarod. Animals were assessed for motor function on an accelerating rotarod test (4-40 rpm over 5 minutes). Highest value from three trials was recorded. βgal$^{-/-}$ animals treated with a total dose of AAVrh8 vector of (FIG. 3A) 4e10vg.
Figure 3B:
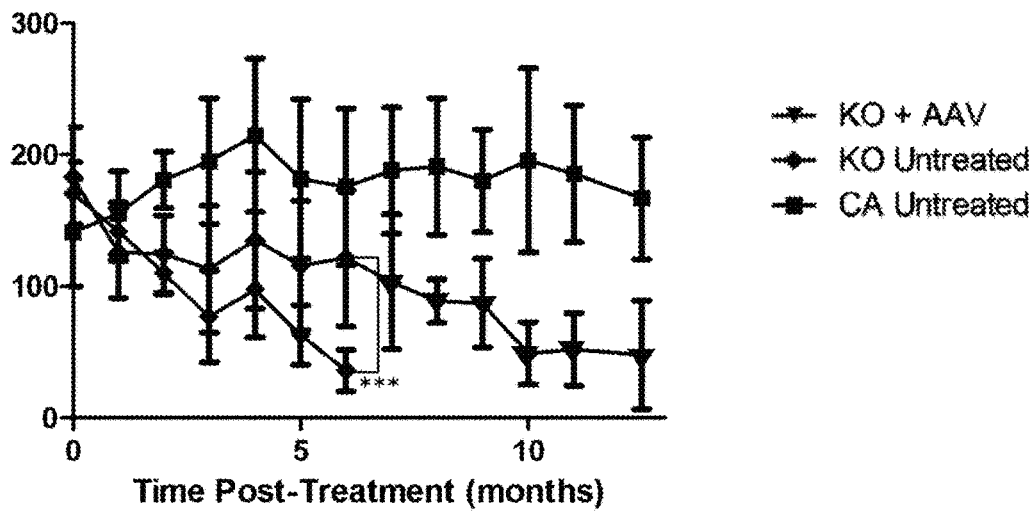
Figure 3C:
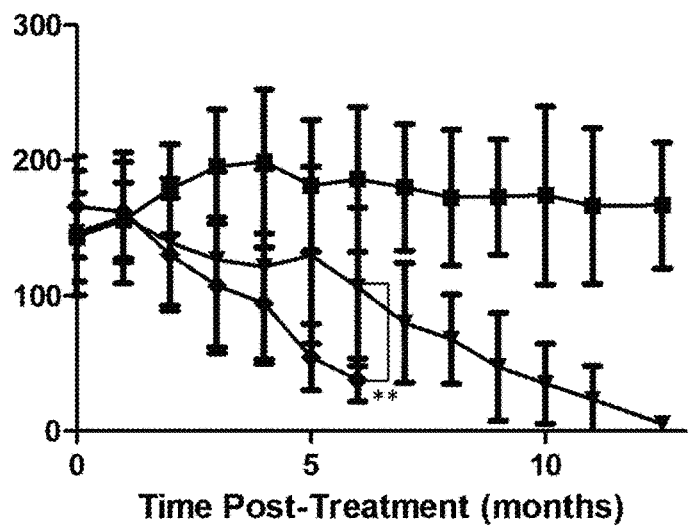

The motor function of AAVrh8-treated mice was assessed over time using the rotarod test (FIG. 3). All cohorts of AAVrh8-treated βgal$^{-/-}$ performed significantly better than untreated βgal$^{-/-}$ controls at the 6 month post-treatment time point (high dose 4e10vg p=0.006, middle dose 2.6e10vg p=0.0009, and low dose 2.6e9vg p=0.005). N=6-10 animals/group at 6 months post-treatment.

Example 3

AAV Treatment Extends Lifespan

Figure 4:
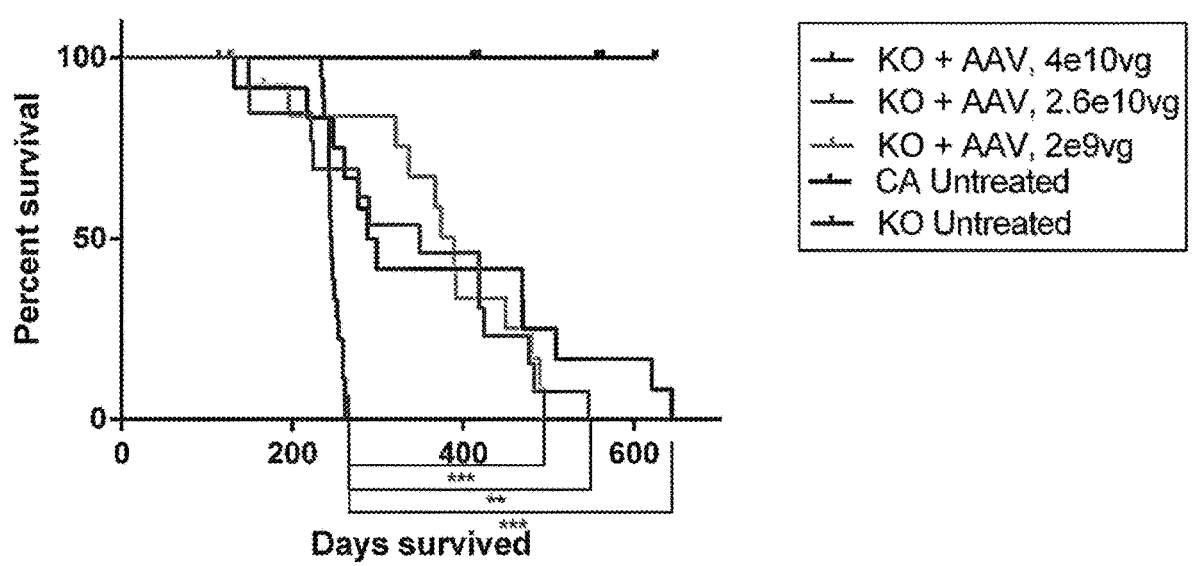
FIG. 4 shows AAV intracranially injected βgal$^{-/-}$ mice achieve significant extension in lifespan. Kaplan-Meier survival curves for intracranial AAVrh8 treated βgal$^{-/-}$ mice. Treated mice with a total dose of AAVrh8 vector of 4e10vg, 2.6e10vg and 2.6e9vg all had a significant extension of life span vs. naïve βgal$^{-/-}$ controls using Log-rank (Mantel-Cox) test (p=0.0004, 0.002, <0.0001 respectively). Median survival was increased from naïve βgal$^{-/-}$ controls (245.5 days, N=13) to 4e10vg cohort (293.5 days, N=12), 2.6e10vg cohort (349.0 days, N=13) and 2.6e9vg cohort (389.0 days, N=13).
Figure 6A:
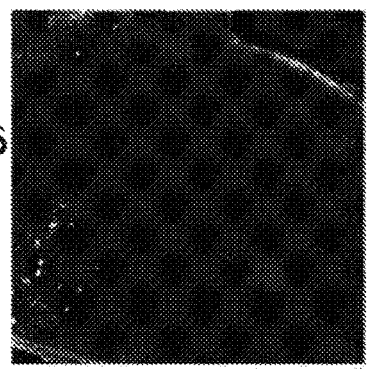
FIGS. 6A-6H show lysosomal storage persists in the spinal cords of long-lived AAV intracranial injected βgal$^{-/-}$ mice. Spinal cord sections cut at 20 μm were stained with Filipin for GM1-ganglioside storage. All long-lived animals showed some amount of clearance in the spinal cord, but also contained regions where clearance did not occur.
Figure 6B:
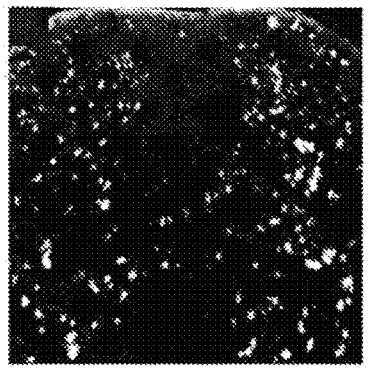
Figure 6C:
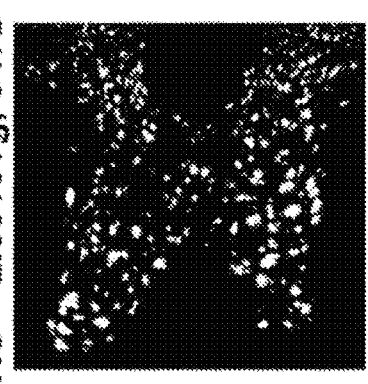
Figure 6D:
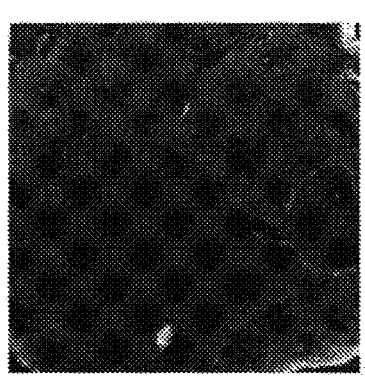
Figure 6E:
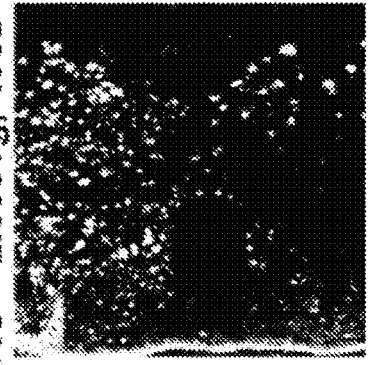
Figure 6F:
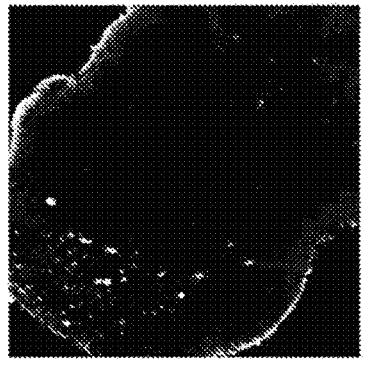
Figure 6G:
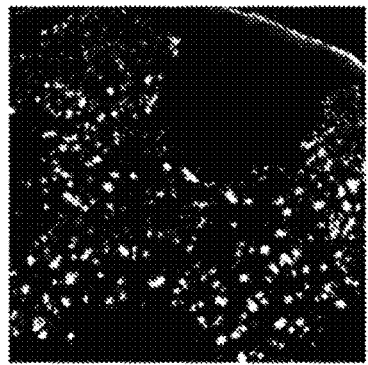
Figure 6H:
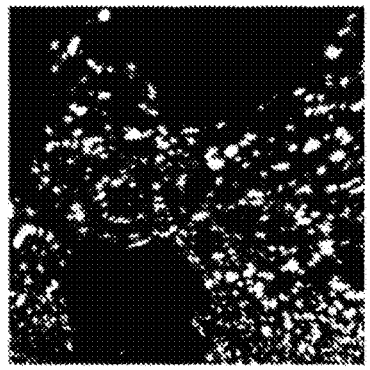

The lifespan of AAVrh8-treated βgal$^{-/-}$ mice was significantly increased compared to naïve βgal$^{-/-}$ controls (FIG. 4). Median survival for naïve βgal$^{-/-}$ controls was 245.5 days (N=18), 293.5 days for the 4e10vg cohort (N=12, p=0.0004), 349 days for the 2.6e10vg cohort (N=13, p=0.002) and 389 days for the 2.6e9vg cohort (N=12, p<0.0001).

GM1-Ganglioside Storage Persists at the Injection Site and in the Spinal Cord of Long-Lived AAV Treated Animals Histological analysis of lysosomal storage by Filipin staining in the CNS of animals at 3 months post injection revealed nearly complete correction in the brain and cerebellum that was corresponding to enzyme presence as seen in Xgal staining at the same time point (FIG. 2). Surprisingly Filipin-positive cells were only found at the injection sites, or along the injection track (FIG. 5C, 5E).

The presence of Filipin-positive cells in the thalamus of AAVrh8-injected βgal$^{-/-}$ mice was surprising as it is also the brain region that displays the most intense X-gal histochemical staining in the brain (FIG. 5A, boxes), which is a semi-quantitative indicator of high βgal enzyme activity. In the spinal cord of long-lived AAV-treated mice (495-612 days) the impact on lysosomal storage was variable ranging from regions with very few remaining Filipin-positive cells to regions with no apparent change compared to untreated βgal$^{-/-}$ controls (FIGS. 6A, 6D, 6F, and 6B, 6C, 6E, respectively).

Example 4

Neuropathology at the Injection Sites

Animals were histologically assessed with Hematoxylin & Eosin (H&E) after early loss or at 3 months post injection. These animals were found to have morphological changes at the injection site that correlated with dose. βgal$^{-/-}$+AAV 4e10vg at 2 weeks post injection demonstrated large amounts of changes in the thalamus such as vascular cuffing and the appearance of inflammation (FIG. 7A, 7B, thick and thin arrows, respectively), and in the DCN with vascular cuffing and apparent neuronal engulfment (FIG. 8A, thick arrow and 8B, arrow heads, respectively). In βgal$^{-/-}$+AAV 2e10vg at 3 months post-treatment thalamic alterations were also seen with vascular cuffing and inflammation (FIG. 7E, 7F, thick and thin arrows, respectively). However, βgal$^{-/-}$+ AAV 2e10vg dose in the DCN had less vascular cuffing only (FIG. 8E, thick arrow). In the lowest dose representative animal, βgal$^{-/-}$+AAV 2e9vg at 3 months post injection only very minimal inflammation was seen in the thalamus (FIG. 7J, thin arrow) and this effect was absent in the DCN (FIG. 8I, 8J). Neither vascular cuffing nor inflammation was seen in untreated βgal$^{-/-}$ controls (FIG. 7C, 7D and FIG. 8C, 8D) or in untreated βgal$^{+/-}$ controls (FIG. 7G, 7H and FIG. 8G, 8H).

High Levels of βgal Induce an Unexpected Response in Injected Brain Structure

Figure 9G:
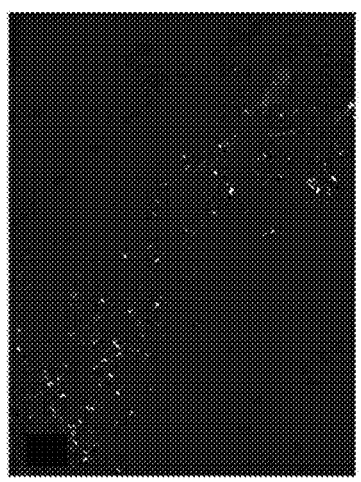
Figure 9H:
Figure 9I:
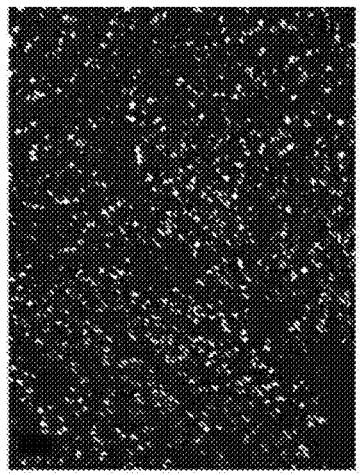
Figure 9J:
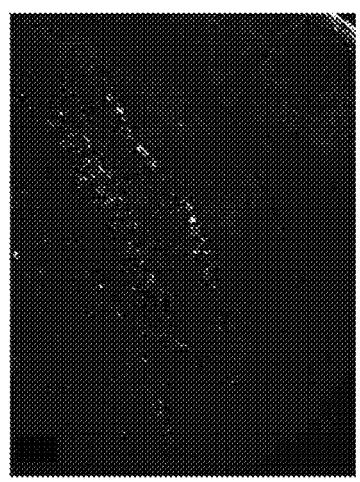
Figure 9K:
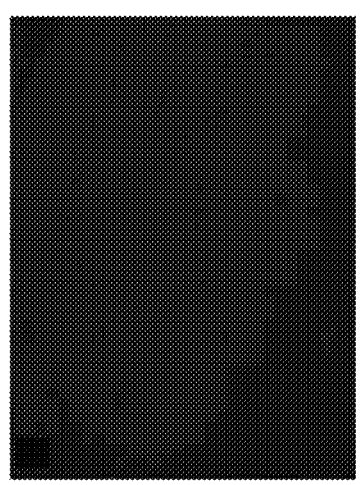
Figure 9L:
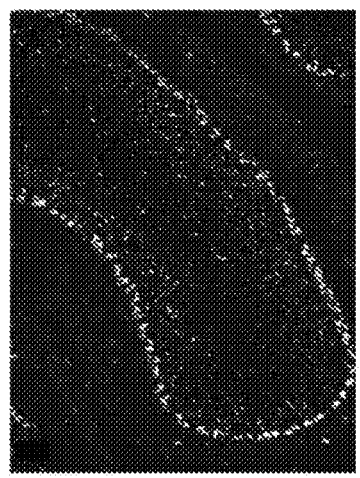

The paradoxical presence of Filipin-positive cells at the injection sites (FIG. 5C, 5E) may be the result of an unexpected response to AAV gene transfer in βgal$^{-/-}$ mice. To understand this phenomenon, normal, unaffected βgal$^{+/-}$ littermates were injected intracranially with AAVrh8 vector. Similar to the results in βgal$^{-/-}$ mice (FIG. 5C, 5E), large numbers of Filipin-positive cells were present in brain regions with the highest βgal staining intensity (FIG. 9A, 9B) in AAVrh8-injected βgal$^{+/-}$ mice (FIG. 9D, 9G, 9J). This result indicates that the presence of Filipin-positive cells in the targeted brain structures is an unexpected adverse response to an aspect of AAV gene transfer.

Example 5

Figure 19:
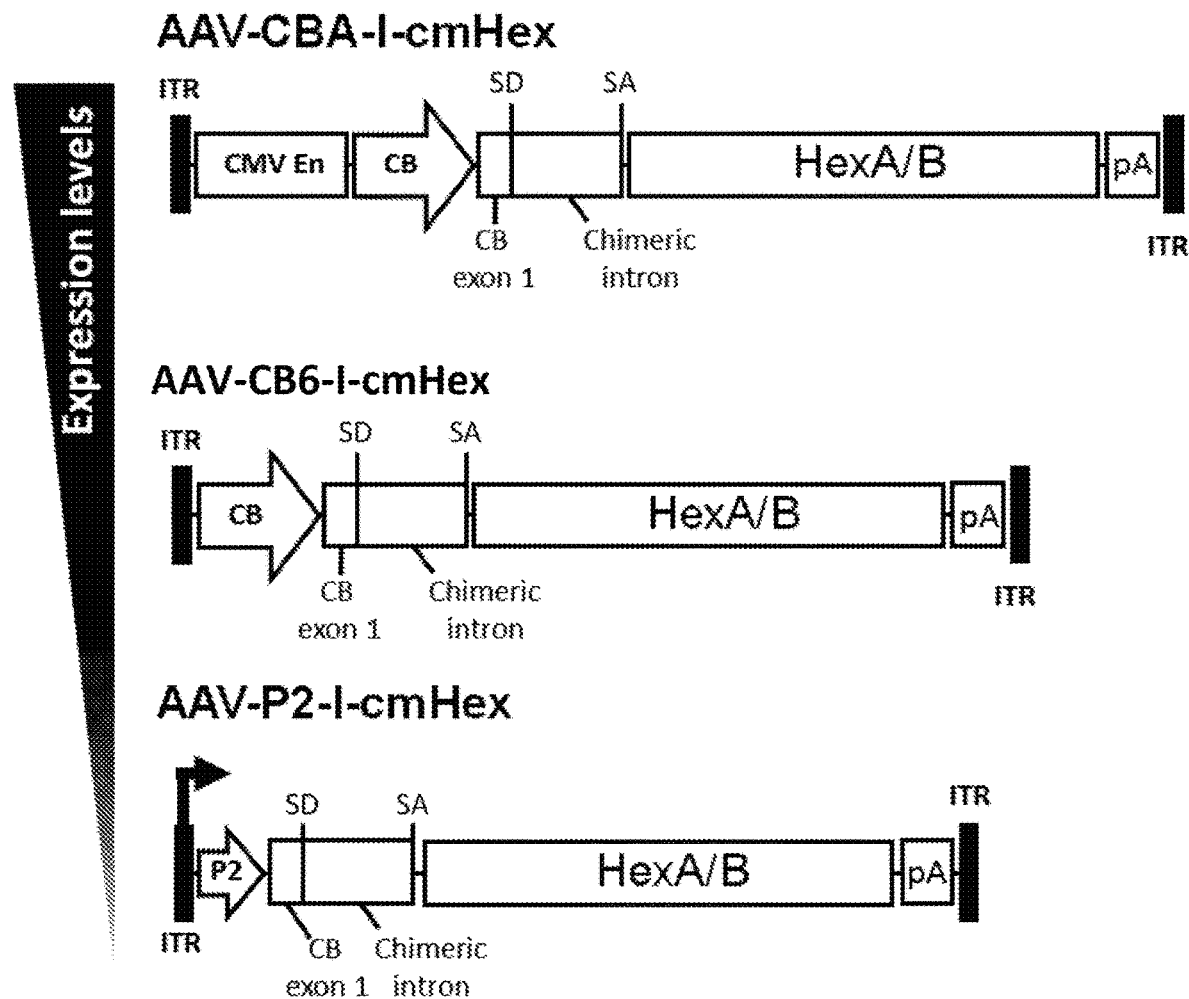
FIG. 19 depicts structures of AAVrh8 vectors.

Validation of AAVrh8 Vector Series to Assess Contribution of Enzyme Activity, Protein Levels, and AAVrh8 Capsid to Filipin-Detected Response A series of AAVrh8 vectors were designed to study the nature of the unexpected response at the injection sites (Table 1). Additional vectors that were designed are shown in FIG. 19. This series of AAVrh8 consisted in sequential removal of elements that influence transgene expression levels in the original vector, AAVrh8-CBA-mβgal-WPRE, which will be referred to as 'CBA-WPRE' from here on. In vector 2 'CBA', the woodchuck hepatitis virus post-transcriptional regulatory element (WPRE) was removed. Vector 3 'CBA-EI-WPRE' has the exact same backbone as vector 1 but encodes a βgal protein carrying an E269Q mutation in the putative active site. This vector was designed to assess whether the observed response was caused by enzymatic activity or protein production. Vector 4 'CB6' contained mβgal cDNA, but did not carry WPRE or the chimeric intron present in the other vectors. This vector was tested at two doses, 'CB6 Low' (same dose as all other vectors), and 'CB6 High' (2.0e10vg). Vector 5 'transgene empty' or 'T. Empty' contained all components of vector 1, but lacked the mβgal cDNA.

The newly constructed AAVrh8 vectors were injected bilaterally into the thalamus of normal βgal$^{+/-}$ mice (1 μl/site for total dose of 3.4e9vg), except the CB6 vector, which was also injected at a higher dose (1 μl/site for total dose of 2.0e10vg). Controls were βgal$^{+/-}$ mice injected with phosphate buffered saline (PBS), and naïve βgal$^{+/-}$ mice. Enzyme activity and protein production in the thalamus were measured by 4-methylumbelliferyl (4-MU) biochemical assay and western blot 6 weeks after injection (FIG. 10).

TABLE 1

Figure 11:
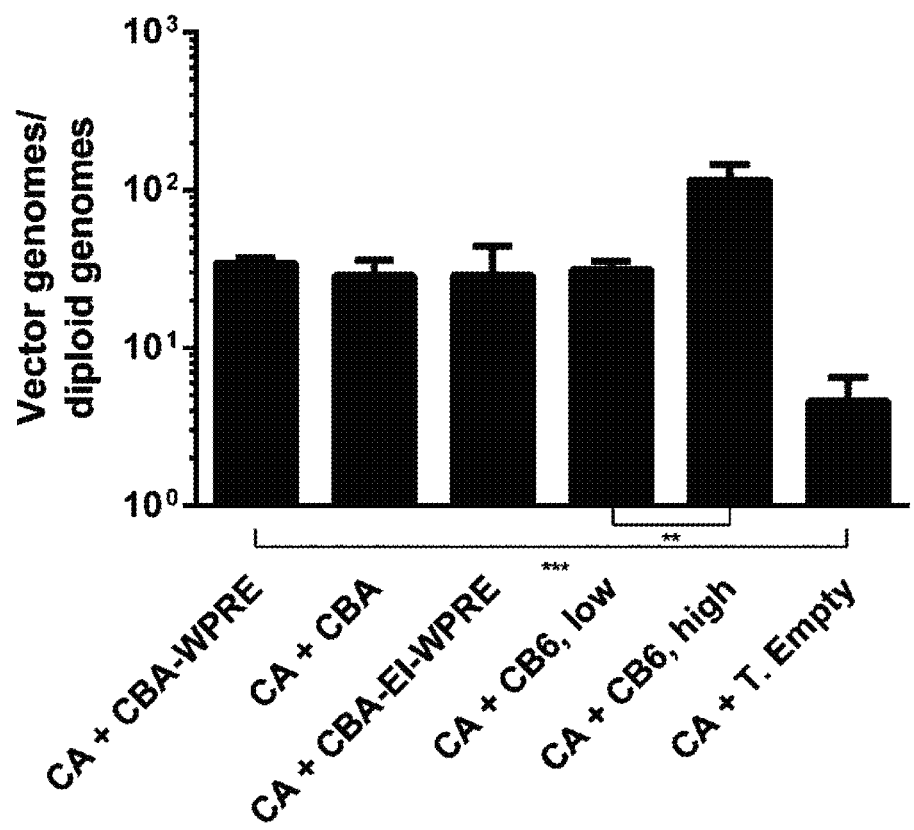
FIG. 11 shows vector genome presence in injected structure biopsy punches in βgal$^{+/-}$ mice. Vector genomes per diploid genome in a 2 mm×2 mm biopsy punches in injected structure where 10 of AAVrh8-vector (total dose 3.4e9vg, or 2.0e10vg, CBA High only) bilateral into the thalamus of βgal$^{+/-}$ mice (CA+vector name) as determined by qPCR to the SV40 poly A on the transgene. Samples were taken at 6 weeks post injection. Error bars represent mean+SD, N=3/group, and * indicates significant difference indicated by connecting line and using unpaired multiple T tests (Holm-Sidak) where *=p<0.05, =p<0.01 and *=p<0.001.
Figure 12M:
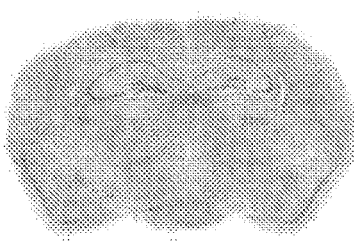
FIGS. 12A-12U show vectors with decreasing protein presence lead to decrease in Filipin positive regions in βgal$^{+/-}$ mice. Coronal sections of mouse brain stained with Xgal for βgal enzyme presence and counterstained with Nuclear Fast Red at 6 weeks post injection in (FIG. 12A, FIG. 12D, FIG. 12G, FIG. 12J, FIG. 12M and FIG. 12P) in representative βgal$^{+/-}$ (CA+vector name) injected with 10 of AAVrh8-vector (total dose 3.4e9vg, or 2.0e10vg in the CBA High only) bilaterally into the thalamus or βgal$^{+/-}$ un-injected (CA Untreated).
FIG. 12B, FIG. 12E, FIG. 12H, FIG. 12K, FIG. 12N and FIG. 12Q show Filipin staining in parallel sections of the same animals in (FIG. 12A, FIG. 12D, FIG. 12G, FIG. 12J, FIG. 12M and FIG. 12P).
FIG. 12C, FIG. 12F, FIG. 12I, FIG. 12L, FIG. 12O and FIG. 12R show ToPro3 nuclear stain in parallel sections of the same animals in (FIG. 12A, FIG. 12D, FIG. 12G, FIG. 12J, FIG. 12M and FIG. 12P). Boxes represent approximate location of Filipin and ToPro3 staining on brain sections taken at 20× magnification. Scale bar=250 μm. Images are representative of N≥2 mice/group.
Figure 12N:
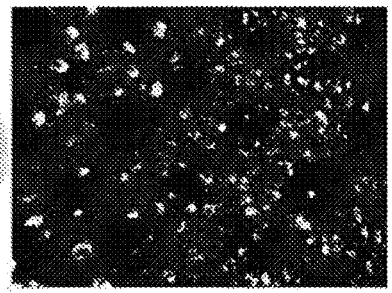
Figure 12O:
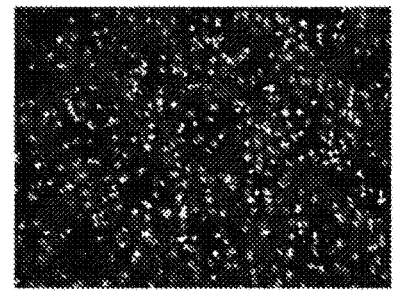
Figure 12P:
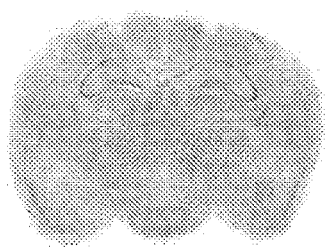
Figure 12Q:
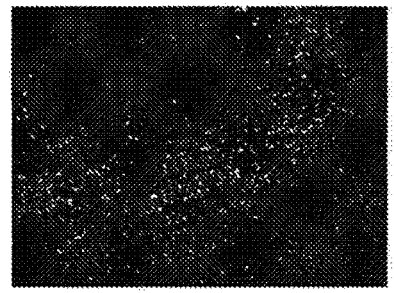
Figure 12R:
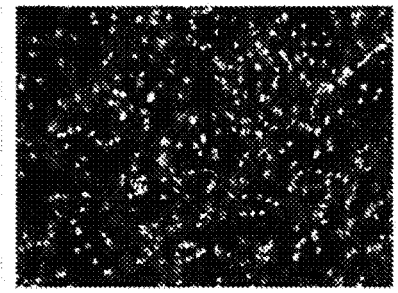
Figure 12S:
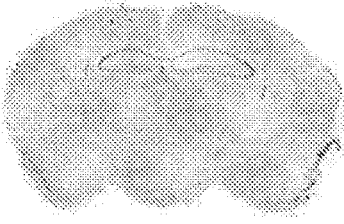
Figure 12T:
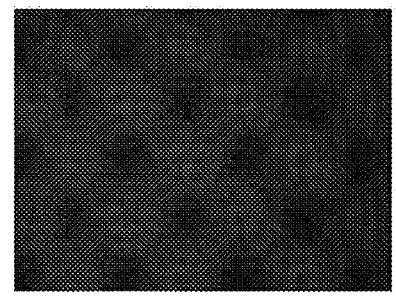
Figure 12U:
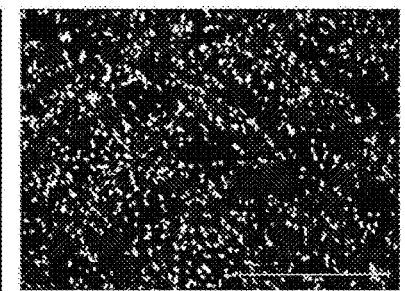

List of alterations in vectors designed to evaluate storage biomarker Filipin persistence 1) CBA-mβgal-WPRE, CBA-WPRE - original vector
2) CBA-mβgal (no WPRE), CBA - decrease enzyme expression
3) CBA-enzyme inactive mβgal-WPRE, CBA-EI-WPRE - eliminate enzyme function
4) CB6-mβgal (no WPRE), CB6 - further decrease enzyme expression
5) Transgene empty, T. Empty - eliminate protein expression
6) PBS injection, PBS - control for surgery
7) Untreated βGal$^{+/-}$, CA Untreated The CBA-WPRE vector generated the highest enzyme activity at 686 fold above that in thalamus of naïve βgal$^{+/-}$ mice (FIG. 10A), and corresponding elevation in protein (FIG. 10B, lane 1). The CBA vector resulted in βgal activity 224 fold over βgal$^{+/-}$ level, which was significantly lower than that obtained with CBA-WPRE vector (FIG. 10A, p=0.001) and an apparent corresponding decrease in protein product (FIG. 10B, lane 2). In thalami of mice injected with CBA-EI-WPRE vector the βgal activity was comparable to that in naïve control mice (FIG. 10A), but the protein was expressed at comparable levels to those in CBA-WPRE injected thalami (FIG. 10B, lane 3 vs. lane 1). Therefore, the E269Q mutation abrogates enzyme activity but does not seem to affect protein expression levels. Injection of CB6 vector at the same dose as the other vectors (CB6-Low) resulted in βgal activity 54 fold above over βgal$^{+/-}$ level (FIG. 4A), and protein presence at a correspondingly lower amount that with the other vectors (FIG. 10B, lane 4). Injection of this vector at higher dose (CB6-High) resulted βgal activity 420 fold above over βgal$^{+/-}$ level, which is significantly higher than in the CB6-Low cohort (FIG. 10A, 10B, p=0.03). The βgal activity level in the CB6-High cohort was comparable to that measured in the CBA-WPRE cohort, and appeared similar in protein levels (FIG. 10A, 10B, lane 1 vs. lane 5). The thalami of animals injected with transgene empty vector (T. Empty) or PBS showed no change in βgal activity or protein level compared to naïve βgal$^{+/-}$ levels (FIG. 10A, 10B). The number of vector genome copies in AAV-injected thalami were shown to be comparable in most cohorts injected with a total dose of 3.4e9 vg, except in the T.empty cohort (FIG. 11). As expected, the CB6-High cohort infused with 2.0e10 vg showed significantly increased number of vector genome copies (FIG. 11).

Filipin-Detected Response Correlates with Protein Levels

The brains of AAVrh8-injected and control βgal$^{+/-}$ mice were analyzed for βgal enzymatic activity by Xgal staining (FIG. 12A, 12D, 12G, 12J, 12M, 12P, 12S) and for presence or absence of Filipin-positive cells in the thalamus (FIG. 12B, 12E, 12H, 12K, 12N, 12Q, 12T). The thalamic regions with the most intense βgal staining (FIG. 11A, 11D) also contained Filipin-positive cells in CBA-WPRE and CBA injected animals, albeit at apparently lower numbers in the latter cohort (FIG. 11B, 11E). The thalami in the CBA-EI-WPRE cohort had large numbers of Filipin-positive cells, but no active βgal enzyme (FIG. 11K, 11J, respectively). Similar Filipin staining was apparent in the thalami of T-empty and CB6-low cohorts (FIG. 11K, 11Q), but it appeared as small puncta distinct from the pattern observed in the CBA-WPRE and CBA-EI-WPRE cohorts. Filipin staining was also observed in the thalami of CB6-High cohort and the pattern appeared a mix of that observed in the CBA-WPRE and CB6-Low cohorts (FIG. 11H). These results suggest the abnormal Filipin accumulation at the injection site is related to protein expression levels and not enzyme activity.

Figure 13:
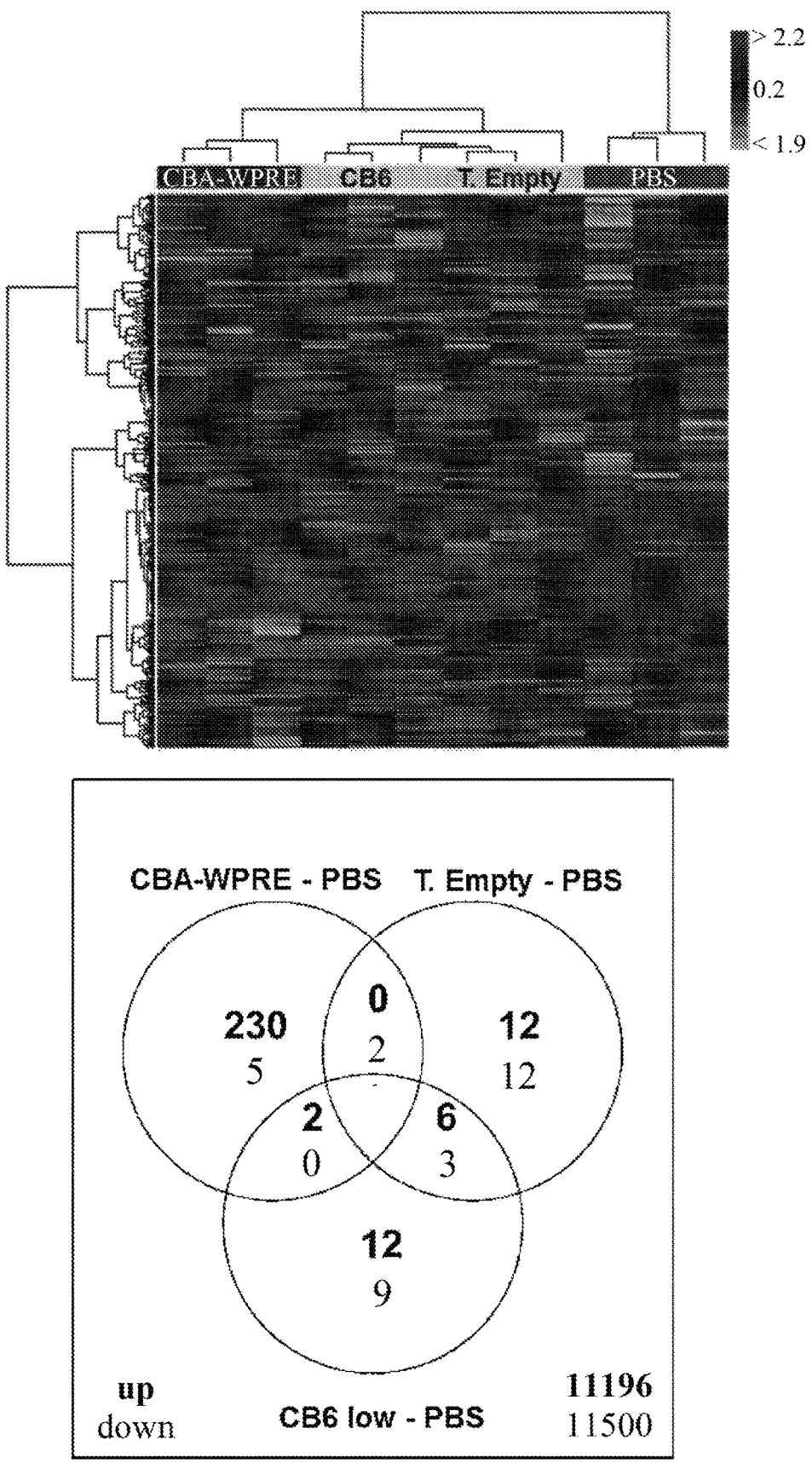
FIG. 13 shows a clustering heatmap and a Venn diagram of all differentially expressed genes in βGal$^{+/-}$ mice demonstrate transgene expression dependent variation. The Heatmap and Venn diagram of all differentially expressed genes was produced using data from a 2 mm×2 mm biopsy punch of thalamus injected with 1 μl of AAVrh8-vector (3.4e9vg total dose) or mock treated with PBS bilaterally, at ~6 weeks post injection in βgal⁺/⁻ mice (CA+vector name). Microarray results determined by Affymetrix Mouse Gene 2.0ST, N=3/group, P<0.05 and >1.8 fold change.

Transcriptomic Changes in Injected Thalami Correlate with Filipin-Detected Abnormal Response Microarray analysis was performed in the thalami to further characterize the tissue response to the physiological change induced by gene transfer. Total thalamic RNA was isolated from CBA-mβgal-WPRE, CB6-Low, T.Empty and PBS-injected cohorts. Transcriptomic changes (fold change>1.8-fold, p<0.05) for all samples analyzed are represented in a heat map (FIG. 13A). CB6-low and T.Empty samples cluster together with PBS, and are different from CBA-WPRE samples. The number of genes with >2-fold change in expression levels (p<0.05) is considerably larger in CBA-WPRE samples compared to CB6 and T.Empty with a few overlapping genes (FIG. 13B). A number of genes up-regulated in the CBA-WPRE samples are characteristic of activated microglia and reactive astrocytes (Table 2). None of these genes showed significant changes in CB6 or T.Empty samples.

TABLE 2

Select genes upregulated in microarray analysis of CBA-WPRE vector.
Fold change is CBA-WPRE vector over PBS.
Genes upregulated in CBA-WPRE

| Gene | Gene name | Function | Fold change | Reference |
|---|---|---|---|---|
| Serpina3n | serine (or cysteine) peptidase inhibitor, clade A | Peptidase inhibitor, response to cytokine, marker of reactive gliosis | 1.9 | Winkler et al, 2005; Zamanian et al, 2012 |
| Gbp3 | guanylate binding protein 3 | Response to interferon β, response to interferon γ, upregulated in LPS reactive astrocytes | 3.2 | Burckstummer et al, 2009; Degrandi et al, 2007; Zamanian et al, 2012 |
| B2m | beta-2-microglobulin | Antigen processing and presentation, cellular defense response, upregulated in LPS reactive astrocytes | 2.2 | Uginovic et al, 2005; Zijilstra et al, 1989; Zamanian et al, 2012 |
| Cd86 | Cd86 antigen | Costimulatory ligand, upreglated in SOD1$^{G93A}$ microglia | 2.3 | Chiu et al, 2013 |
| Trem2 | triggering receptor expressed on myeloid cells 2 | Transmembrane protein - triggers myeloid cells, increase phagocytic | 3.0 | Melchior et al, 2010; Trash et al, 2009; Chiu et al, 2013 |

TABLE 2-continued

Select genes upregulated in microarray analysis of CBA-WPRE vector.
Fold change is CBA-WPRE vector over PBS.
Genes upregulated in CBA-WPRE

| Gene | Gene name | Function | Fold change | Reference |
|------|-----------|----------|-------------|-----------|
|  |  | activity, supress cytokine production, upregulated in SOD1$^{G93A}$ microglia |  |  |
| C1qa | complement component 1, subcomponent, alpha polypeptide | Complement activiation, upreglated in SOD1$^{G93A}$ microglia | 3.0 | Azeredo da Silveira et al, 2002; Chiu et al, 2013 |
| Gfap | glia fibrillary acidic protein | Marker of reactive gliosis, upregulated in SOD1$^{G93A}$ microglia | 3.6 | Jessen & Mirsky, 1980; Chiu et al, 2013 |
| Cybb | cytochrome b-245, beta polypeptide | Proinflammatory oxidase, upreglated in SOD1$^{G93A}$ microglia | 4.8 | Harraz et al, 2008; Chiu et al, 2013 |

Example 6

Therapeutic Impact of Different AAVrh8 Vectors in GM1-Gangliosidosis Mice

Figure 14:
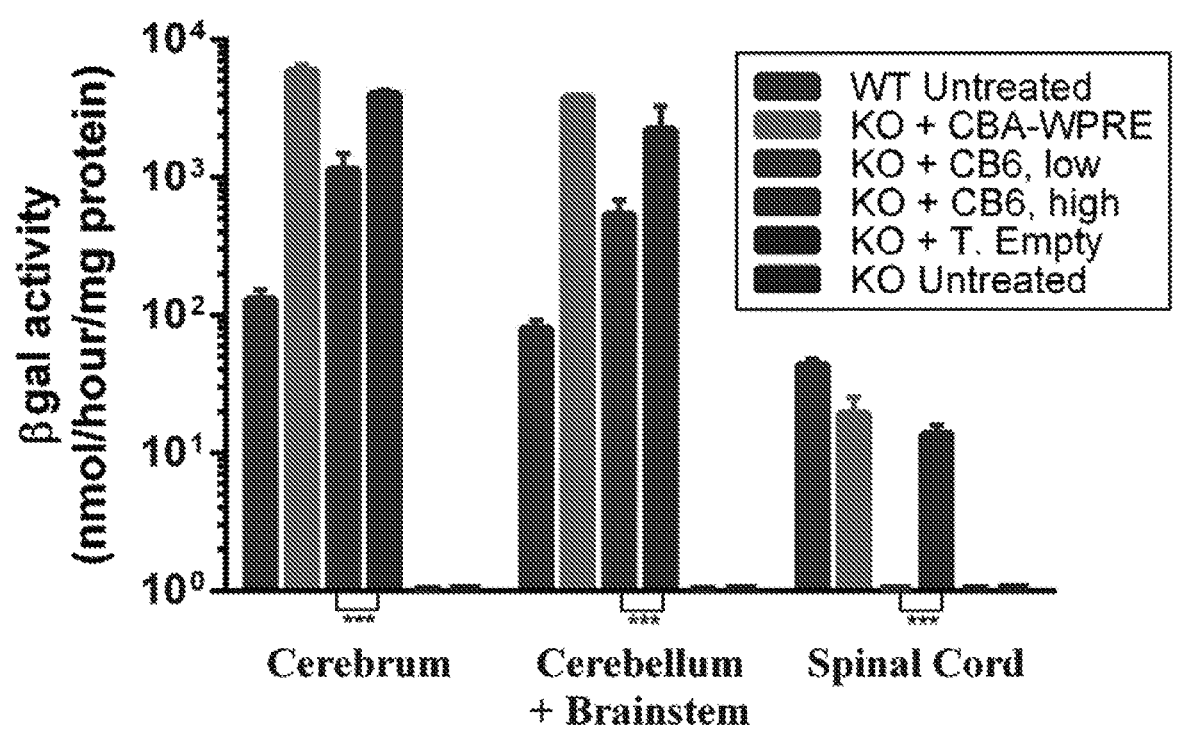
FIG. 14 shows βgal enzyme activity in the CNS of treated βgal⁻/⁻ mice result in varied distribution of enzyme throughout structures. βgal enzyme activity in cerebrum, cerebellum+brainstem or spinal cord of βgal⁻/⁻ injected bilaterally 10 into the thalamus and 0.3 ul in the DCN of AAVrh8-vector (total dose 3.4e9vg, or 2.0e10vg, CBA High only) or untreated (KO Untreated) or βgal⁺/⁺ mice untreated (WT Untreated), as determined by 4-MU assay at ~6 weeks post injections. Enzyme activity is normalized to protein concentration by Bradford, and is reported as nmol/hour/mg protein. Values represent mean+SD, N=3/group, and * indicates significant difference of βgal⁻/⁻+AAVrh8-CB6 vector (total dose 3.4e9vg, KO+CB6 Low) vs. βgal⁻/⁻-+AAVrh8-CB6 vector (total dose 2.0e10vg, KO+CB6 High). P value calculated using unpaired T tests (Holm-Sidak) where ***=p<0.001.

From the studies performed in βgal$^{+/-}$ mice above, a correlation was determined that reduced protein expression from the transgene could reduce the pathological transcription level changes in the injected structure. We then sought to determine if the changes in AAV vector design translated into differences in therapeutic outcome in GM1-gangliosidosis mice (βgal$^{-/-}$). Six to eight week old βgal−/− mice received bilateral injections of AAV vector into thalamus (1 µl/side) and deep cerebellar nuclei (0.3 µl/side) and the outcomes measured at ~6 weeks post-injection. Study cohorts were βgal−/− mice injected with CBA-WPRE, CB6 (CB6-Low), and Transgene Empty vectors administered at a total dose of 4.4e9vg. In addition, CB6 was injected at a total dose of 2.6e10vg (CB6-High). Naïve untreated βgal−/− and βgal+/+ animals were used as controls. Evaluation of βgal activity by 4-MU assay of the CNS (FIG. 14) showed that in the cerebrum CBA-WPRE was 45-fold higher than wild type level (FIG. 14), where CB6 Low was 9-fold higher (FIG. 14) and CB6 High was 30-fold higher (FIG. 14). As expected T.Empty and untreated cohorts of βgal−/− mice had no detectable βgal activity in any CNS region analyzed (FIG. 14). In the cerebellum+brainstem the trend was the same, with CBA-WPRE at 47-fold (FIG. 14), CB6-Low at 6-fold (FIG. 14), and CB6-High at 27-fold above wild type level (FIG. 14). Interestingly, in the spinal cord CBA-WPRE was only 50% of wild type level (FIG. 14), CB6-High was 30% (FIG. 14), and CB6-Low had no detectable activity (FIG. 14). In all CNS tissues analyzed, CB6-High was significantly higher (p<0.001) in βgal activity than the same vector injected at the lower dose, CB6-Low.

The βgal distribution pattern in the brain as demonstrated by histological stain X-gal (FIG. 15) correlated with the activity levels in the cerebrum or cerebellum+brainstem determined by the 4-Mu assay (FIG. 14). The CBA-WPRE vector resulted in dark blue staining in thalamus and DCN and widespread distribution of detectable enzyme activity throughout the brain (FIG. 15A). In contrast, in the CB6-Low cohort (FIG. 15B) there was intense staining in thalamus and DCN but lower detectable levels throughout the cerebrum, cerebellum or brainstem. In CB6-High animals, the βgal pattern of distribution in brain appeared broader than in CB6-Low animals (FIG. 15C). As anticipated, there was no evidence of increased βgal activity in T.Empty (FIG. 15D) and naïve βgal$^{-/-}$ mouse cohorts (FIG. 15E).

Figure 16:
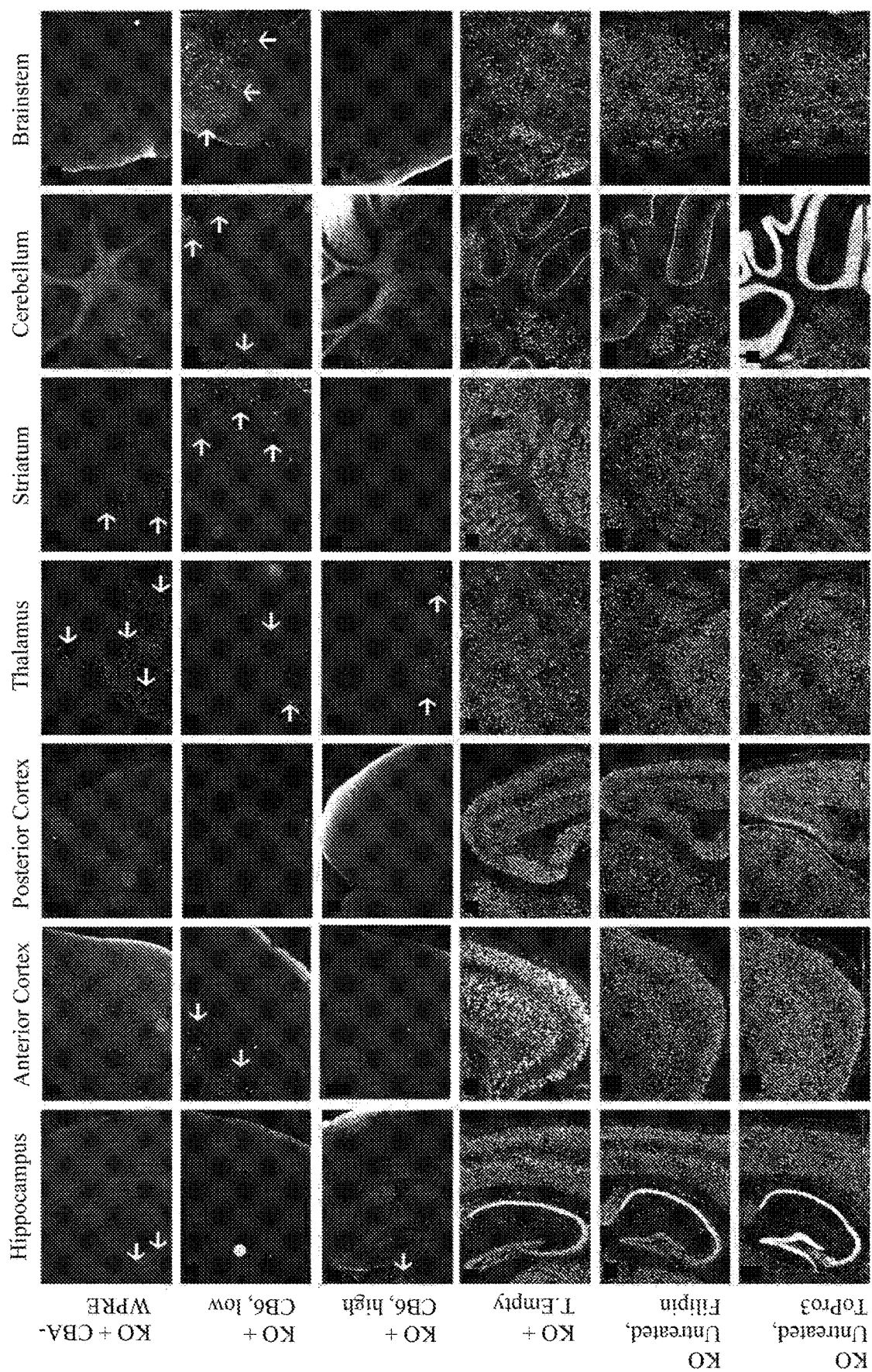
FIG. 16 shows Filipin staining for GM1-ganglioside content in the brain of βgal⁻/⁻ mice after therapeutic AAVrh8 treatment. Sagittal sections of mouse brain stained with Filipin for GM1 content or nuclear stain ToPro3 (KO Untreated, ToPro3, bottom row) at 6 weeks post injection in a representative βgal⁻/⁻ injected bilaterally with 10 into the thalamus and 0.3 ul in the DCN of AAVrh8-vector (total dose 3.4e9vg, or 2.0e10vg, CBA High only), or untreated (KO Untreated). N=2-3/group. Images taken at 5×, scale=100 mm.

Histological analysis of lysosomal storage in brain and spinal cord using Filipin staining (FIG. 16) correlated with the βgal activities (FIG. 14) and distribution patterns (FIG. 15) described above. In CBA-WPRE injected animals, there was nearly complete clearance of storage throughout the brain (FIG. 16), except at the injection site and track with Filipin-positive cells in ventral hippocampus and throughout the thalamus (FIG. 16; 1$^{st}$ row, 4$^{th}$ column). Storage clearance in the CB6-Low cohort appeared less efficient (FIG. 16; 2$^{nd}$ row) as Filipin-positive cells were still present in anterior cortex, striatum and brainstem (FIG. 16; 2$^{nd}$ row, column 2, 5, 7 respectively). At the higher dose (CB6-High) the efficiency of CB6 vector was very high with resolution of lysosomal storage throughout the brain (FIG. 16; 3$^{rd}$ row). As before, Filipin-positive cells were present in ventral hippocampus and dorsal thalamus, however less than in CBA-WPRE (FIG. 16; 3$^{rd}$ Row, 1$^{st}$, 4$^{th}$ columns). The T.Empty cohort (FIG. 16, 4$^{th}$ row) showed no change in lysosomal storage compared to βgal$^{-/-}$ untreated controls (FIG. 16; 5$^{th}$ row).

The spinal cords of AAV-treated animals were also evaluated for storage content by Filipin staining. Spinal cords in CBA-WPRE animals had almost no remaining storage in the cervical region however, the thoracic region only showed minimal reduction (FIG. 17A-17B, respectively, arrows). Spinal cords in CB6-Low animals had almost no distinguishable reduction in storage compared to untreated controls (FIG. 17C-17D). Spinal cords in CB6-High animals were nearly devoid of lysosomal storage in cervical and thoracic regions (FIG. 17E-17F, arrows). As anticipated, the spinal cords of T.Empty animals showed no change in lysosomal storage compared to untreated βgal$^{-/-}$ control. (FIG. 17G-17H; 17I-17J, respectively).

Figure 18:
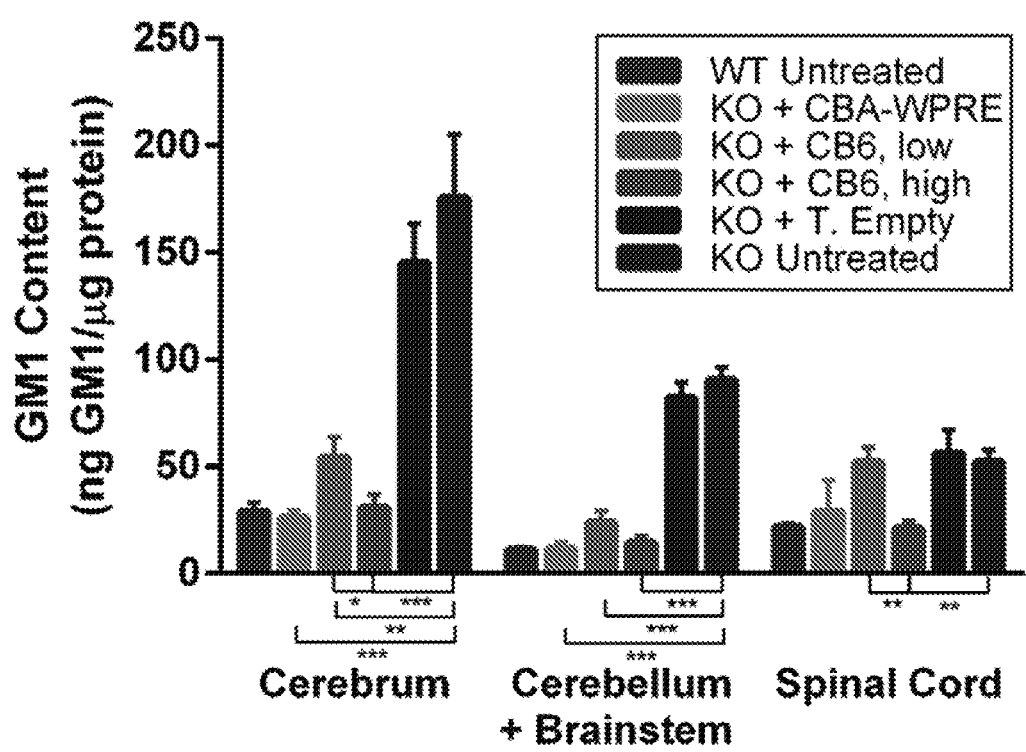
FIG. 18 shows therapeutic treatment using AAVrh8 in the CNS of βgal⁻/⁻ mice results in normalization of GM1 content when treated with a lower expressing promoter at a higher dose. GM1 content as quantitated by LC-MS/MS in cerebrum, cerebellum+brainstem or spinal cord of mice at. 6 weeks post injection in βgal⁻/⁻ injected bilaterally with 10 into the thalamus and 0.3 ul in the DCN of AAVrh8-vector (total dose 3.4e9vg, or 2.0e10vg for the CBA High group only), untreated (KO Untreated), or βgal⁺/⁻ untreated (WT Untreated). GM1 content represented as ng GM1/μg protein. Values represent mean+SD, N≥3/group and * indicates significant difference of KO+AAVrh8 vs. KO+PBS, or as indicated by connecting line, using multiple T tests (Holm-Sidak) where *=p<0.05, =p<0.01, and *=p<0.001.

GM1 ganglioside level in CNS was quantified by LC-MS/MS (FIG. 18). In CBA-WPRE and CB6-Low cohorts there was significant reduction in GM1 ganglioside content in comparison to untreated βgal$^{-/-}$ controls in cerebrum (p=0.0009 and p=0.002, respectively) and cerebellum+brainstem (p<0.0001 and p=0.0001, respectively). There was no significant change in GM1 ganglioside content in the spinal cord in either cohort. In the CB6-High cohort the GM1 ganglioside level was normalized in all CNS areas investigated cerebrum, cerebellum+brainstem, and spinal cord (FIG. 18, p=0.64, p=0.06 and p=0.79 respectively). As anticipated, there was no change in GM1 ganglioside content anywhere in CNS in the T.Empty cohort compared to naïve βgal$^{-/-}$ controls (FIG. 18).

Example 7

AAV-Mediated Gene Delivery to the CNS in Animal Models of GM2-Gangliosidoses

Prior to conducting a clinical trial in Tay-Sachs disease patients, a final safety study was performed in non-human primates. This study was designed to be a single dose (based on the prior studies in GM2 mice and cats; total vector dose of 3.2E12 vg) study with different endpoints to demonstrate safety of the injection procedure consisting of bilateral injection of AAVrh8 vector formulation into the thalamus and one cerebral lateral ventricle.

The first NHPs injected with the AAVrh8 formulation (N=3) developed moderate to severe neurological symptoms within 28 days post-injection. NHPs were euthanized and histological assessment of the CNS revealed large areas of necrosis and myelin loss in the thalamus along what appears to be the injection track (FIG. 22A-22D). In contrast, an NHP injected with saline showed no symptoms and there was no evidence of neuropathology at necropsy (>90 days post-injection) (FIG. 22F). In addition to histopathological assessment of the brain, Hexosaminidase activity was measured 6- to 48-fold above normal activity (FIG. 24).

Figures 23A, 23B:
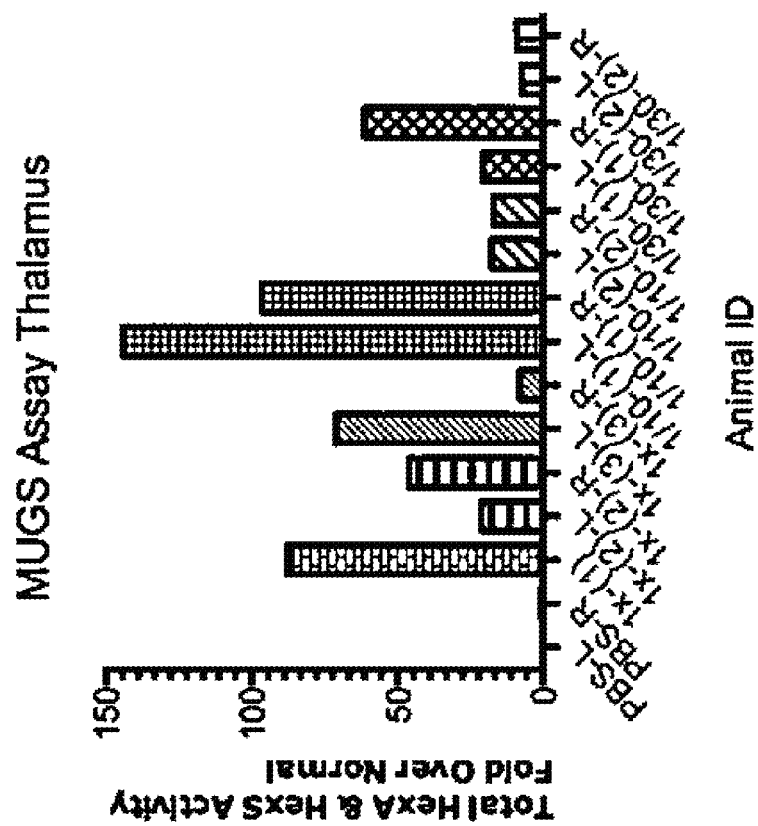
FIGS. 23A-23D show Hexosaminidase activity in the CNS. Hex activity was measured in the thalamus and thoracic spinal cord of NHP injected with different doses of 1:1 formulation of AAVrh8 vectors encoding cmHex-alpha and cmHex-beta. Two artificial substrates were used in the biochemical assays, namely MUG and MUGS. The first substrate is cleaved by all Hex isozymes (HexA, HexB, HexS), while the latter is cleaved only by HexA and HexS isozymes.
Figure 23C:
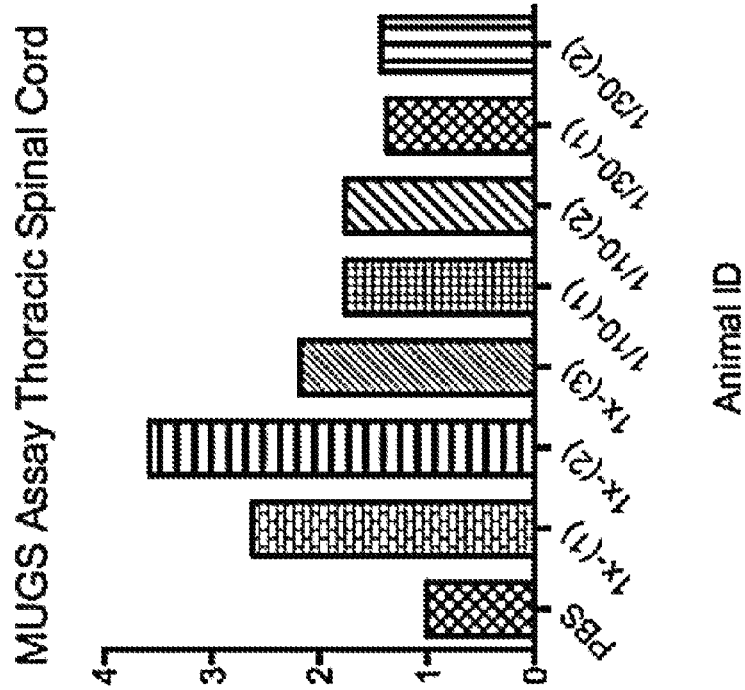
Figure 23D:
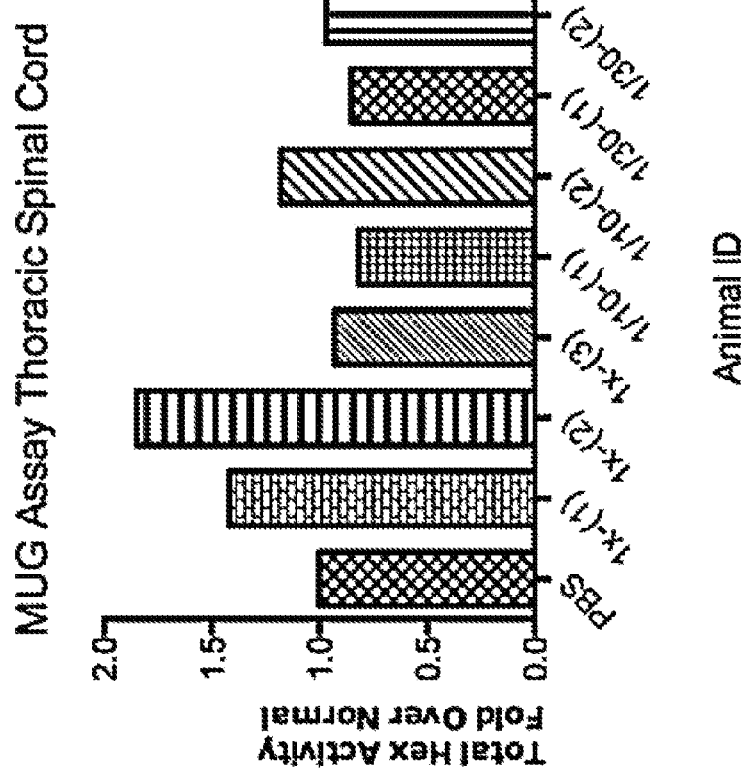

Two additional cohorts of NHP (N=2 per cohort) were injected with AAVrh8 vector formulation at total doses 1/10th and 1/30th the original dose, respectively, 2E11 and 1.1E11 vg. Neurological symptoms developed in 3 out of 4 NHPs injected with the lower doses of AAVrh8 vector formulation expressing cmHexA subunits, but onset was progressively delayed with decreasing doses. Despite a delay in onset of symptoms (or absence of obvious symptoms in one NHP), neuropathological assessment of the brain revealed extensive areas of necrosis, neuronal loss and vascular cuffing in all 4 NHPs in the lower dose cohorts (FIG. 22E). Hexosaminidase activity in brain was also elevated in these NHPs compared to that in saline-injected animals (FIG. 23). Increased Hex expression was also found in the spinal cord, which was more pronounced in the 1× dose animals (FIG. 23, bottom row).

As a control for potential toxicity associated with AAVrh8 capsids and/or preparation method, another cohort of NHPs (N=2) received 3.2E12 vg of a transgene-empty AAVrh8 vector, and both animals displayed normal behavior throughout the study (>90 days post-injection). Behavioral observations for all animals in the study are summarized in Table 3.

Figure 24:
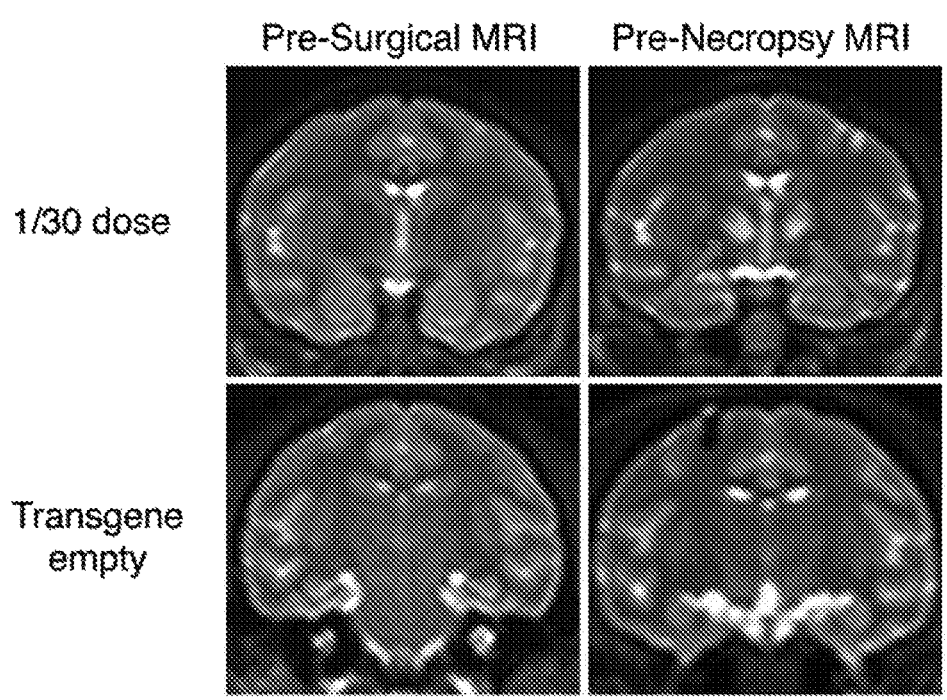
FIG. 24 is a pre-necropsy brain MRI revealing edema in the thalamus. Edema (arrows) in the thalami of an NHP injected with formulation of AAVrh8 vectors encoding cmHex-alpha and cmHex-beta at the $1/30^{th}$ dose prior to necropsy. No changes were observed in NHP injected with transgene-empty AAVrh8 vector.

Prior to necropsy, brain MRIs were performed for some NHPs in the lower dose cohorts and bilateral signal alterations were found in the thalamus, presumably due to edema (top row, FIG. 24), but no changes in NHPs injected with transgene-empty AAVrh8 vector were observed (bottom row, FIG. 24).

Figures 25A, 25B:
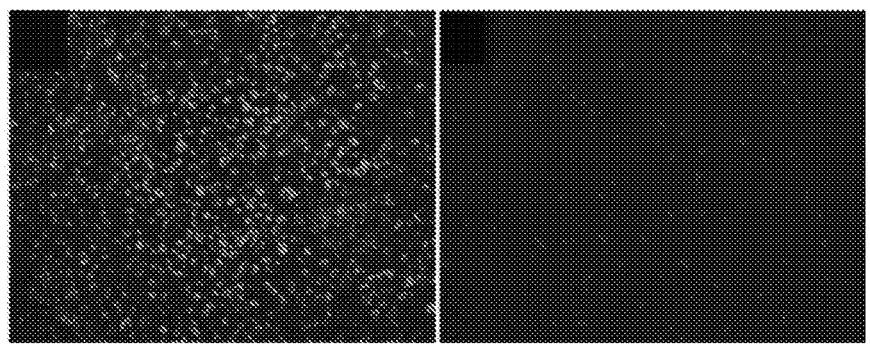
FIGS. 25A-25G show the protein expression in a monkey thalamus. Hex-β staining (green) (FIG. 25A) proximal and (FIG. 25B) distal to the injection site in the thalamus of a 1× dose animal is shown. Hex-α staining (green) (FIG. 25C) proximal and (FIG. 25D) distal to the injection site in the thalamus of 1/30 dose animal is shown. H&E staining (FIG. 25E) proximal and (FIG. 25F) distal to the injection site in the thalamus of 1/30 dose animal shown in FIGS. 25C-25D.
Figures 25C, 25D:
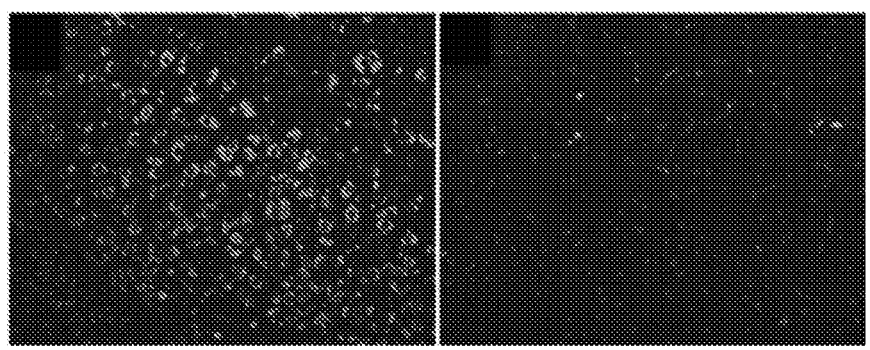
Figures 25E, 25F:
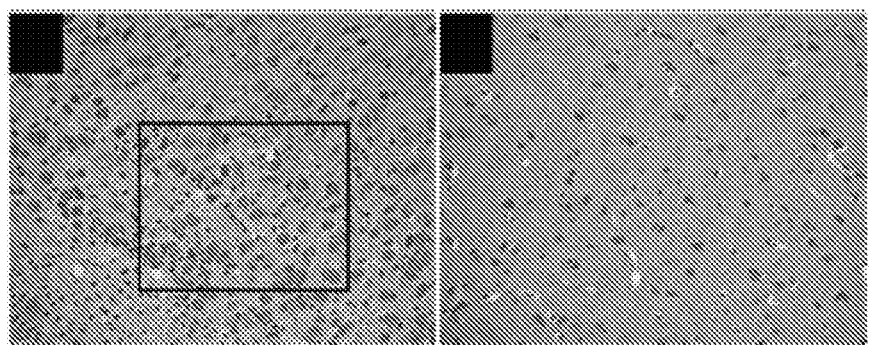
Figure 25G:
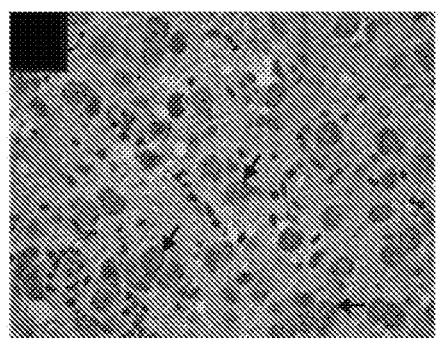

In addition to the neuronal loss in the thalamus along the injection tracks, large fields of neurons loaded with intracellular eosinophilic granules were observed in close proximity (FIGS. 25E, 25G), which was not apparent in other areas of the brain (FIG. 25F). Immunofluorescence staining with antibodies specific to hexosaminidase alpha- or beta-subunits revealed that these granules are likely to contain these two proteins (FIGS. 25A, 25C). These cells loaded with HexA subunit-positive granules were only observed in the thalamus (FIGS. 25B, 25D), which correlates with the findings in H&E stained sections. These observations are reminiscent of the findings in a GUSB transgenic mouse model where protein lysosomal storage was apparent in several tissues (Vogler et al., 2003).

There are two key observations from this safety study in normal juvenile NHPs: first, that thalamic regions containing large numbers of HexA-positive neurons appear intact with no evidence of significant inflammatory infiltrates (FIGS. 25E and 25G), despite massive neuronal loss and inflammation along the injection track (FIG. 22), and second, that there is no evidence of toxicity associated with the transgene-empty AAVrh8 vector at the highest dose. Consequently, it is thought that neurotoxicity in NHP brain after AAVrh8-HexA-mediated gene transfer is caused by a massive overexpression of HexA in AAVrh8-transduced thalamic neurons that triggers cell death beyond an unknown threshold and leads to a secondary neuro-inflammatory response (vascular cuffing, etc.).

TABLE 3

Summary of neurological symptoms observed in study animals

| AAV dose cmHexA & cmHexB | Survival days post Injection (90 = endpoint) | Clinical signs |
|---|---|---|
| 1x-(1) | 28 | lethargy, non-responsive |
| 1x-(2) | 23 | ataxia, unable to perch |
| 1x-(3) | 20 | generalized weakness especially of right leg, anorexia |
| 1/10-(1) | 91 | dyskinesias, chorea |
| 1/10-(2) | 57 | dyskinesias, chorea, "star gazing" |
| 1/30-(1) | >90 | none |
| 1/30-(2) | 66 | Loss of voluntary use of right arm, eventual lethargy |
| PBS | 90 | none |
| Transgene empty-(1) | >90 | none |
| Transgene empty-(2) | >90 | none |

Example 8

Figure 26A:
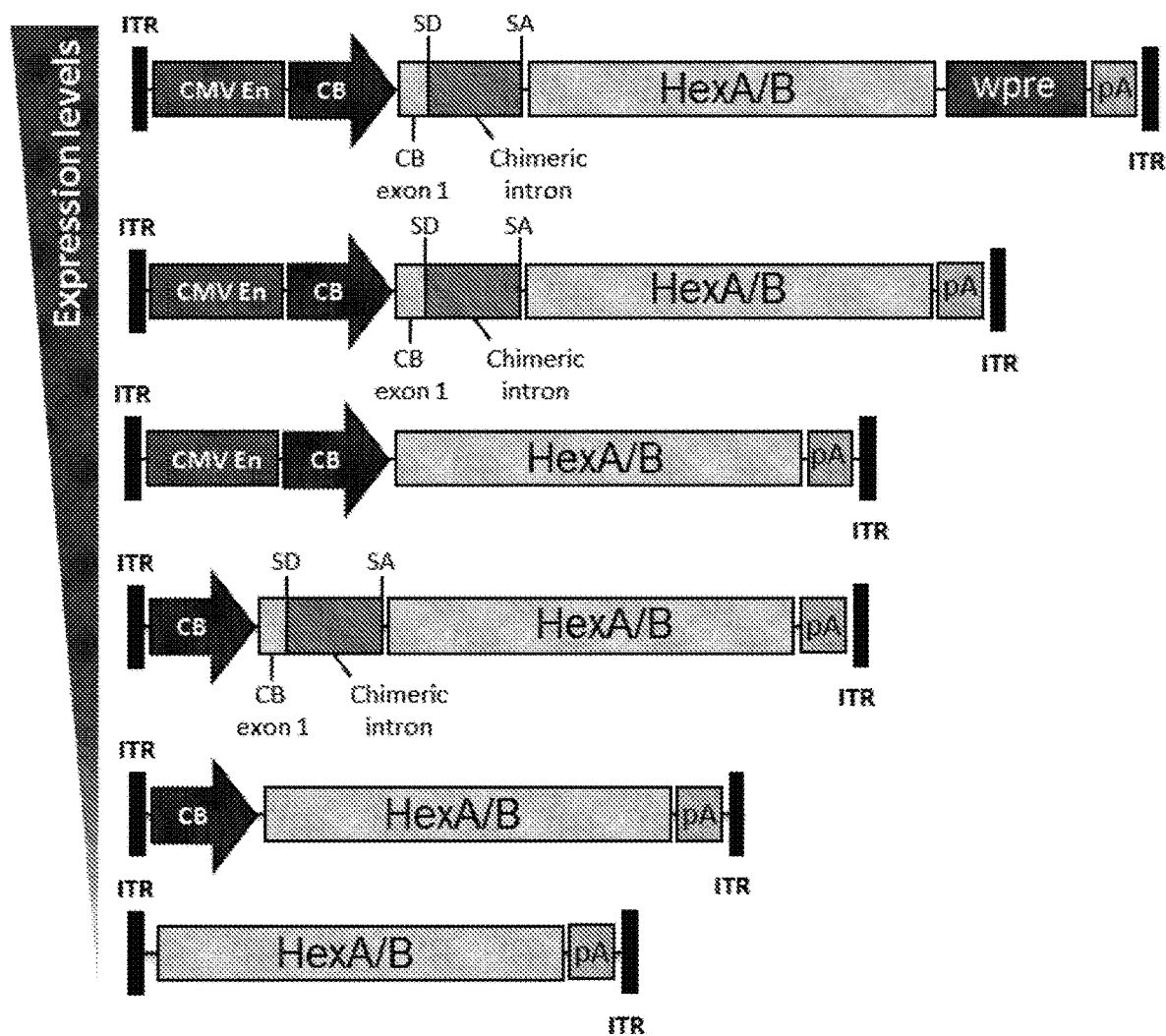
Figure 26B:
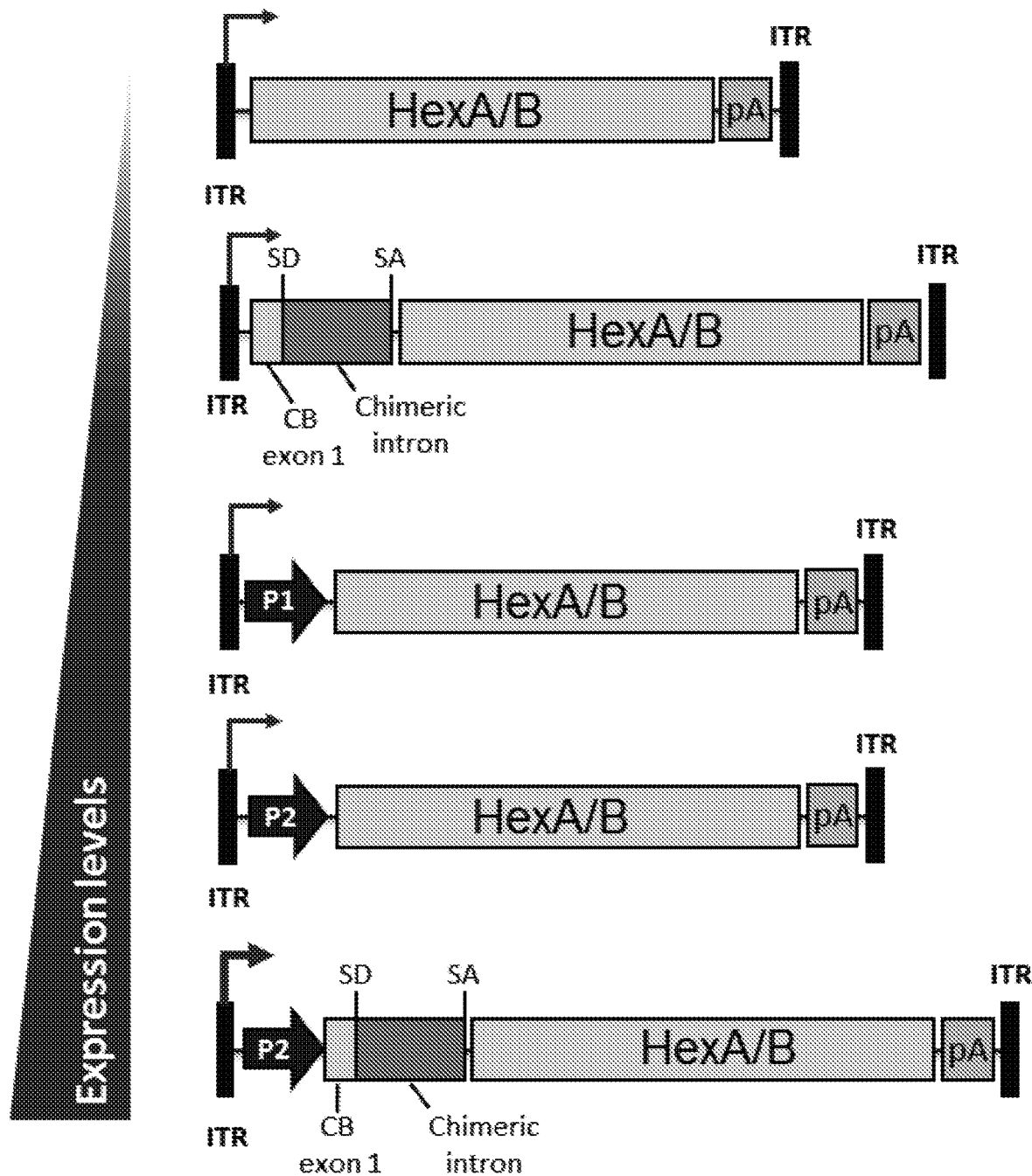
FIG. 26B shows ITR-expression based vectors that progressively incorporate more elements known to increase ITR-driven gene expression. Abbreviations: CMV Enh—cytomegalovirus immediate-early enhancer; CB—chicken beta-actin promoter; HexA/B—for each vector design a pair of vectors will be generated carrying cynomolgus macaque HexA and HexB cDNAs; pA—polyadenylation signal; ITR—AAV2 inverted terminal repeat; P1—Promoter 1 thought to increase ITR-mediated gene expression by ~10-fold; P2—promoter thought to increase ITR-mediated gene expression by ~50-fold.
Figure 27:
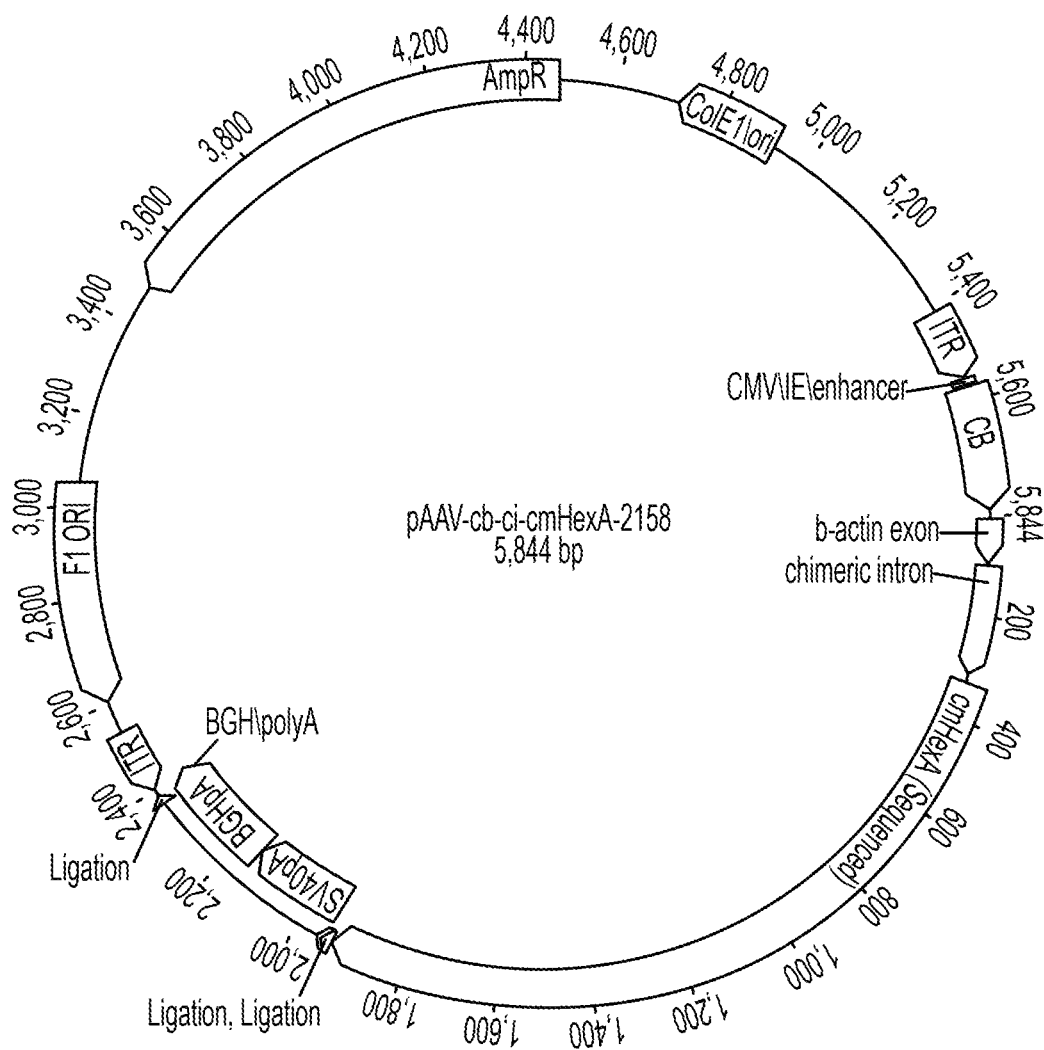
FIG. 27 shows a vector map of pAAV-cb-ci-cmHexA-2158.
Figure 28:
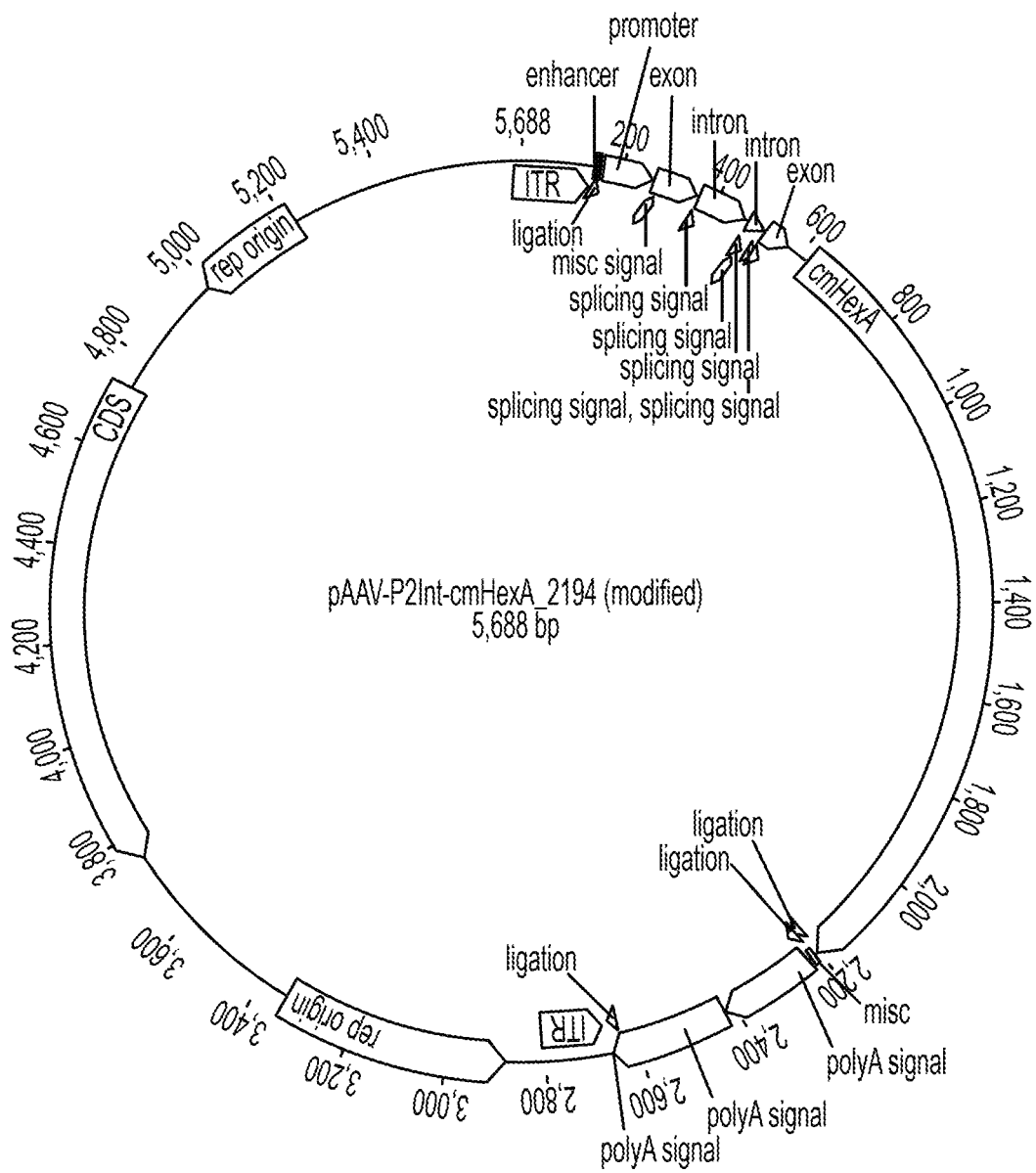
FIG. 28 shows a vector map of pAAV-P2Int-cmHexA_2194 (modified).

New AAV vector plasmids (FIG. 26) were tested for the level of hexosaminidase (Hex) enzyme expression upon transient transfection of 293T cells. Two examples are shown in FIGS. 27 and 28.

Figure 29A:
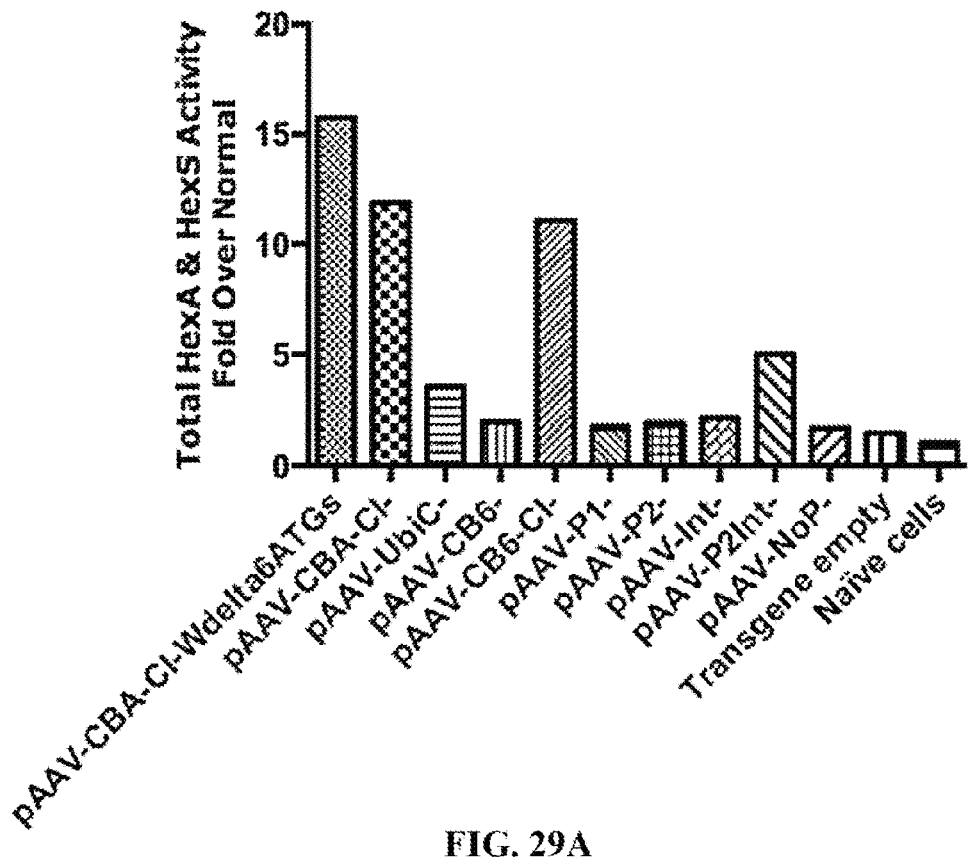
FIGS. 29A-29B show a gradient of hexosaminidase activity in transiently transfected 293T cells. Hexosaminidase activity was measured in cell lysates at 72 hrs post-transfection using the artificial substrates 4MUG (FIG. 29A) and 4MUGS (FIG. 29B), respectively cleaved by all beta-hexosaminidase isoforms (HexA, B and S), or alpha-subunit containing isoforms only (HexA, HexS).
Figure 29B:
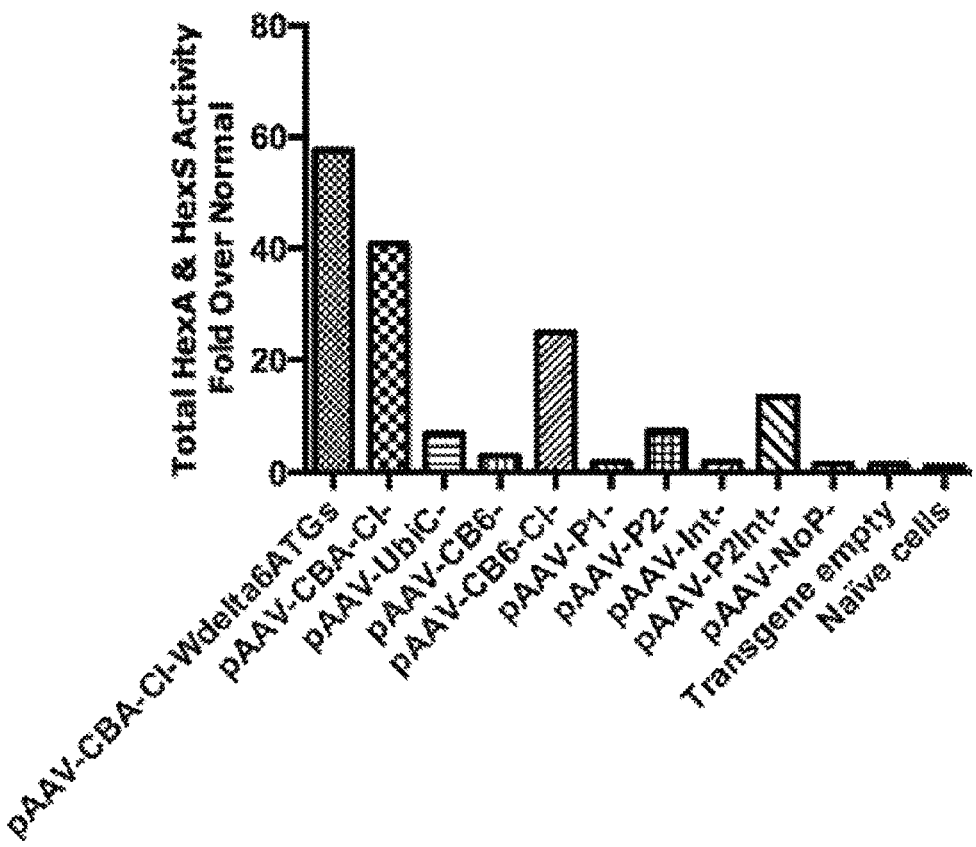

The original AAV vector plasmid pair (pAAV-CBA-CI-Wdelta6ATGs) generated the highest levels of Hex activity, and the AAV vector plasmids without a promoter (pAAV-NoP) or transgene (transgene empty) did not yield any detectable increase in Hex activity over naïve non-transfected 293T cells (FIG. 29). The other AAV vector plasmid pairs generated a gradient of Hex activities. Six experimental AAV vector pairs were chosen for further testing in nude mice along with two AAV vector controls (no promoter and no transgene). A total of 15 vector stocks were produced for in vivo testing (Table 4).

Figure 30:
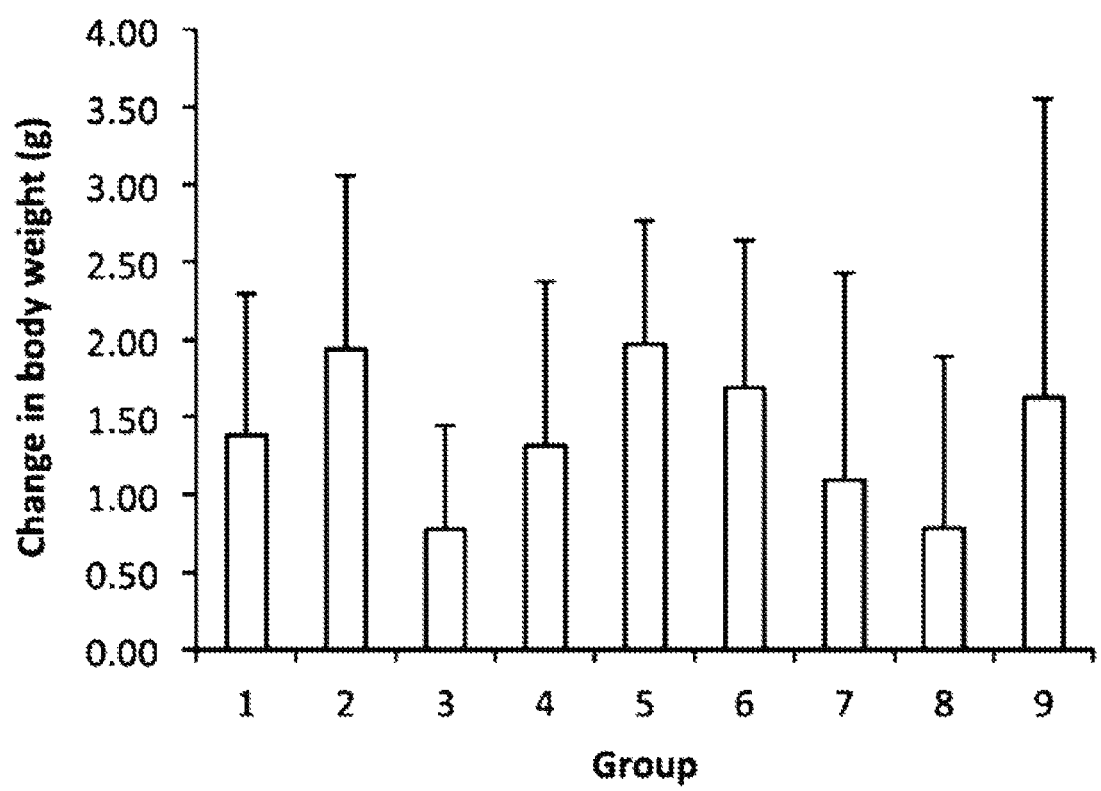
FIG. 30 shows the change in body weight over 1 month study period. Error bars represent 1 standard deviation.
Figures 33K, 33L, 33M, 33N, 33O, 33P, 33Q, 33R, 33S, 33T:
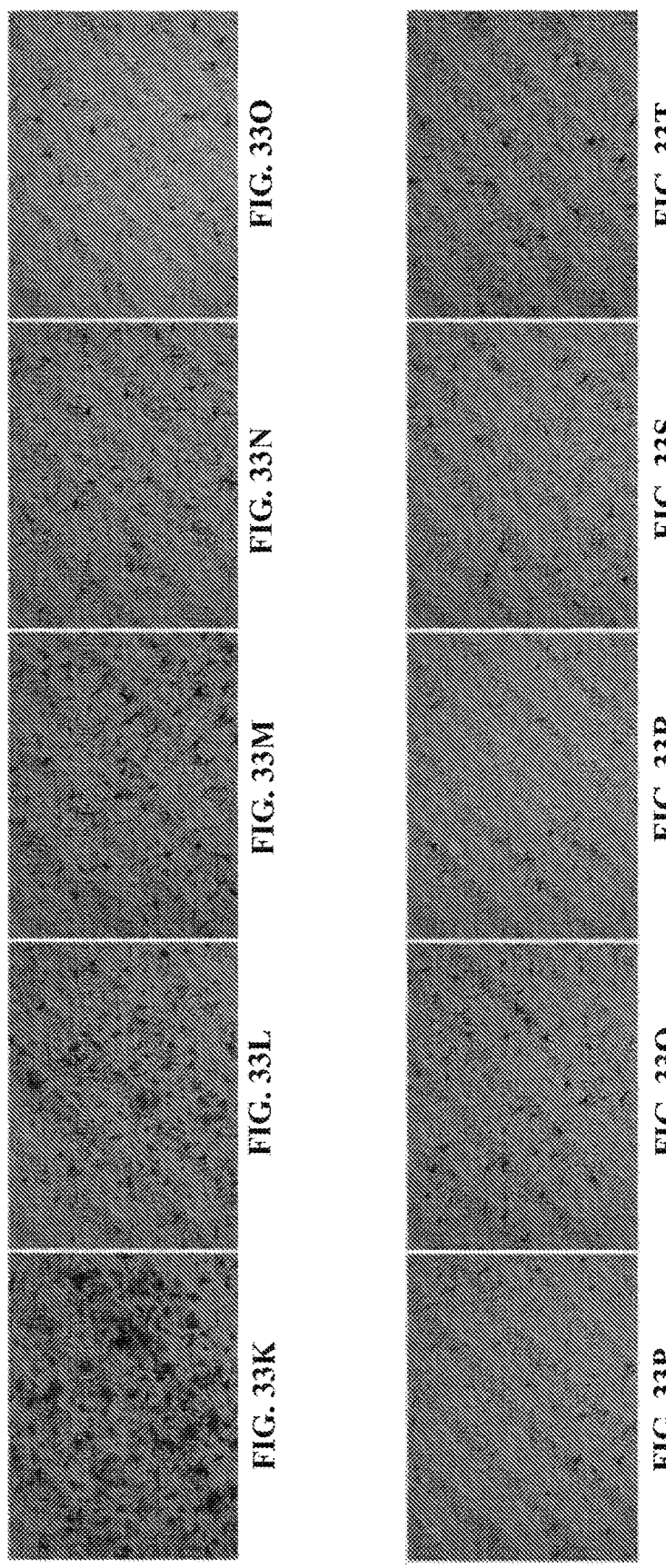

AAV vectors were injected bilaterally into the thalamus and left cerebral lateral ventricle of 10-12 week-old male athymic nude mice (Charles River Labs) at a total dose of $1.32 \times 10^{10}$ vector genomes (vg). Control groups included mice injected with the AAV vector formulation without a promoter (AAV-NoP), an AAV vector without transgene (transgene empty), phosphate buffered saline (PBS), and finally non-injected mice (N=8 for all experimental and control groups) (Table 4). Mice were killed at 1 month post-injection for biochemical analysis of Hex expression and histological studies. All groups displayed identical increase in average body weight over the course of the experiment (FIG. 30), and there was no evidence of gross behavioral changes during this period, unlike in preliminary experiments with higher AAV vector dose where animals were euthanized because of significant body weight loss and in onset of neurological symptoms. The dose used in the current experiment ($1.32 \times 10^{10}$ vg) was determined by lowest titer of one of the vector pairs in order to normalize the total vector dose for all test articles and controls.

Figure 36:
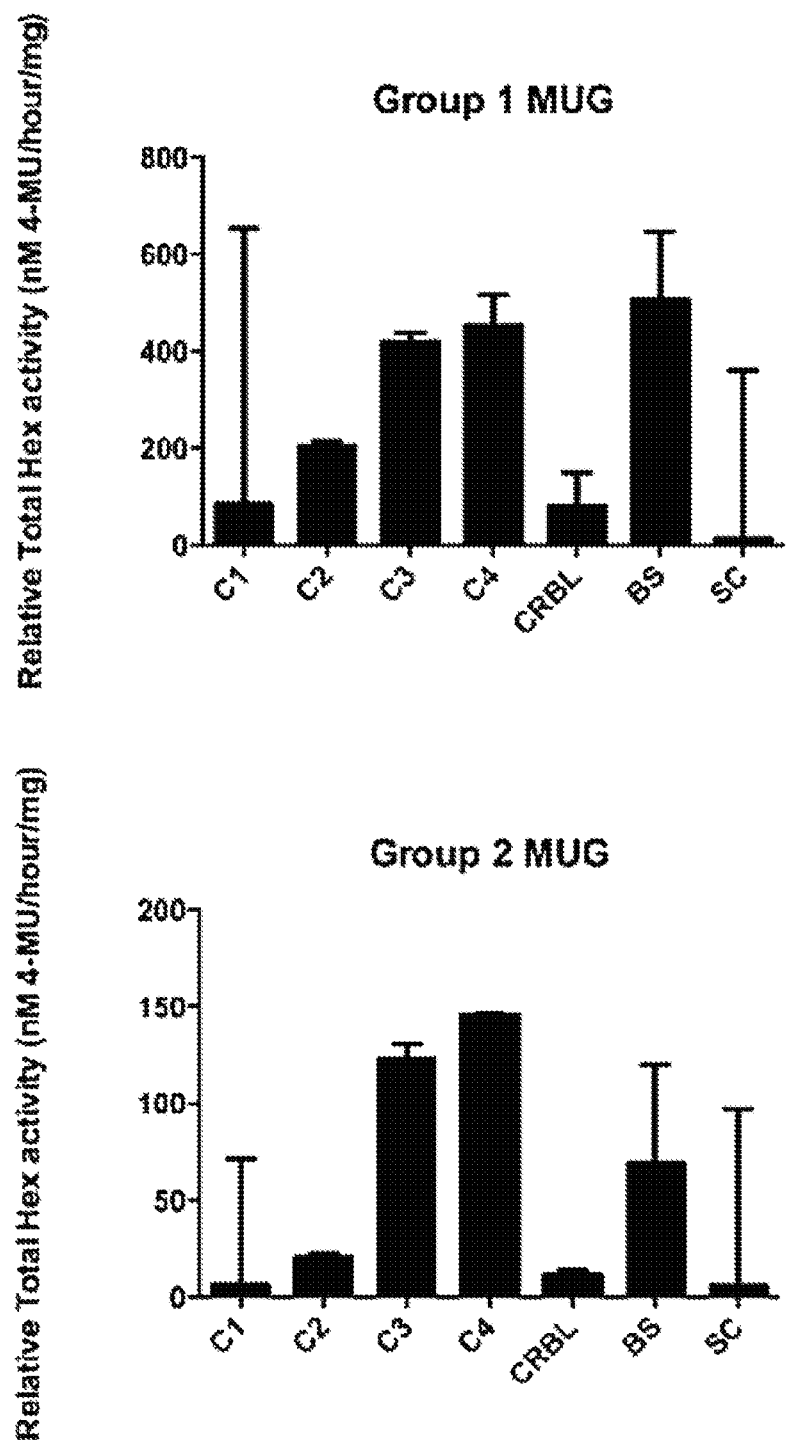
FIG. 36 shows the relative total Hex activity in athymic nude mice injected intracranially with AAV vectors encoding cynomolgus Hexa and Hexβ. The in vitro enzymatic activity of HexB, HexA, and HexS measured by MUG substrate, normalized to naïve (C1: olfactory bulbs and first 3 mm coronal slice of cerebrum, C2: following 2 mm coronal slice of cerebrum, C3: following 3 mm coronal slice of cerebrum which contain injection sites, C4: following 2 mm coronal slice of cerebrum, CRBL: cerebellum, BS: brain stem, SC: spinal cord) is shown.
Figure 36:
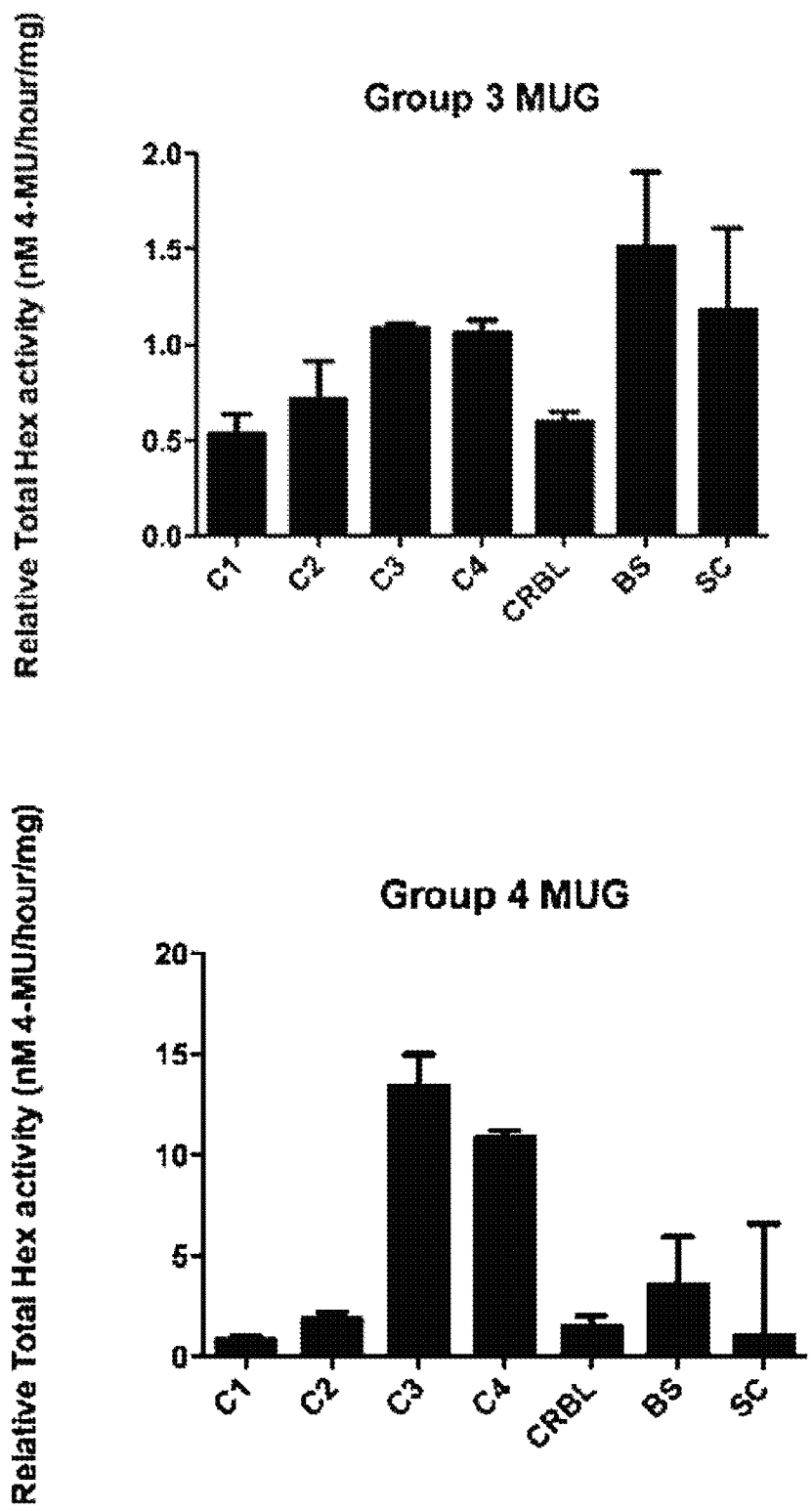
Figure 36:
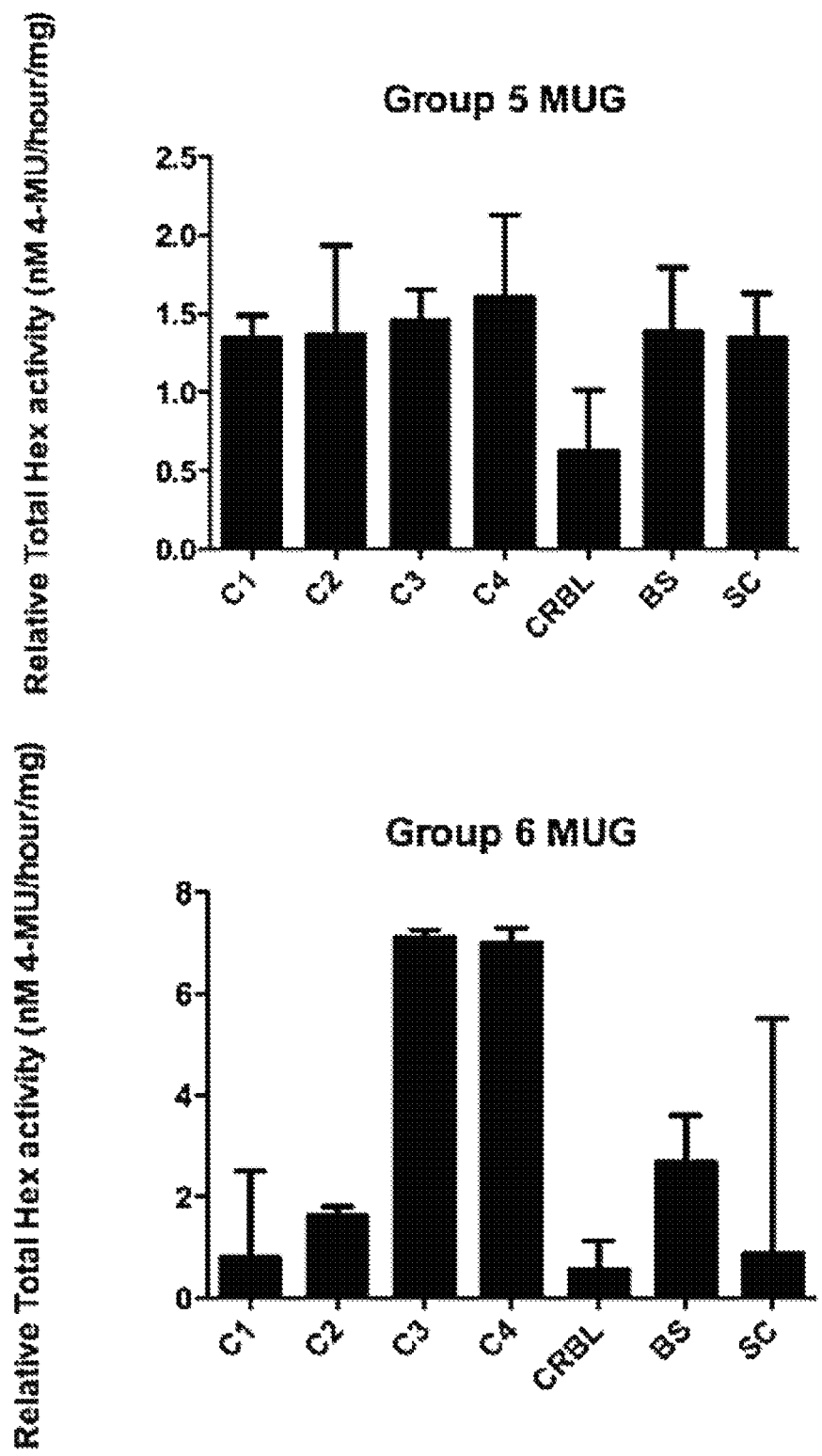
Figure 36:
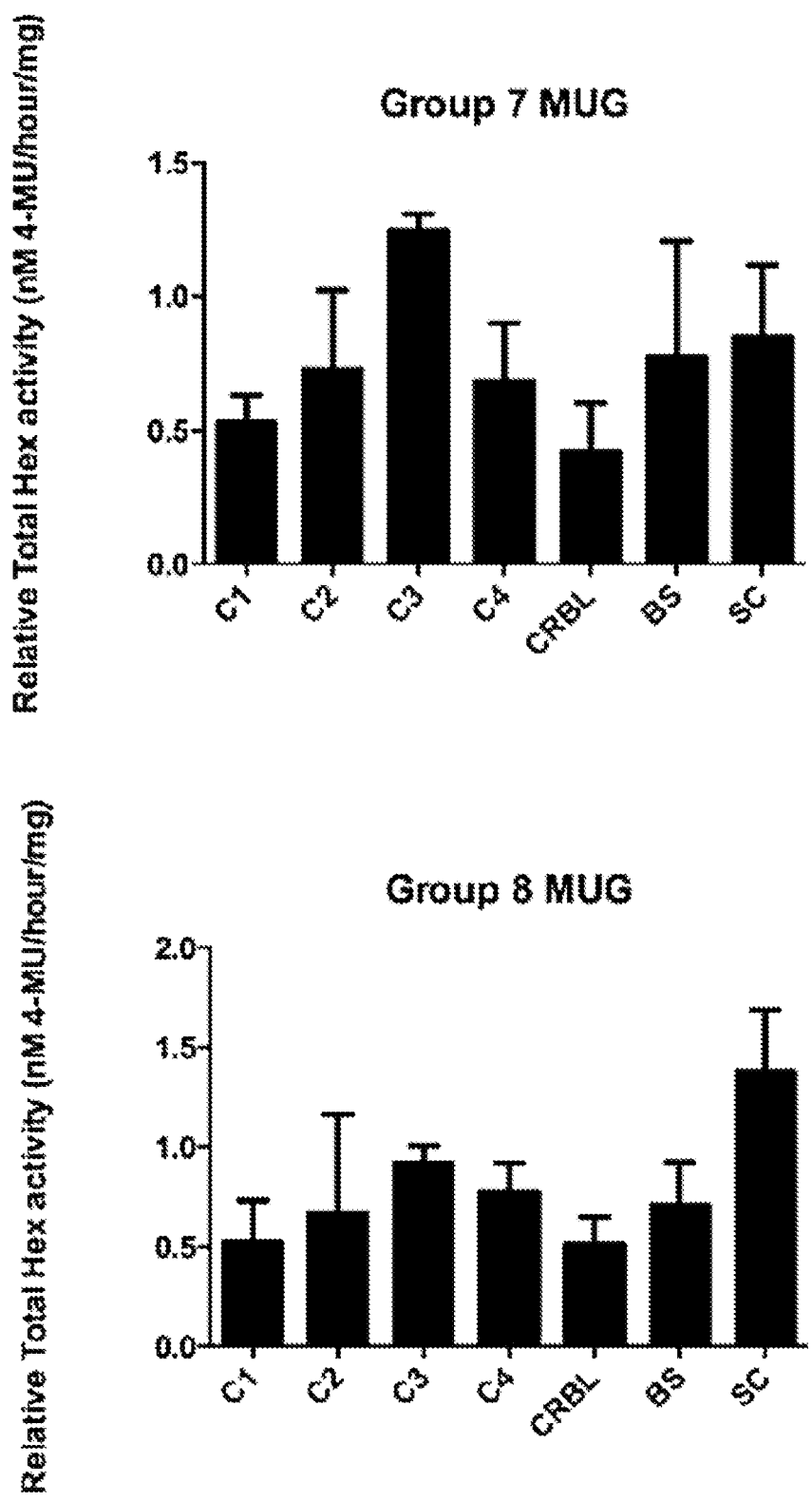
Figure 36:
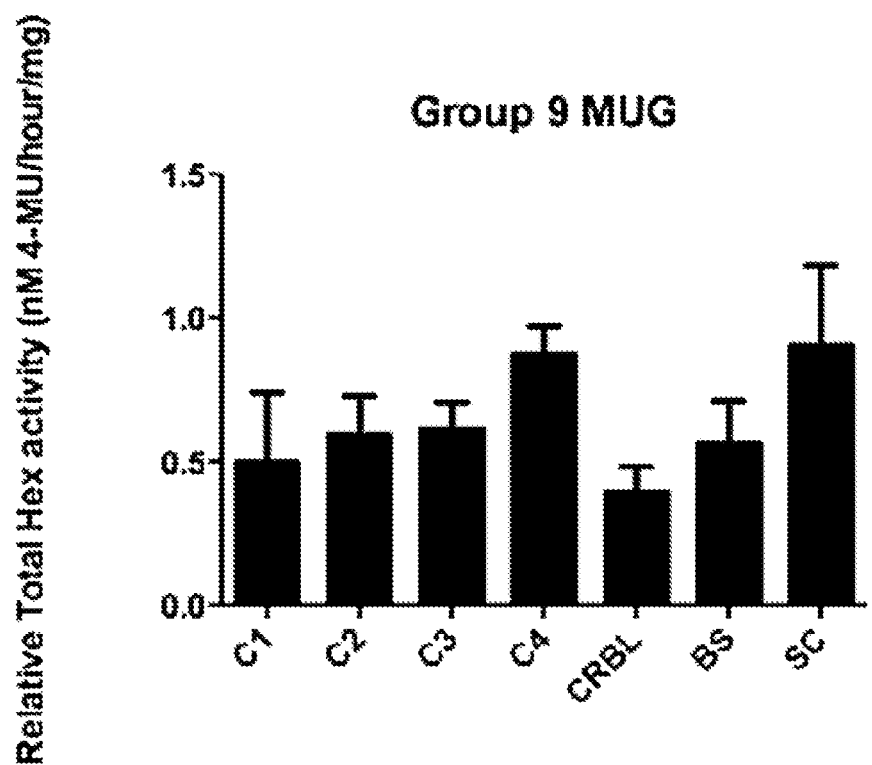
Figure 37:
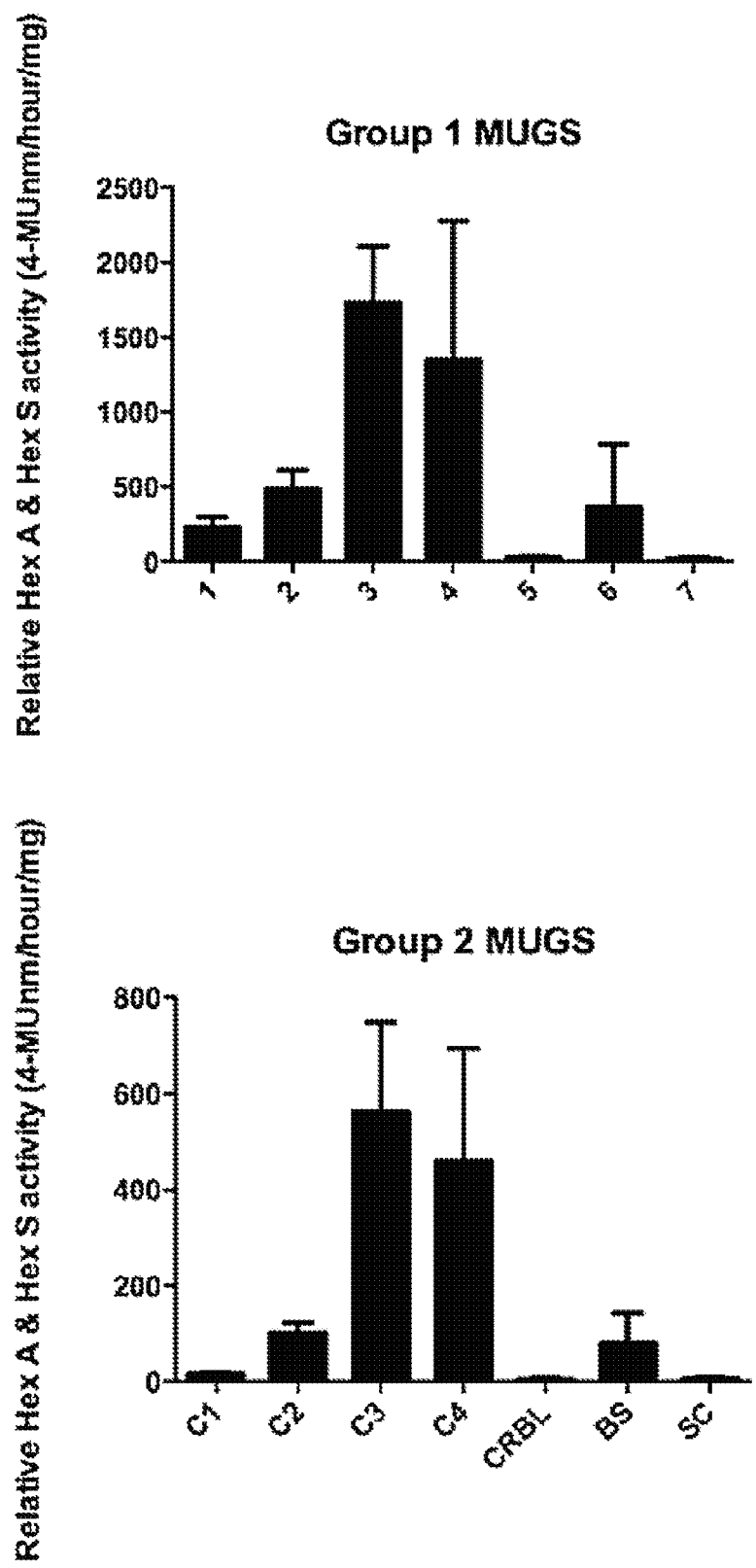
FIG. 37 shows the relative HexA and HexS activity in athymic nude mice injected intracranially with AAV vectors encoding cynomolgus Hexa and Hexβ. The in vitro enzymatic activity of HexA and HexS measured by MUGS substrate, normalized to naïve (C1: olfactory bulbs and first 3 mm coronal slice of cerebrum, C2: following 2 mm coronal slice of cerebrum, C3: following 3 mm coronal slice of cerebrum which contain injection sites, C4: following 2 mm coronal slice of cerebrum, CRBL: cerebellum, BS: brain stem, SC: spinal cord) is shown.
Figure 37:
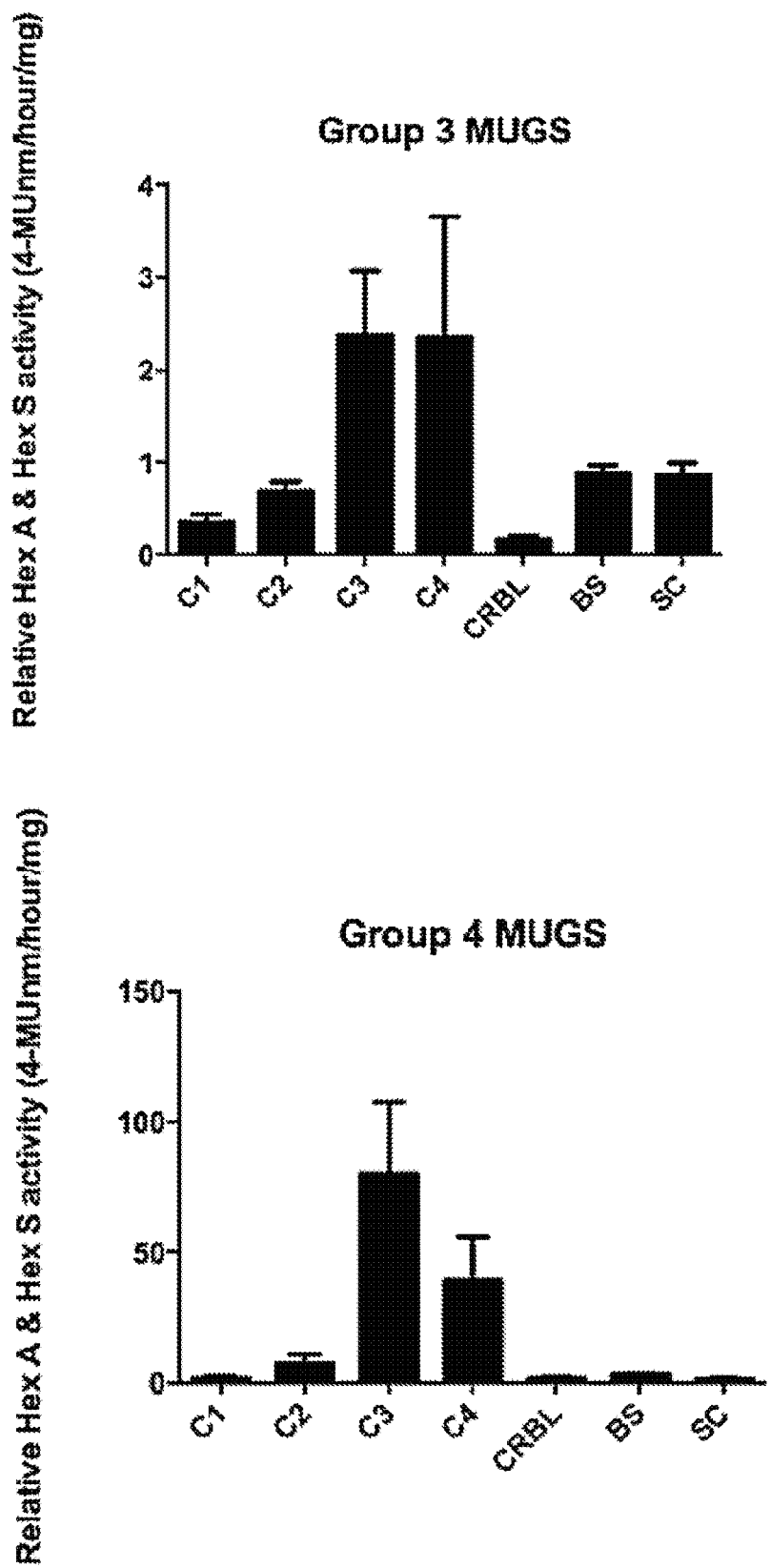
Figure 37:
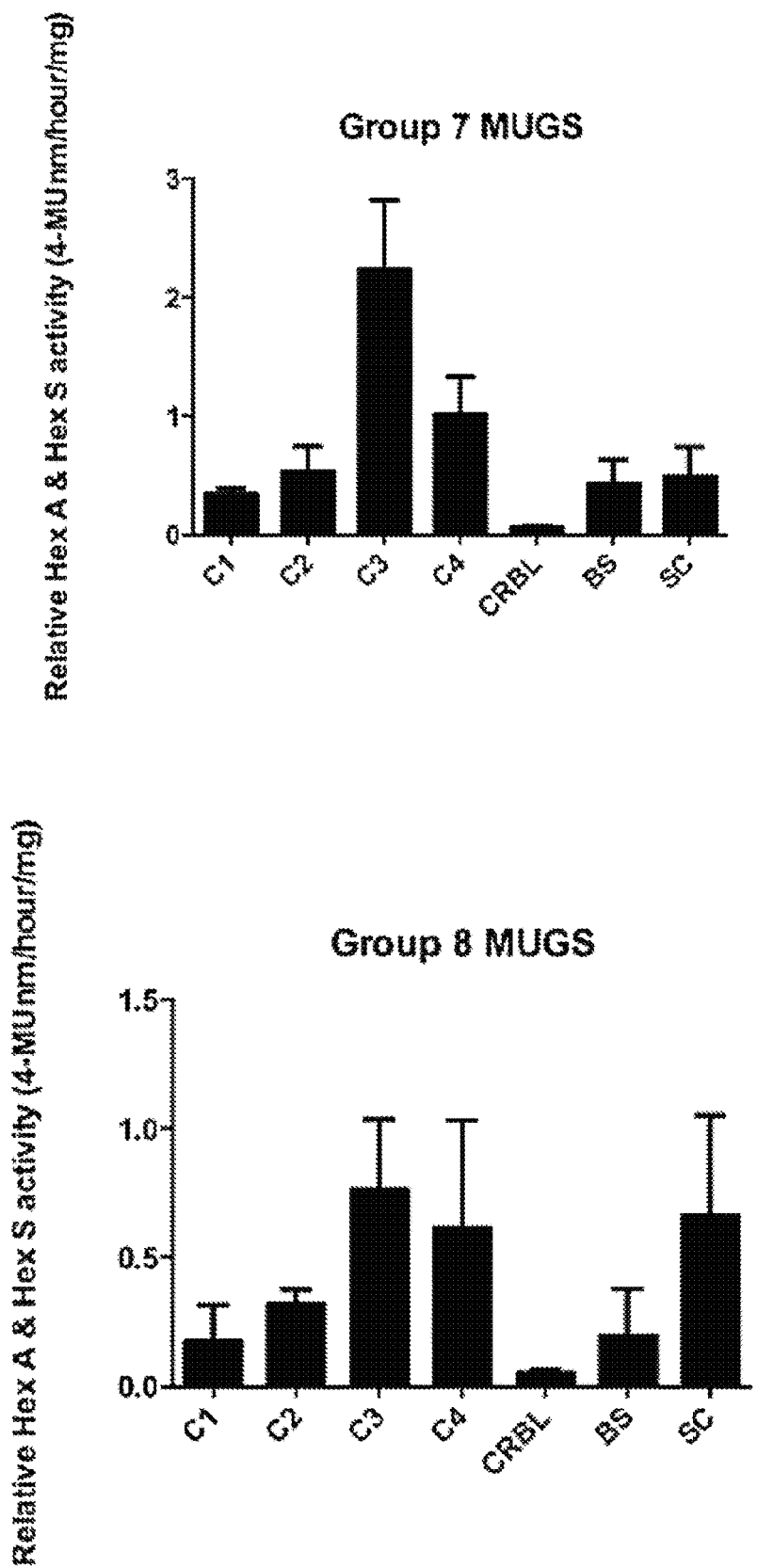
Figure 37:
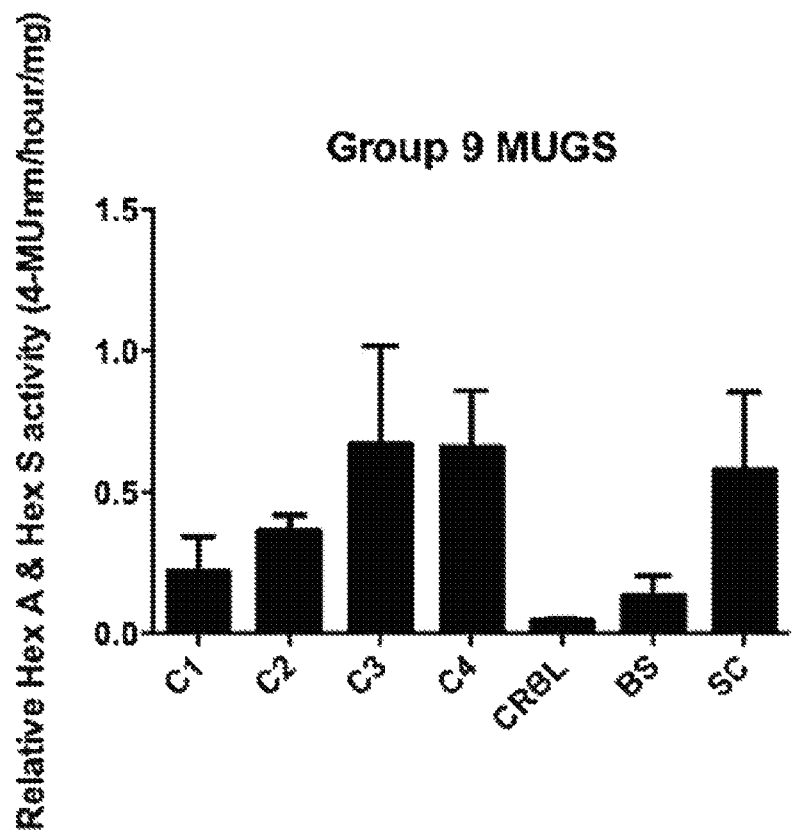

Hex activity was measured in 4 coronal brain blocks, cerebellum, brainstem and spinal cord using the artificial substrates MUG (FIG. 36) and MUGS (FIG. 37). Hex activity in the coronal brain block containing the injection site is shown in Table 4 to summarize the findings. The original AAV vector pair (Group 1) generated Hex activities 400-1,700 fold above normal. Similar to the results in cell culture other AAV vector pairs generated Hex activities in the brain 3-fold (Group 2), 20-30-fold (Group 4), and 50-100-fold (Group 6) lower than the original AAV vector formulation (Group 1), providing with the anticipated range of 1-2 log of activities in AAV-mediated Hex expression in brain. Other AAV vectors pairs (Groups 3 and 5) did not generate Hex activity above normal levels present in athymic nude mouse brain. The control groups (Groups 7, 8, and 9) did not show significant changes in Hex activity.

Neuropathological examination of the brains revealed numerous thalamic neurons containing eosinophilic granules in Group 1 animals (FIG. 31K). This finding is identical to observations in monkeys injected with these AAV vectors used in Group 1, but the number of these abnormal neurons appears considerably lower in mice than monkeys. This observation was also made in Group 2 animals, but the number of abnormal neurons was considerably lower than in Group 1 (FIG. 31L). The same neurons were observed in the hippocampus of Group 2 animals (FIG. 31B). There was no evidence of such neurons in any other group of animals. Immunofluorescence staining with an antibody to alpha-subunit of HexA revealed numerous cells expressing the enzyme in the hippocampus and thalamus of animals in Groups 1 (FIGS. 31A, 31K), 2 (FIGS. 31B, 31L), 4 (FIGS. 31D, 31N), and 6 (FIGS. 31F, 31P). There was no evidence of Hex-alpha subunit expression in control groups, possibly because the species specificity of the antibody used in this study which detects human and cynomolgus macaque enzyme, but not the mouse protein.

A dramatic increase in Iba-1 staining (microglia activation) was observed in the hippocampus and thalamus in animals injected with the original AAV vector formulation (group 1) (FIGS. 33A, 33K) compared to controls (FIGS. 33I, 33J, 33S, 33T). This evidence for microglia activation was localized to the sites where HexA-positive cells were detected by immunofluorescence staining (FIGS. 32A, 32K), with no apparent changes in microglia elsewhere in the brain. The increase in Iba-1 staining in hippocampus and thalamus was considerably milder in groups 2 and 3 (FIGS. 33B-33C, 33L-33M), and essentially indistinguishable from controls in groups 4-7 (FIGS. 33D-33G; 33N-33Q).

The brain was also analyzed for evidence of reactive astrogliosis using GFAP immunostaining (FIG. 34). In the hippocampus, evidence of reactive astrogliosis was only found in animals injected with the original AAV vector formulation (group 1) (FIG. 34A). All others were indistinguishable from controls. In the thalamus, there appeared to be some degree of astrogliosis in groups 1-3 (FIGS. 34K-34M), and mild or indistinguishable levels from the controls in groups 4-7 (FIGS. 34N-Q). There was no evidence of astrogliosis in other areas of the brain in any of the groups.

Figure 35:
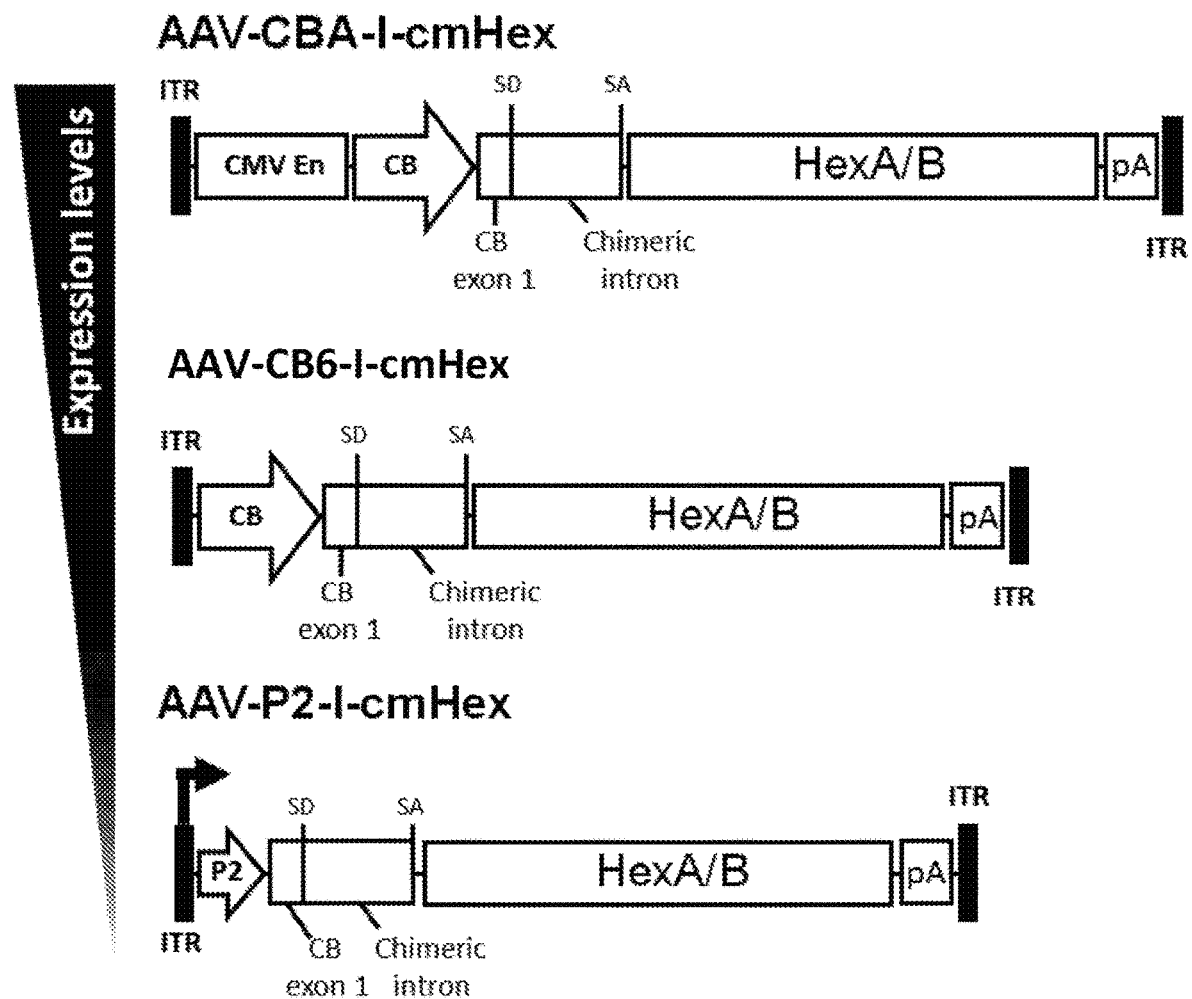
FIG. 35 shows new AAV vectors selected for further testing in non-human primates.

Two new AAV vectors (FIG. 35), AAV-CB6-I-cmHex (promoter represented by SEQ ID NO: 4) and AAVP2-I-cmHex (promoter represented by SEQ ID NO: 5, construct represented by SEQ ID NO: 6), met all presently testable criteria defined prior to the initiation of the experiments (absence of gross behavioral alterations, rotarod performance comparable to control groups, constant or increasing body weight between 0 and 30 days post-injection, absence of neuropathology, and enzyme expression above normal in thalamic block and rostral non-injected block). These new AAV vector formulations (groups 4 and 6) yielded increased Hex expression in the brain with little or no evidence of neuropathological changes (absence of eosinophilic neurons, microgliosis or astrogliosis) compared to controls.

The new AAV-CBA-I-cmHex vector (FIG. 35) where the wpre element was removed from the original AAV vector, but the expression elements (promoter and artificial intron) remain the same was also tested. This AAV vector (group 2) showed ~3-fold lower Hex activity levels compared to the original AAV vector and decreased microgliosis compared to the original AAV vector. Considering that the expression elements are the same as in the AAV vectors used in long-term experiments in Sandhoff mice and cats, it is thought that the AAV vector may also mediate long-term expression. Given the reduction in Hex expression level and milder activation of microglia, this new AAV vector is unlikely to significantly impact the behavior of NHPs at the dose (3E11 vg) and duration of the experiment in Example 9.

TABLE 4

Experimental groups and Hex activity (MUG and MUGS) in injection block

| Group | Vector | Relative Enzyme Activity | |
|---|---|---|---|
| | | MUG | MUGS |
| 1 | pAAV-CBA-CI-cmHexA-WPRE Δ6ATGs<br>pAAV-CBA-CI-cmHexB-WPRE Δ6ATGs | 419.07 | 1732.31 |
| 2 | pAAV-CBA-CI-cmHexA<br>pAAV-CBA-CI-cmHexB | 122.96 | 563.12 |
| 3 | pAAV-CB6-cmHexA<br>pAAV-CB6-cmHexB | 1.08 | 2.38 |
| 4 | pAAV-CB6-CI-cmHexA<br>pAAV-CB6-CI-cmHexB | 13.43 | 79.97 |
| 5 | pAAV-P2-cmHexA<br>pAAV-P2-cmHexB | 1.46 | 1.29 |
| 6 | pAAV-P2-CI-cmHexA<br>pAAV-P2-CI-cmHexB | 7.10 | 16.51 |
| 7 | pAAV-cmHexA<br>pAAV-cmHexB | 1.25 | 2.24 |
| 8 | pAAV-CBA-CI-WPRE Δ6ATGs | 0.92 | 0.76 |
| 9 | PBS | 0.61 | 0.67 |
| 10 | Naïve | 1.00 | 1.00 |

Note:
Relative enzyme activity refers to fold elevation in Hex activity above normal in the brain of athymic nude mice.

Example 9

Three AAV vector designs (FIGS. 19 and 35) were selected in athymic nude mice to increase beta-hexosaminidase expression in brain, and reduced inflammatory response (astrogliosis and microglia activation) compared to the original AAV vector formulation. AAVrh8 vectors were injected into NHPs (Table 5) screened for absence or very low titers of neutralizing antibodies to AAVrh8 capsid.

Figure 38A:
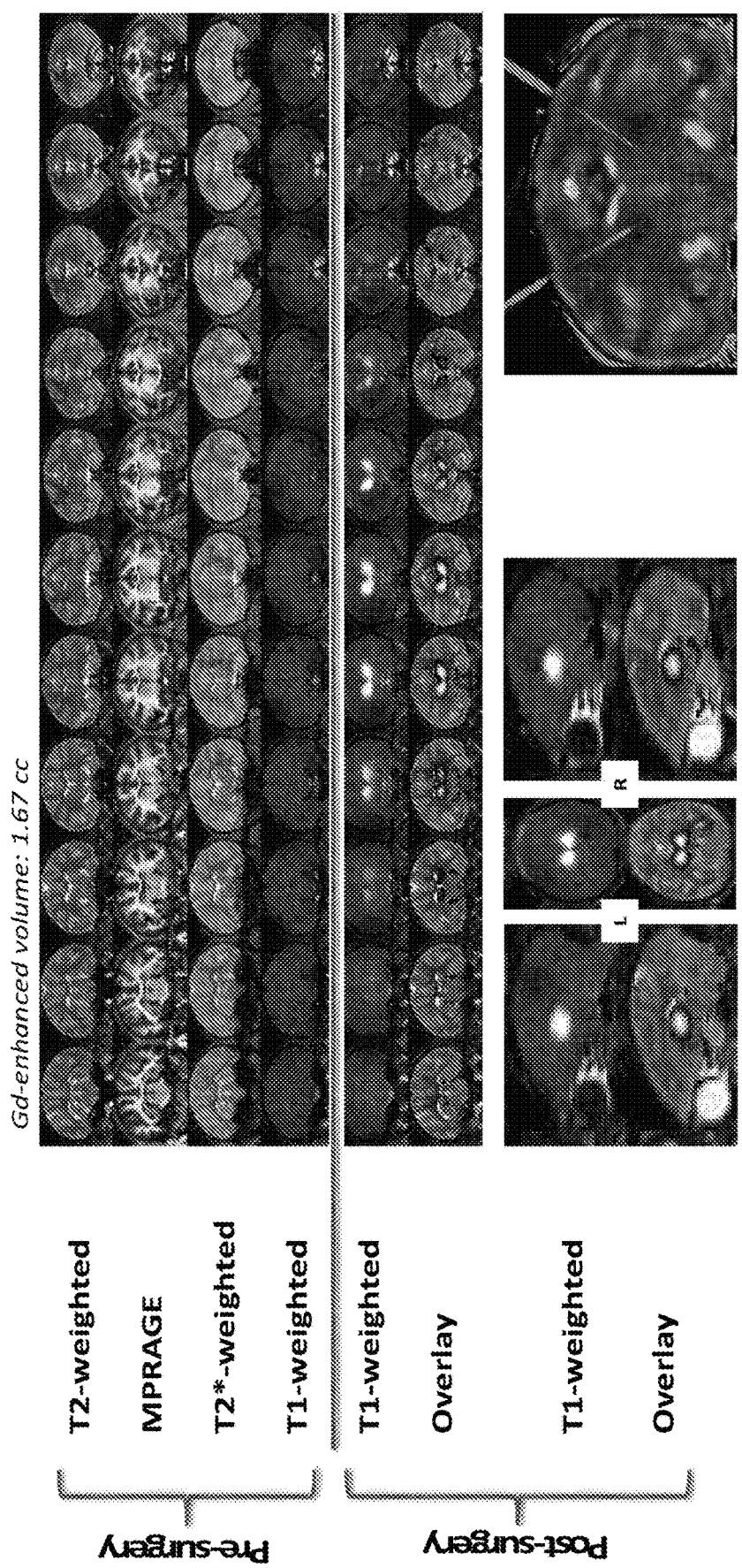
FIGS. 38A-38B show MRI analysis of targeting and distribution after intraparenchymal injections.
Figure 38B:
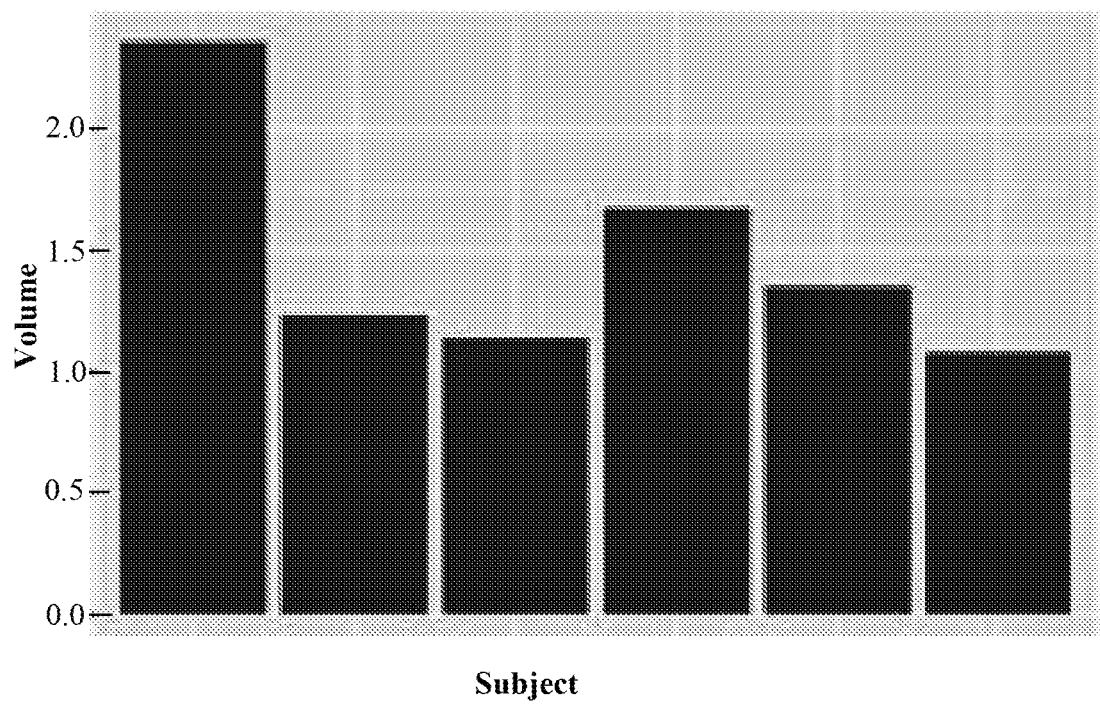

A total dose of $3.2 \times 10^{11}$ vg was infused bilaterally into the thalamus (50% dose, 2×150 μl) and left cerebral lateral ventricle (50% dose in 300 μl). The vector formulations also contained 2 mM gadolinium to determine targeting accuracy and distribution by brain MRI immediately following injection (FIG. 38A). All NHP tolerated the surgical procedure well with no complications. The average volume of gadolinium distribution (Vd) in the thalamus was 1.47±0.48 mL (FIG. 38B), which corresponds to a Vd/Vi ratio of 4.9, since the injected volume in the thalamus (Vi) was 0.3 mL.

Figure 39:
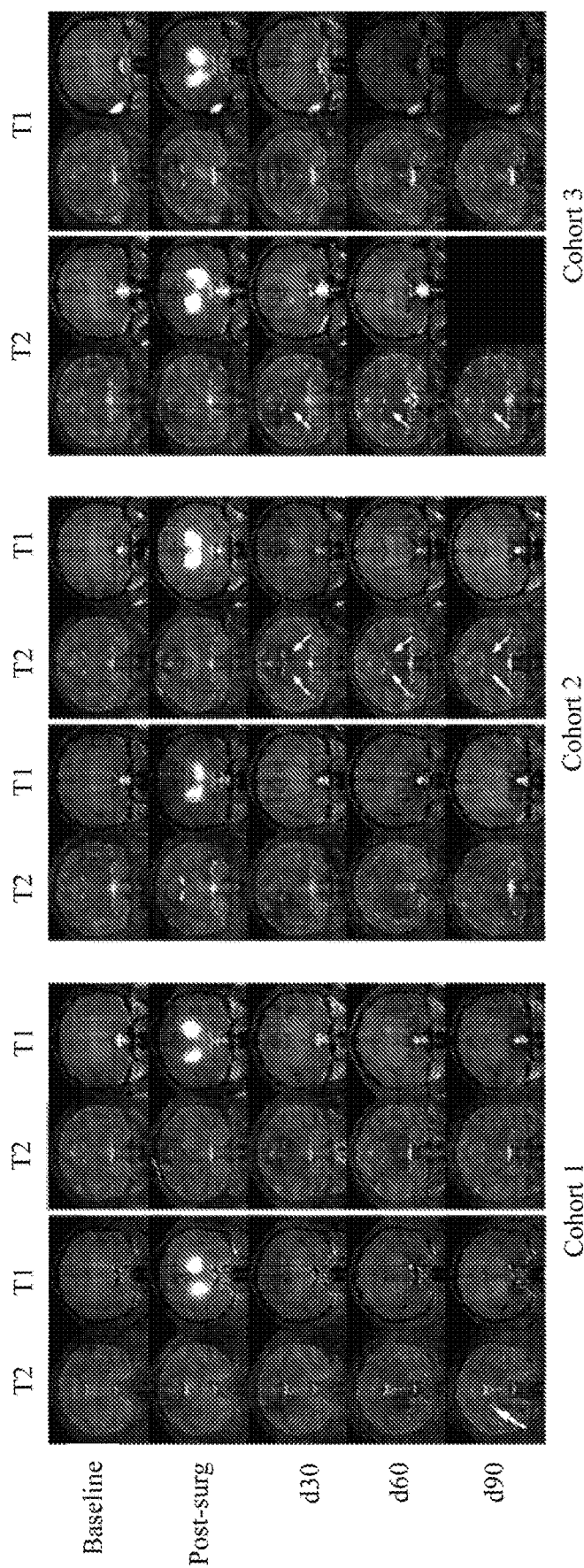
FIG. 39 shows the brain MRI of AAVrh8-injected NHPs throughout the course of the 90 day experiment. Arrows indicate regions of hyperintense signal in the thalamus in three NHPs.

The behavior of all six AAVrh8-injected NHPs remained normal throughout the 90-day study. As planned, brain MRI was carried out monthly (FIG. 39). Signal changes at the injection sites were documented in two monkeys from cohorts 2 and 3 from day 30 onward, but with no apparent change over time (FIGS. 40B, 40C). In one monkey in cohort 1 there was no signal changes in brain MRI at days 30 and 60 post-injection, but a large signal change was detected in the left thalamus at day 90 (FIG. 40A). Despite this abnormal signal at day 90 the overall behavior of this monkey remained unchanged throughout the study.

The brain was cut into 4 mm coronal blocks and used to map hexosaminidase (Hex) activity and assess neuropathology. Biopsy punches (3 mm diameter) were used to sample the brain to generate a map of enzyme distribution (FIG. 41). Total Hex activity (HexA, HexB, and HexS) above normal was detected only in punches of the thalamus in all cohorts (Table 6). In agreement with studies in athymic nude mice, the total Hex activity in thalamic punches was highest in cohort 1 (up to 87-fold above normal), and similar in cohorts 2 and 3 (up to 9-fold above normal). Total Hex activity in most other sampled brain regions were similar to that in non-injected control monkeys.

Figure 42:
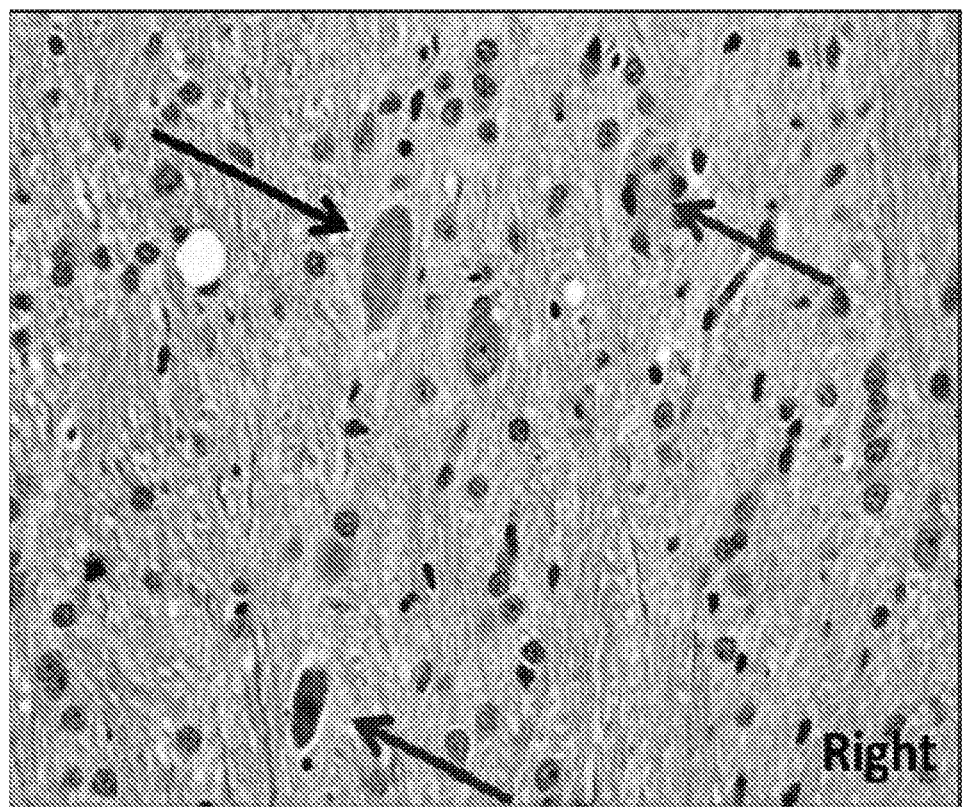
FIG. 42 shows the neuropathological findings in the brain of cohort 1 NHPs, including intraneuronal accumulation of eosinophilic granules, neurodegeneration, and neuronophagia.

Neuropathological evaluation of the brains revealed abundant accumulation of intraneuronal eosinophilic material in monkeys in cohort 1 (FIG. 42, black arrow). Moderate to severe neuronal degeneration was seen in cohort 1 animals. In the left thalamus of one monkey (ID 295851) in cohort 1 there was severe focal spongiosis and perivascular cuffing (FIGS. 43A, 43B). This lesion corresponded to the abnormal MRI signal that became evident in the left thalamus of one monkey in cohort 1 at 90 days post-injection (FIG. 40A).

In cohort 2, there was no accumulation of eosinophilic material, rare neuronal degeneration and satellitosis. Focal inflammation of white matter with neuronal degeneration most likely associated with injection site/track trauma was noted in one monkey (ID 295847).

Figure 45:
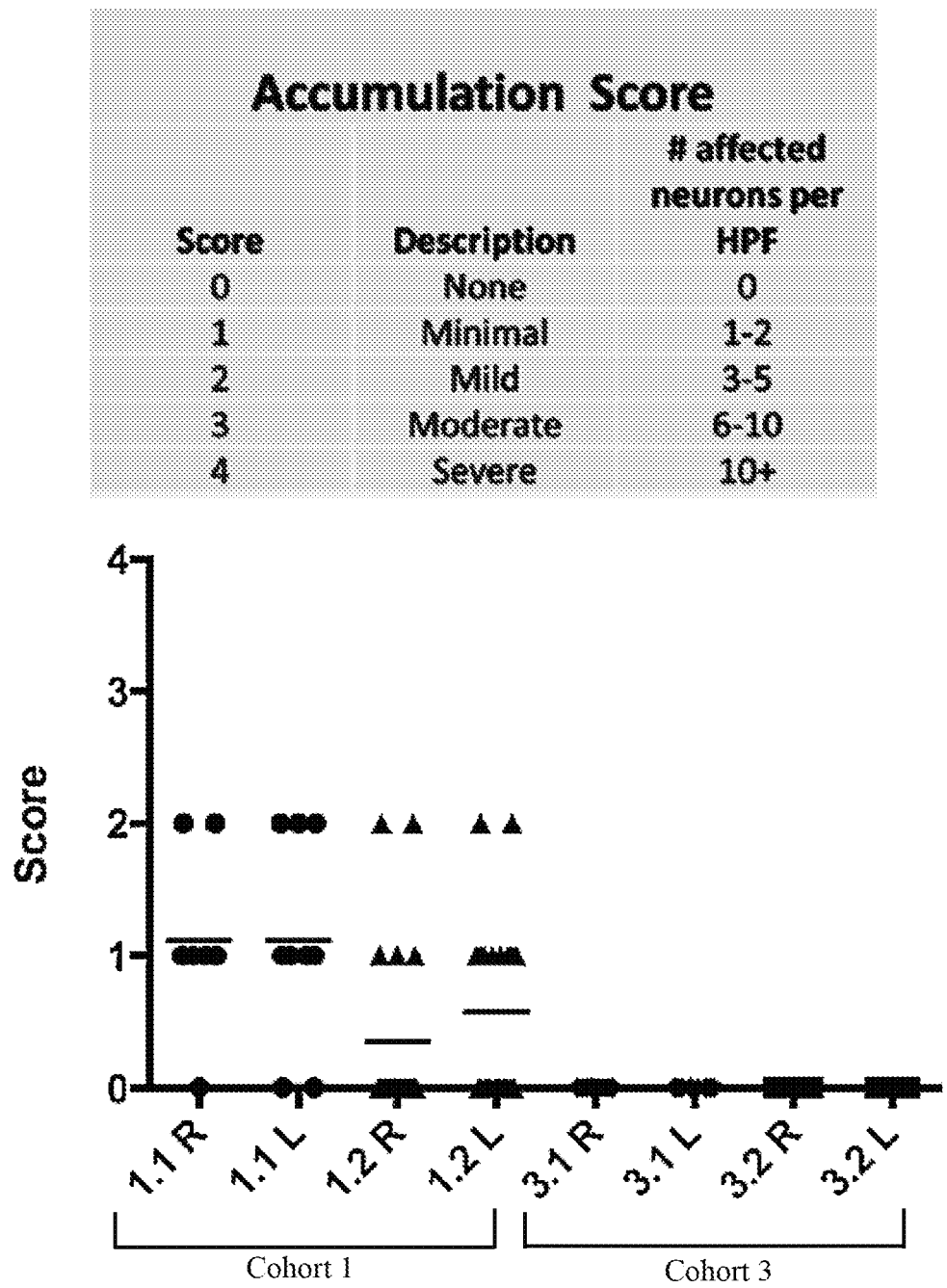
FIG. 45 shows the scoring of intraneuronal accumulation of eosinophilic material in the right and left thalamus of monkeys in cohorts 1 and 3.
Figure 46:
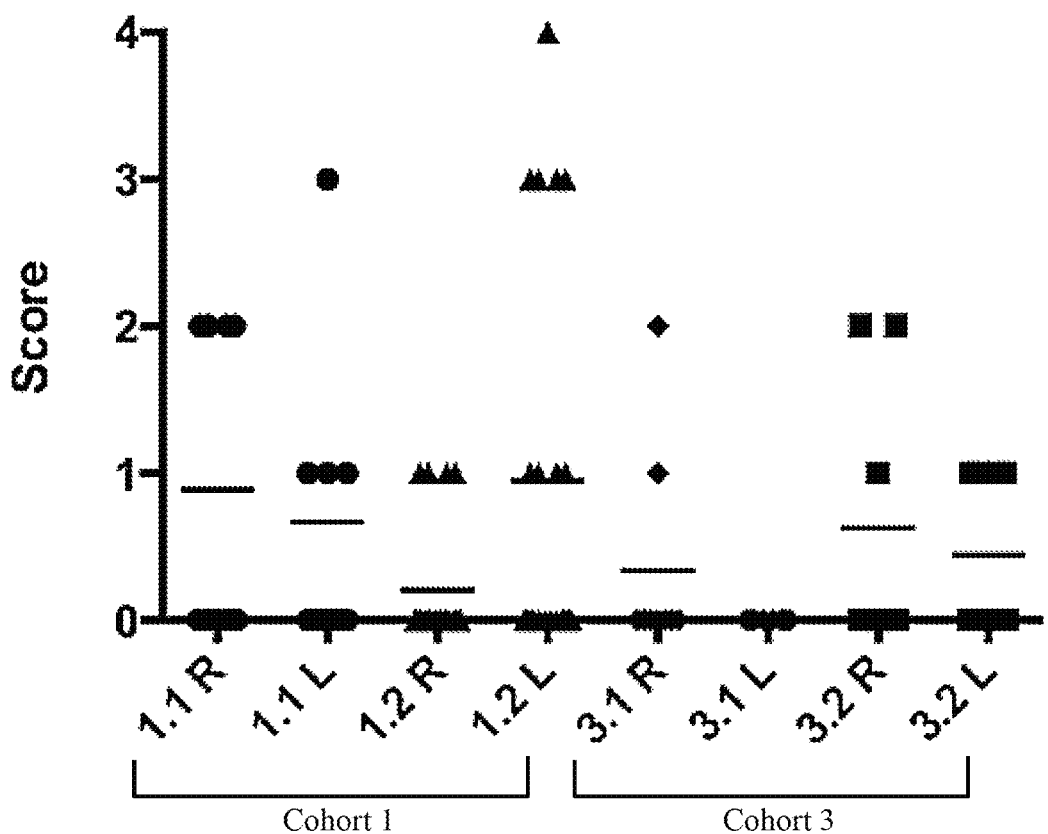
FIG. 46 shows the scoring of neuronal degeneration and necrosis in the right and left thalamus of monkeys in cohorts 1 and 3.
Figure 47:
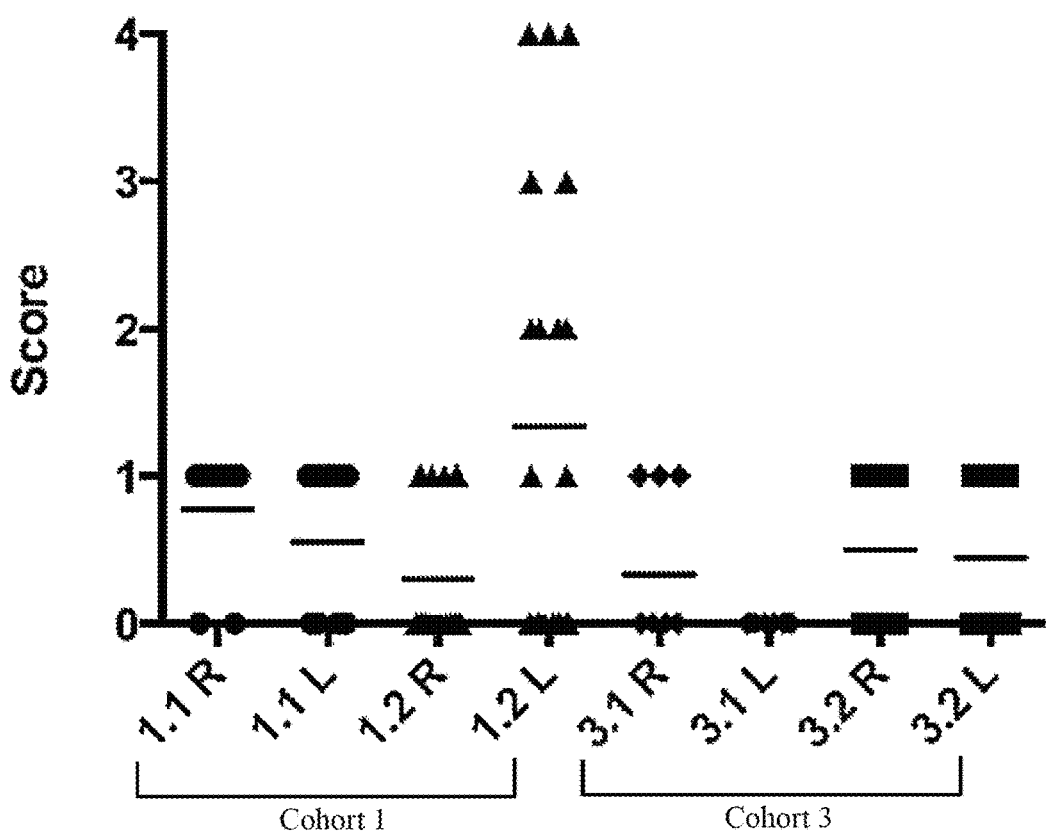
FIG. 47 shows the scoring of inflammation in the right and left thalamus of monkeys in cohorts 1 and 3.
Figure 48B:
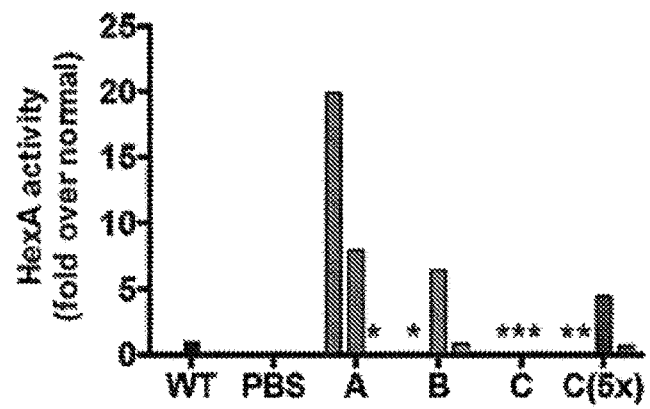
Figure 48C:
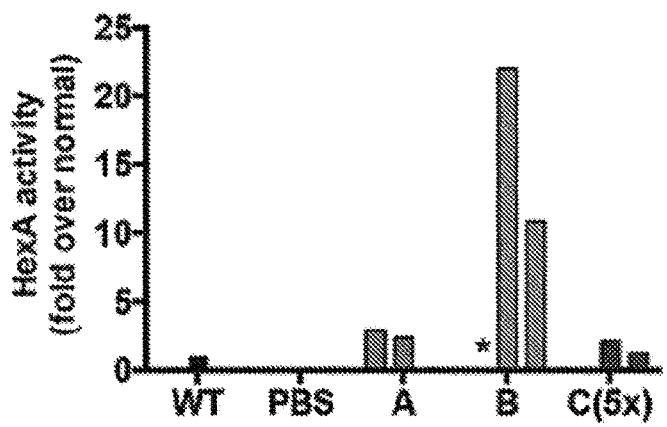
Figure 48D:
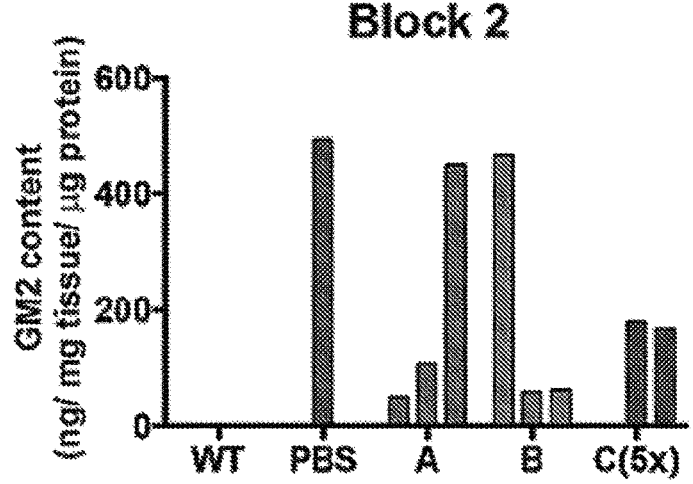
Figure 48E:
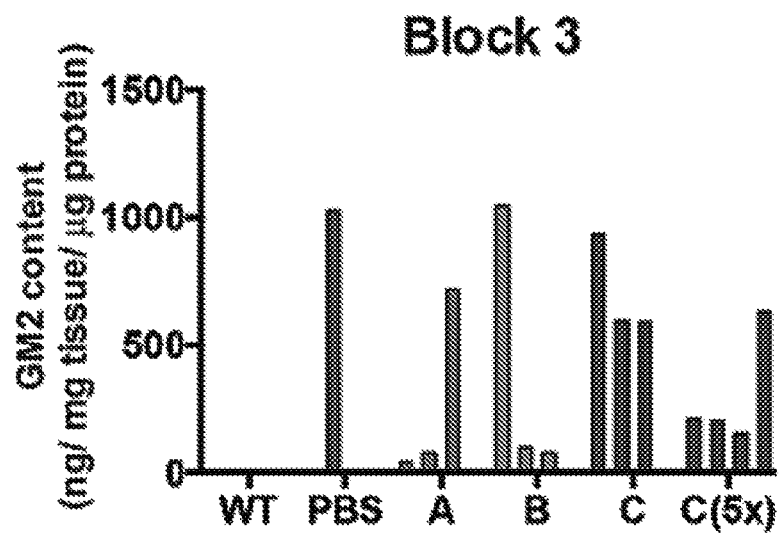
Figure 48F:
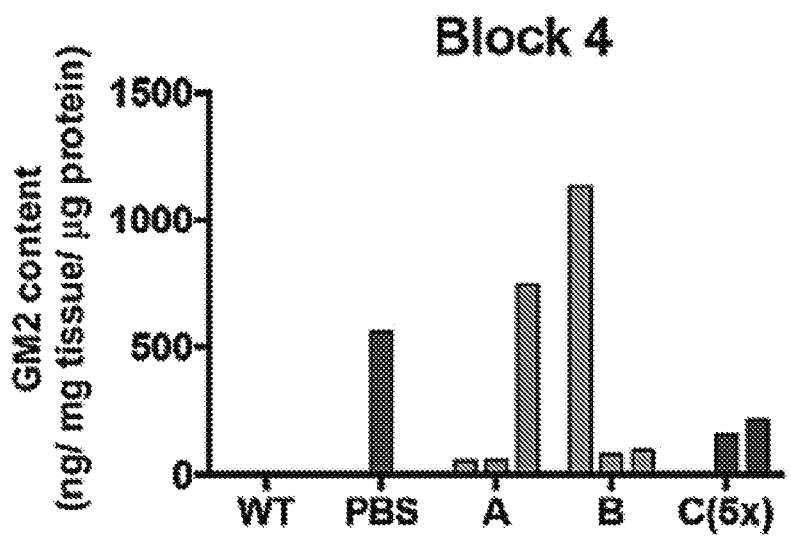
Figure 49A:
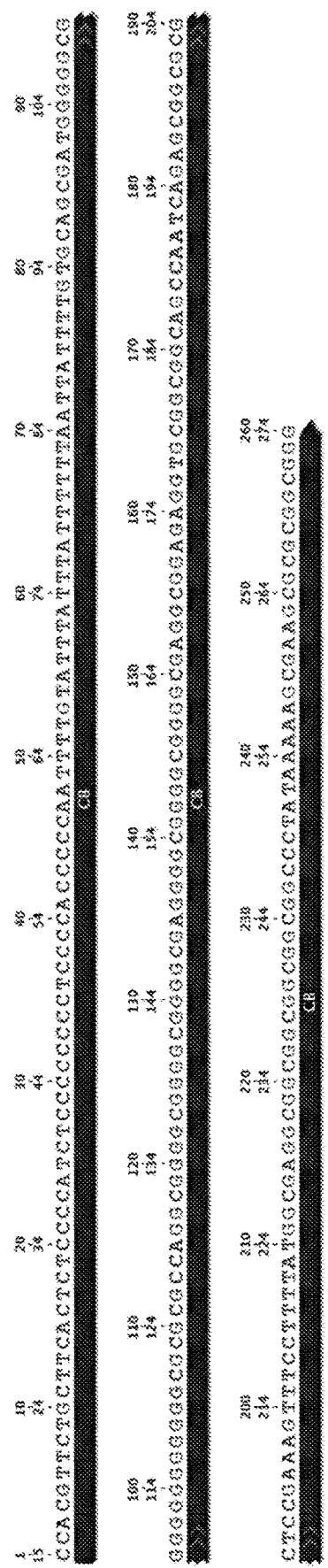
FIGS. 49A-C show structural renderings of promoters described by the disclosure.
Figure 49B:
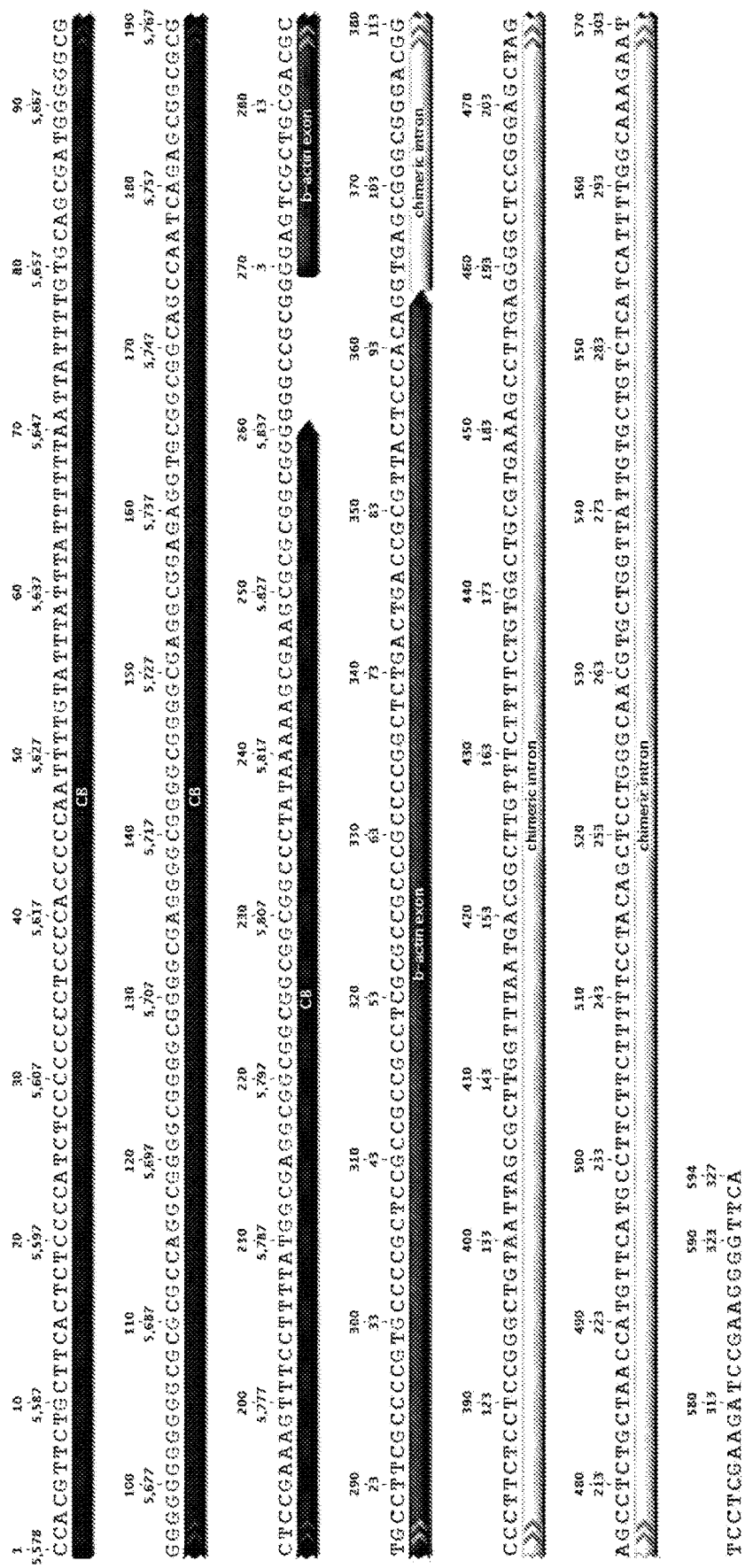
Figure 49C:
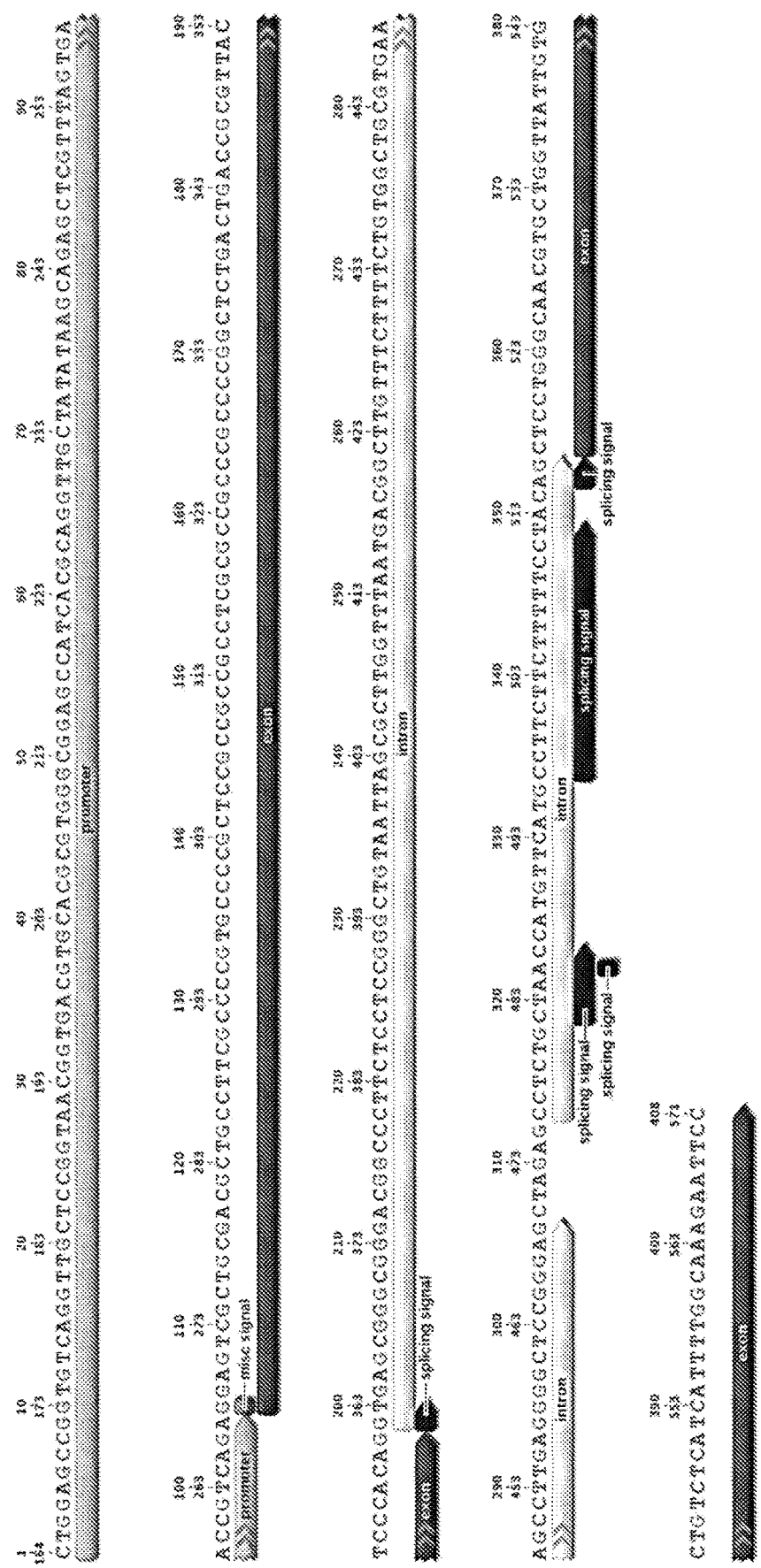

In cohort 3, there was no accumulation of intraneuronal eosinophilic material, rare neuronal degeneration, and satellitosis (FIG. 44A). In one monkey (ID 295709), there was a focus of perivascular gitter cells likely associated with cannulization (FIG. 44B). Serial sections 150 μm apart spanning the entire left and right thalamus of monkeys in cohorts 1 and 3 were prepared for quantification of histological findings namely intraneuronal accumulation of eosinophilic material (FIG. 45), neuronal degeneration and necrosis (FIG. 46), as well as inflammation (FIG. 47). These findings suggest that formulations 1 and 3 have comparable impact in the brain, with the exception of the left injection site in one animal in cohort 1 where there was considerable neuronal degeneration, necrosis, spongiosis and corresponding inflammation. These findings match quite well with the day 90 brain MRI (FIG. 40A).

A small pilot study was carried out to determine the effectiveness of the new vectors AAVrh8-CBA-cmHex (FIG. 19) and AAVrh8-CB-I-cmHex (FIG. 19) to reduce the GM2 content in the CNS of Sandhoff disease (SD) after intracranial delivery. The original AAVrh8-CBA-cmHex-$W^{\Delta 6ATG}$ vector was used as an efficacy reference since all previous studies in SD mice and cats were carried out with this vector. AAV vectors were infused in 4-6 week old SD mice bilaterally into the thalamus and left cerebral lateral ventricle at a total dose/mouse of $4.68 \times 10^9$ vg. This was the 1× dose tested in therapeutic efficacy studies in SD mice injected with the original AAVrh8-CBA-Hex-W vector. Since the total Hex activity in the thalamus of NHP injected with AAVrh8-CB-I-cmHex (cohort 2 in Table 6) was ~20-fold lower than in NHP injected with AAVrh8-CBA-cmHex (cohort 1 in Table 6) we also included an additional cohort of SD mice injected with a 5-fold higher dose (5× dose: $2.34 \times 10^{10}$ vg) of AAVrh8-CB-I-cmHex vector. The mice were sacrificed at 1 month post-injection and the brain divided in 4 coronal blocks ~2 mm to measure Hex activity as well as GM2 ganglioside content (FIG. 48). Hexosaminidase was not detectable in ⅓ SD mice injected with AAVrh8-CBA-cmHex-$W^{\Delta 6ATG}$ (green bars, FIG. 48) and AAVrh8-CBA-cmHex vectors (orange bars, FIG. 48). In mice injected with AAVrh8-CB-I-cmHex vector (blue bars in FIG. 12) we were unable to detect Hex activity in 3/3 and 2/4 animals in the 1× and 5× cohorts respectively. In the comparative studies in athymic nude (nu/nu) mice, the AAVrh8 vectors tested here in SD mice generated considerable Hex overexpression in some instances by 2- to 3-orders of magnitude above normal. This suggests the possibility that the lack of Hex expression in a subset of SD mice may be related to an immune response against the cynomolgus macaque Hex alpha- or beta-subunits that either limits enzyme distribution through a humoral response, or results in transduced cell loss mediated by an adaptive response. Although the number of mice per group is small, there appears to be a direct correlation between Hex activity levels and reduction in GM2 ganglioside. In block 3, a reduction of up to 96% in GM2 ganglioside content in SD mice injected with AAVrh8-CBA-cmHex-$W^{\Delta 6ATG}$ vector was observed, up to 92% for AAVrh8-CBA-cmHex, 42% and 85% reduction in mice injected with 1× and 5× doses, respectively, of AAVrh8-CB-I-cmHex vector.

TABLE 5

Cohorts of NHP injected with new AAV vectors

| Cohort | AAV vector | N |
|---|---|---|
| 1 | AAVrh8-CBA-CMHex | 2 |
| 2 | AAVrh8-CB-I-cmHex | 2 |
| 3 | AAVrh8-P2-I-cmHex | 2 |

TABLE 6

Increase in total Hexosaminidase (HexA + HexB + HexS) activity in the thalamus of AAVrh8-injected NHP

| Total Hex activity (fold over control) | Location in thalamus | Animal | Group |
|---|---|---|---|
| 87.6 | Left dorsal | 295851 | Cohort1 |
| 14.7 | Left ventral | | |
| 2.0 | Right ventral | | |
| 86.6 | Right dorsal | | |
| 82.1 | Left dorsal | c107015 | Cohort 1 |
| 12.9 | Left ventral | | |
| 2.9 | Right ventral | | |
| 53.5 | Right dorsal | | |
| 4.3 | Left dorsal | 295748 | Cohort 2 |
| 1.1 | Left ventral | | |
| 0.9 | Right ventral | | |
| 4.7 | Right dorsal | | |
| 4.7 | Left dorsal | 295847 | Cohort 2 |
| 0.7 | Left ventral | | |
| 2.5 | Right ventral | | |
| 1.1 | Right dorsal | | |
| 5.2 | Left dorsal | 295483 | Cohort 3 |
| 1.0 | Left ventral | | |
| 1.6 | Right ventral | | |
| 8.9 | Right dorsal | | |
| 4.5 | Left dorsal | 295709 | Cohort 3 |
| 0.8 | Left ventral | | |
| 1.9 | Right ventral | | |
| 2.1 | Right dorsal | | |

Example 10

Figure 50:
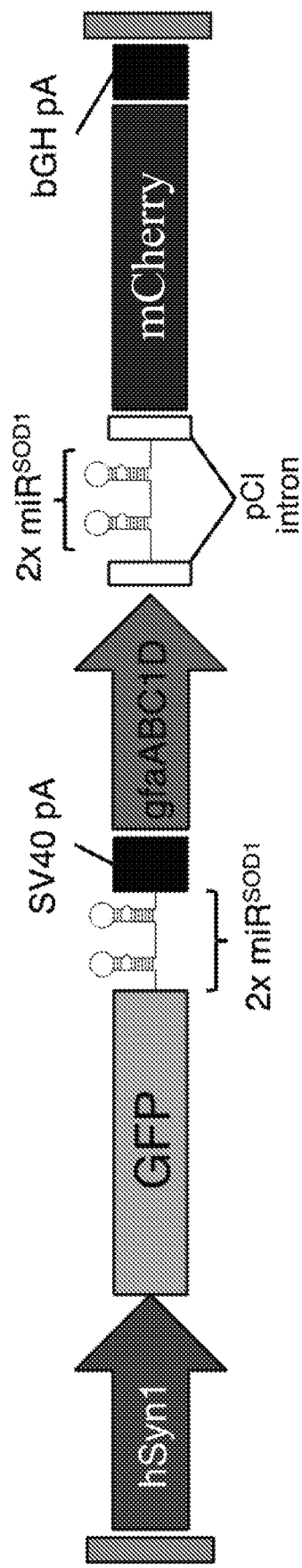
FIG. 50 shows a schematic depiction of dual promoter AAV9-Syn1-GFP-2xmiR$^{SOD1}$/GFAP-2xmiR$^{SOD1}$-mCherry vector.

An AAV vector carrying human synapsin-1 (also referred to as "Syn1") and GfaABC$_1$D (also referred to as "GFAP") promoters for simultaneous dual expression of transgenes of interest in both neurons and astrocytes, respectively, was produced. The vector, referred to as Syn1-GFP-2×miR$^{SOD1}$/GFAP-2×miR$^{SOD1}$-mCherry, contains GFP driven by the neuronal Synapsin1 promoter, and mCherry driven by the astrocytic GFAP promoter; two anti-human SOD1 encoding miRNA are located between the last codon and polyadenylation signal of each of GFP and mCherry (FIG. 50). The vector was packaged using AAV9 capsid protein (FIG. 50). In some embodiments, the vector Syn1-GFP-2×miR$^{SOD1}$/GFAP-2×miR$^{SOD1}$-mCherry is represented by SEQ ID NO: 12.

Figure 51:
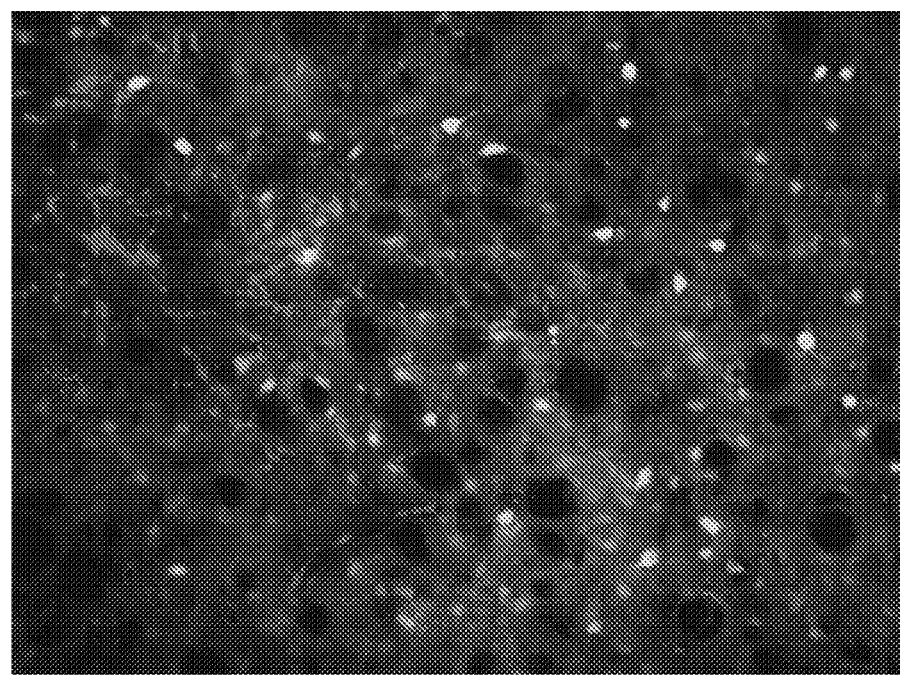
FIG. 51 shows the transduction profile of dual promoter AAV9-Syn1-GFP-2xmiR$^{SOD1}$/GFAP-2xmiR$^{SOD1}$-mCherry after intrastriatal injection in adult SOD1$^{G93A}$ mice. The AAV9 vector contained GFP driven by the neuronal Synapsin1 promoter, and mCherry driven by the astrocytic GFAP promoter. The morphology of GFP (green) and mCherry (red) expressing cells is consistent with neurons and astrocytes, respectively.

The transduction profile of the dual promoter vector was examined. AAV9-Syn1-GFP-2×miR$^{SOD1}$/GFAP-2×miR$^{SOD1}$-mCherry was intrastriatally injected into SOD1$^{G93A}$ adult mice and fluorescence microscopy was performed. Data indicate that the morphology of GFP (green) and mCherry (red) expressing cells is consistent with neurons and astrocytes, respectively (FIG. 51).

Figure 52:
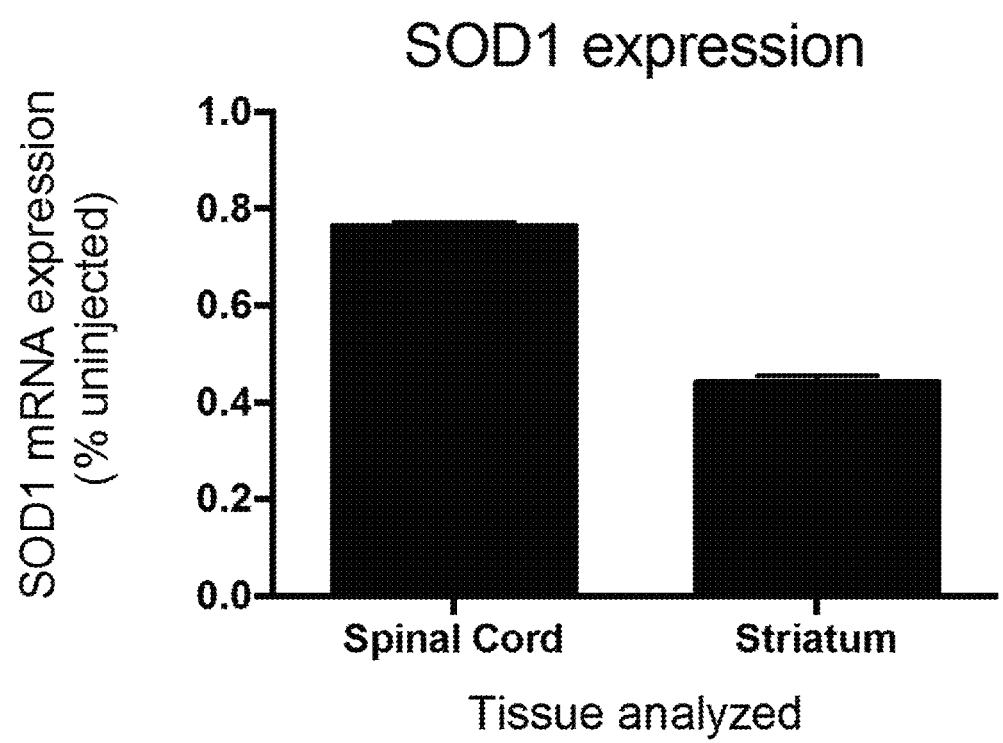
FIG. 52 shows human SOD1 mRNA levels are reduced in adult SOD1$^{G93A}$ mice after injection of a dual promoter AAV9-Syn1-GFP-2xmiR$^{SOD1}$/GFAP-2xmiR$^{SOD1}$-mcherry vector. The artificial microRNAs (miRs) target human SOD1. A decrease in human SOD1 mRNA expression of up to 25% in the spinal cord was observed after an intravenous injection of $1 \times 10^{12}$ total vector genomes. A decrease in human SOD1 mRNA expression of up to 55% in the striatum was observed after a direct intra-striatal injection of $8 \times 10^9$ total vector genomes.

SOD1 mRNA expression was measured. Data indicate that human SOD1 mRNA levels are reduced in adult SOD1$^{G93A}$ mice after injection of a dual promoter AAV9-Syn1-GFP-2×miRSOD1/GFAP-2×miRSOD1-mCherry vector (FIG. 52). A decrease in human SOD1 mRNA expression of up to 25% in the spinal cord was observed after an intravenous injection of 1×10$^{12}$ total vector genomes. A decrease in human SOD1 mRNA expression of up to 55% in the striatum was observed after a direct intra-striatal injection of 8×10$^9$ total vector genomes.

Data indicate that this dual promoter construct results in greater widespread transduction of specific cell types (e.g., neurons and astrocytes) in the CNS than current approaches using ubiquitous promoters (e.g., CBA, U6), with reduced toxicity to non-CNS tissues.

This disclosure is not limited in its application to the details of construction and the arrangement of components set forth in this description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

---

What is claimed is:

1. A recombinant AAV (rAAV) comprising:
a capsid containing a nucleic acid comprising a transgene encoding β-N-acetylhexosaminidase (HexA) or hexosaminidase B (HexB), wherein the transgene is operably linked to a promoter via a chimeric intron and the nucleic acid does not comprise a cytomegalovirus (CMV) enhancer element, and wherein the capsid is serotype AAVrh8.

2. The rAAV of claim 1, wherein the promoter comprises a chicken beta-actin (CB) promoter.

3. The rAAV of claim 1, wherein the nucleic acid comprises two ITRs, and wherein the transgene which is operably linked to the promoter via the chimeric intron is located between the two ITRs.

4. The rAAV of claim 1, wherein the chimeric intron comprises a chicken beta actin intronic sequence and/or a rabbit beta globin intronic sequence.

5. A composition comprising the rAAV of claim 1.

6. The rAAV of claim 1, wherein the transgene encodes a human HexA.

7. The rAAV of claim 1, wherein the transgene encodes a human HexB.

8. A rAAV comprising:
a capsid comprising a nucleic acid comprising a transgene encoding a human HexA or a human HexB, wherein the transgene is operably linked to a chicken beta-actin (CB) promoter via a chimeric intron comprising a chicken beta-actin intronic sequence and/or a rabbit beta-globin intronic sequence, wherein the nucleic acid does not comprise a cytomegalovirus (CMV) enhancer element, and wherein the capsid is of the serotype AAVrh8.

9. The rAAV of claim 8, wherein the CB promoter and the transgene are located between the two inverted terminal repeat (ITR) sequences.

10. The rAAV of claim 9, wherein the two ITR sequences are selected from the group consisting of AAV1 ITR sequences, AAV2 ITR sequences, AAV3 ITR sequences, AAV4 ITR sequences, AAV5 ITR sequences, or AAV6 ITR sequences.

11. The rAAV of claim 8, wherein the transgene encodes a human HexA.

12. The rAAV of claim 8, wherein the transgene encodes a human HexB.

13. A composition comprising the rAAV of claim 8.

* * * * *